(12) United States Patent
Weiner et al.

(10) Patent No.: US 11,945,851 B2
(45) Date of Patent: Apr. 2, 2024

(54) MAGE-A VACCINES AND METHODS OF TREATMENT USING THE SAME

(71) Applicant: The Wistar Institute of Anatomy and Biology, Philadelphia, PA (US)

(72) Inventors: David Weiner, Merion, PA (US); Elizabeth Duperret, Philadelphia, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 428 days.

(21) Appl. No.: 16/619,500

(22) PCT Filed: Jun. 7, 2018

(86) PCT No.: PCT/US2018/036417
§ 371 (c)(1),
(2) Date: Dec. 5, 2019

(87) PCT Pub. No.: WO2018/226931
PCT Pub. Date: Dec. 13, 2018

(65) Prior Publication Data
US 2020/0140508 A1    May 7, 2020

Related U.S. Application Data

(60) Provisional application No. 62/516,607, filed on Jun. 7, 2017.

(51) Int. Cl.
| | | |
|---|---|---|
| *C07K 14/47* | (2006.01) | |
| *A61K 39/00* | (2006.01) | |
| *A61K 39/39* | (2006.01) | |
| *A61K 45/06* | (2006.01) | |
| *A61P 35/00* | (2006.01) | |

(52) U.S. Cl.
CPC .. *C07K 14/4748* (2013.01); *A61K 39/001186* (2018.08); *A61K 39/39* (2013.01); *A61K 45/06* (2013.01); *A61P 35/00* (2018.01); *A61K 2039/53* (2013.01); *A61K 2039/55527* (2013.01); *A61K 2039/55533* (2013.01); *A61K 2039/572* (2013.01); *A61K 2039/86* (2018.08); *A61K 2039/876* (2018.08)

(58) Field of Classification Search
CPC ........ C07K 14/4748; A61K 39/001186; A61K 39/39; A61K 45/06; A61K 2039/53; A61K 2039/55527; A61K 2039/55533; A61K 2039/572; A61K 2039/86; A61K 2039/876; A61K 2039/80; A61P 35/00; A61P 37/04
See application file for complete search history.

(56) References Cited

U.S. PATENT DOCUMENTS

| | | |
|---|---|---|
| 2003/0170792 A1 | 9/2003 | Chaux |
| 2007/0243196 A1 | 10/2007 | Bruck |
| 2012/0003259 A1 | 1/2012 | Chua |
| 2014/0010861 A1 | 1/2014 | Bancel |
| 2016/0331844 A1 | 11/2016 | Fotin-Mleczek |

FOREIGN PATENT DOCUMENTS

WO    WO-2007026078 A2 *   3/2007   ......... A61K 39/0011

OTHER PUBLICATIONS

De Plaen E, De Backer O, Arnaud D, Bonjean B, Chomez P, Martelange V, Avner P, Baldacci P, Babinet C, Hwang SY, Knowles B, Boon T. A new family of mouse genes homologous to the human MAGE genes. Genomics. Jan. 15, 1999;55(2):176-84. doi: 10.1006/geno.1998.5638. PMID: 9933564. (Year: 1998).*
Ngo et al., in The Protein Folding Problem and Tertiary Structure Prediction, 1994, Merz, et al., (ed.), Birkhauser, Boston, MA, pp. 433 and 492-495 (Year: 1994).*
Skolnick, et al. Trends in Biotech. 18, 34-39, 2000, see abstract, in particular (Year: 2000).*
Burgess et al., J of Cell Bio. 111:2129-2138, 1990 (Year: 1990).*
Lazar et al. Molecular and Cellular Biology 8:1247-1252, 1988 (Year: 1988).*
Leninger et al. (Elife. 2019;8:e48909. Published Oct. 22, 2019) (Year: 2019).*
Bowie et al. Science, 247:1306-1310, 1990, p. 1306, col. 2 (Year: 1990).*
G. Bratslavsky, I. Tsimafeyeu, 499P—Identification of first-in-class, naturally occurring LAG3 checkpoint inhibitor, Annals of Oncology, vol. 30, Supplement 5, 2019, p. v188 (Year: 2019).*
Zhu et al, 2012, 'Characterization of T-cell receptors directed against HLA-A*01-restricted and C*07-restricted epitopes of MAGE-A3 and MAGE-A12', J Immunother 35:680-688.
Atanackovic al., 2008, 'Booster vaccination of cancer patients with MAGE-A3 protein reveals long-term immunological memory or tolerance depending on priming', PNAS 105:1650-1655.
Barker and Salehi., 2002, 'The MAGE proteins: Emerging roles in cell cycle progression, apoptosis, and neurogenetic disease', J Neurosci 67:705-712.
Bluman et al., 2007, 'Lysis of human chondrosarcoma cells by cytolytic T lymphocytes recognizing a MAGE-A3 antigen presented by HLA-A1 molecules', J Orthop Res 25:678-684.
Cameron et al., 2013, 'Identification of a Titin-derived HLA-A1-presented peptide as a cross-reactive target for engineered MAGE A3-directed T cells', Sci Transl Med 5:197ra103.
Chaux P et al., 1999, 'Identification of MAGE-3 Epitopes Presented by HLA-DR Molecules to CD4 + T Lymphocytes', J Exp Med 189:767-778.
Chinnasamy et al., 2000, 'A TCR Targeting the HLA-A*0201-Restricted Epitope of MAGE-A3 Recognizes Multiple Epitopes of the MAGE-A Antigen Superfamily in Several Types of Cancer', J Immunol 186:685-696.

(Continued)

Primary Examiner — Jessica H Roark
Assistant Examiner — Francesca Edgingtongiordan
(74) Attorney, Agent, or Firm — Riverside Law LLP

(57) ABSTRACT

Disclosed herein are compositions and methods for treating and/or preventing cancer in mammals, and in particular, vaccines that treat and provide protection against tumor growth.

17 Claims, 25 Drawing Sheets

Specification includes a Sequence Listing.

(56) References Cited

OTHER PUBLICATIONS

Dankort et al., 2009, 'Braf(V600E) cooperates with Pten loss to induce metastatic melanoma', Nat Genet 41:544-552.

De Smet et al., 1999, 'DNA Methylation Is the Primary Silencing Mechanism for a Set of Germ Line- and Tumor-Specific Genes with a CpG-Rich Promoter', Mol Cell Biol 19:7327-7333.

Dhodapkar et al., 2000, 'Paucity of functional T-cell memory to melanoma antigens in healthy donors and melanoma patients', Clin Cancer Res 6:4831-4838.

Dillman, 2016, 'Is there a role for therapeutic cancer vaccines in the age of checkpoint inhibitors? Hum Vaccin Immunother', Hum Vaccin Immunother 13:528-532; https://www.tandfonline.com/doi/full/10.1080/21645515.2016.1244149.

Doyle et al., 2010, 'MAGE-RING protein complexes comprise a family of E3 ubiquitin ligases', Mol Cell 39:963-974.

Dunker et al., 2001, 'Intrinsically disordered protein. J Mol Graph Model', J Mol Graph Model 19:26-59.

Duperret et al., 2017, 'Alteration of the tumor stroma using a consensus DNA vaccine targeting Fibroblast Activation Protein (FAP) synergizes with anti-tumor vaccine therapy in mice', Clin Cancer Res 24:1190-1201.

Gaugler et al., 1994, 'Human gene MAGE-3 codes for an antigen recognized on a melanoma by autologous cytolytic T lymphocytes', J Exp Med 179:921-930.

Gotter et al., 2004, 'Medullary epithelial cells of the human thymus express a highly diverse selection of tissue-specific genes colocalized in chromosomal clusters', J Exp Med 199:155-166.

Graff-Dubois et al., 2002, 'Generation of CTL Recognizing an HLA-A*0201-Restricted Epitope Shared by MAGE-A1, -A2, -A3, -A4, -A6, -A10, and -A12 Tumor Antigens: Implication in a Broad-Spectrum Tumor Immunotherapy', J Immunol 169:575-580.

Huang et al., 1999, 'Cytolytic T Lymphocytes Recognize an Antigen Encoded by MAGE-A10 on a Human Melanoma', J Immunol 162.

International Search Report and Written Opinion issued in App. No. PT/US18/36417, dated Oct. 30, 2018, 11 pages.

Jungbluth et al., 2005, 'The cancer-testis antigens CT7 (MAGE-C1) and MAGE-A3/6 are commonly expressed in multiple myeloma and correlate with plasma-cell proliferation', Blood 106:167-174.

Kageyama et al., 'Adoptive Transfer of MAGE-A4 T-cell Receptor Gene-Transduced Lymphocytes in Patients with Recurrent Esophageal Cancer', 2015 Clin Cancer Res. 21.

Kruit et al., 2013, 'Selection of immunostimulant AS15 for active immunization with MAGE-A3 protein: results of a randomized phase II study of the European Organisation for Research and Treatment of Cancer Melanoma Group in Metastatic Melanoma', J Clin Oncol 31:2413-2420.

Linette et al., 2013, 'Cardiovascular toxicity and titin cross-reactivity of affinity-enhanced T cells in myeloma and melanoma', Blood 122:863-871.

Liu et al., 2008, 'Norcantharidin induces melanoma cell apoptosis through activation of TR3 dependent pathway', Cancer Res 68:8104-8112.

Liu W et al., 2008, The melanoma-associated antigen A3 mediates fibronectin-controlled cancer progression and metastasis, Cancer Res. 68:8104-12.

Manici et al., 1999, 'Melanoma Cells Present a MAGE-3 Epitope to CD4 + Cytotoxic T Cells in Association with Histocompatibility Leukocyte Antigen DR11', J Exp Med 189:871-876.

Marchand et al., 1999, 'Tumor regressions observed in patients with metastatic melanoma treated with an antigenic peptide encoded by gene MAGE-3 and presented by HLA-A1', Int J cancer 80:219-230.

Meeth et al., 2016, 'The YUMM lines: a series of congenic mouse melanoma cell lines with defined genetic alterations', Pigment Cell Melanoma Res 29:590-597.

Morgan et al., 2013, 'Cancer regression and neurological toxicity following anti-MAGE-A3 TCR gene therapy', J Immunother 36:133-151.

Pineda, Carlos T., et al., "Degradation of AMMPK by a Cancer-Specific Ubiquitin Ligase" Cell, vol. 160, No. 4, pp. 715-728, 2015.

Roeder et al., 2005, 'MAGE-A3 is a frequent tumor antigen of metastasized melanoma. Arch Dermatol Res', Arch Dermatol Res 296:314-319.

Sali and Blundell, 1993, 'Comparative protein modelling by satisfaction of spatial restraints', J Mol Biol 234:779-815.

Schultz et al., 2000, 'A MAGE-A3 peptide presented by HLA-DP4 is recognized on tumor cells by CD4+ cytolytic T lymphocytes', Cancer Res. 60:6272-6275.

So et al., 2006, 'Lack of tumor recognition by cytolytic T lymphocyte clones recognizing peptide 195-203 encoded by gene MAGE-A3 and presented by HLA-A24 molecules', Cancer Immunol Immunother 56:259-269.

Sreenivasan et al., 2018, 'Measuring glioma volumes: A comparison of linear measurement based formulae with the manual image segmentation technique', J Cancer Res Ther 12:161.

Stockert et al., 1998, 'A survey of the humoral immune response of cancer patients to a panel of human tumor antigens', J Exp Med 187:1349-1354.

Tajima et al., 2003, Expression of cancer/testis (CT) antigens in lung cancer. Lung cancer, Lung cancer 42:23-33.

Tebas et al., 2017, 'Safety and Immunogenicity of an Anti-Zika Virus DNA Vaccine—Preliminary Report', NEJM Epub NEJMoa1708120.

Thompson et al., 2012, MAGE-A3 expression in patients screened for the DERMA trial: A phase III trial testing MAGE-A3 immunotherapeutic in the adjuvant setting for stage IIIB-C-Tx melanoma, J Clin Oncol.

Trimble et al. 2015, 'Safety, efficacy, and immunogenicity of VGX-3100, a therapeutic synthetic DNA vaccine targeting human papillomavirus 16 and 18 E6 and E7 proteins for cervical intraepithelial neoplasia 2/3: a randomised, double-blind, placebo-controlled phase 2b trial', Lancet 386:2078-2088.

Van der Bruggen et al., 1991, 'A gene encoding an antigen recognized by cytolytic T lymphocytes on a human melanoma', Science 254:1643-1647.

Vansteenkiste et al., 2013, 'Adjuvant MAGE-A3 immunotherapy in resected non-small-cell lung cancer: Phase II randomized study results', J Clin Oncol 31:2396-403.

Vantomme et al., 2004, 'Immunologic analysis of a phase I/II study of vaccination with MAGE-3 protein combined with the AS02B adjuvant in patients with MAGE-3-positive tumors', J Immunother 27:124-135.

Walters et al., 2017, 'A Novel DNA Vaccine Platform Enhances Neo-antigen-like T Cell Responses against WT1 to Break Tolerance and Induce Anti-tumor Immunity', Mol Ther. 25:976-988.

Wang et al., 2009, 'A Mage3/Heat Shock Protein70 DNA vaccine induces both innate and adaptive immune responses for the antitumor activity', Vaccine 28:561-570.

Webb and Sali, 2016, 'Comparative Protein Structure Modeling Using Modeller', Curr Protoc Protein Sci 86:2.9.1-2.9.37; http://doi.wiley.com/10.1002/cpps.20.

Weber et al., 1994, 'Expression of the MAGE-1 tumor antigen is up-regulated by the demethylating agent 5-aza-2'-deoxycytidine', Cancer Res .54:1766-1771.

Wischnewski et al., 2006, 'Promoter demethylation and histone acetylation mediate gene expression of MAGE-A1, -A2, -A3, and -A12 in human cancer cells', Mol Cancer Res 4:339-349.

Yan et al., 2017, 'Broad cross-protective anti-hemagglutination responses elicited by influenza microconsensus DNA vaccine', Vaccine 36:3079-3089.

Yang et al, 2007, MAGE-A, mMage-b, and MAGE-C Proteins Form Complexes with KAP1 and Suppress p53-Dependent Apoptosis in MAGE-Positive Cell Lines, Cancer Res. 67:9954-9962.

You et al., 2001, 'A Retrogen Strategy for Presentation of an Intracellular Tumor Antigen as an Exogenous Antigen by Dendritic Cells Induces Potent Antitumor T Helper and CTL Responses', Cancer Res 61.

\* cited by examiner

A

B

C

D

E

F

MAGE-A VACCINES AND METHODS OF TREATMENT USING THE SAME

CROSS-REFERENCE TO RELATED APPLICATIONS

This application is a U.S. national phase application filed under 35 U.S.C. § 371 claiming priority to International Patent Application No. PCT/US18/36417, filed Jun. 7, 2018, which is entitled to priority under 35 U.S.C. § 119(e) to U.S. Provisional Application No. 62/516,607, filed Jun. 7, 2017, the contents of each of which are incorporated by reference herein in their entireties.

TECHNICAL FIELD

Disclosed herein are compositions and methods for treating cancer and in particular, vaccines that treat and provide protection against tumor growth.

BACKGROUND

Therapeutic cancer vaccines are receiving increasing interest for treatment of various types of cancer, in particular for patients who do not have naturally occurring anti-tumor immunity, or who do not benefit from immune checkpoint blockade therapy (Dillman, 2016 Hum Vaccin Immunother 13:528-32). However, identifying appropriate antigens with tumor-restricted expression, high potential for immunogenicity in humans, and high expression in multiple tumor types has remained challenging.

In the early 1990's, the MAGE-1, melanoma antigen-1 (now re-named MAGE-A1), protein was the first cancer antigen discovered to be recognized by cytolytic T lymphocytes in a human melanoma patient (van der Bruggen et al., 1991, Science 254:1643-7). Subsequently, 10 additional MAGE-A family members were identified in various human cancers, all of which have no or low expression in normal human tissues, with the exception of the placenta and non-MHC presenting germ cells of the testis (Thompson et al., 2012, Am Soc Clin Oncol; Roeder et al., 2005, Arch Dermatol Res 296:314-9 De Smet et al., 1999, Mol Cell Biol 19:7327-3). Due to this restricted expression, the MAGE-A family represents an ideal immune therapy target. Furthermore, because of this restricted expression it may less subject to tissue-specific immune tolerance, making it easier to generate a robust immune response against this family of antigens. In support of this concept, T lymphocytes specific for both class I and II epitopes of various MAGE-A family members have been identified in cancer patients (van der Bruggen et al., 1991, Science 254:1643-7; Gaugler et al., 1994, J Exp Med 179:921-30; Chaux Petal., 1999, J Exp Med 189:767-78; Manici et al., 1999, J Exp Med 189:871-6; Schultz et al., 2000, Cancer Res. 60:6272-5; Chinnasamy et al., 2000, J Immunol 186:685-96; Graff-Dubois et al, 2002, J Immunol 169:575-80; Huang et al., 1999, J Immunol 162; So et al., 2006, Cancer Immunol Immunother 56:259-69; Zhu et al, 2012, J Immunother 35:680-8; Bluman et al., 2007, J Orthop Res 25:678-84; Kageyama et al., 2015 Clin Cancer Res. 21).

The attractiveness of the MAGE family for cancer immune therapy has resulted in the initiation of several clinical trials for vaccines targeting a common family member MAGE-A3. This specific isoform was chosen for clinical study because it was thought at the time to have the highest expression compared to other isoforms in various solid tumors (Vantomme et al., 2004, J Immunother 27:124-35).

Efforts to target MAGE-A3 have utilized vaccination with a recMAGE-A3 recombinant protein formulation or cellular therapies using CD8+ T cells engineered to express a high-affinity MAGE-A3-targeted TCR. While the rec-MAGE-A3 vaccine was capable of inducing clear humoral responses in cancer patients, the vaccine produced poor CD8+ T cell responses and ultimately failed to demonstrate efficacy in a Phase III clinical trial of non-small cell lung cancer (Vansteenkiste et al., 2013, J Clin Oncol 31:2396-403; Kruit et al., 2013, J Clin Oncol 31:2413-20; Atanackovic al., 2008, PNAS 105:1650-5). In contrast, the MAGE-A3 TCR cellular therapy demonstrated anti-tumor activity in several patients; however, this therapy exhibited unexpected off-tumor toxicity resulting in several patient deaths in early-stage clinical trials (Chinnasamy et al., 2000, J Immunol 186:685-96; Cameron et al., 2013, Sci Transl Med 5:197ra103; Linette et al., 2013, Blood 122:863-71; Morgan et al., 2013, J Immunother 36:133-51). Thus, development of therapies targeting antigens in the MAGE-A family driving a more robust T cell response, but exhibiting a better safety profile is of high priority.

Peptide or DNA vaccination approaches for targeting the MAGE-A family members may represent important tools in this regard (Wang et al., 2009, Vaccine 28:561-70; You et al., 2001, Cancer Res 61). Several peptides targeting various shared MAGE-A epitopes have been tested in a pre-clinical or clinical setting, and have shown some induction of limited T cell responses as well as patient specific clinical responses (Graff-Dubois et al, 2002, J Immunol 169:575-80; Marchand et al., 1999, Int J cancer 80:219-30). However, these peptides are HLA-restricted and accordingly this strategy is limited to a subset of patients. Clinical trials utilizing optimized synthetic DNA with improved electroporation technology have shown impressive clinical responses and incredible promise for targeting infectious disease and virally driven cancers (Trimble et al. 2015, Lancet 386: 2078-88; Tebas et al., 2017, NEJM Epub NEJMoa1708120). Synthetic DNA vaccines also have the advantage of encoding entire antigens, instead of individual peptides, in order to generate a broader HLA response that is not restricted and is capable of generating a polyfunctional immune response. Another important advantage of this platform is the ability to design consensus immunogens to induce cross-reactive immune responses against similar, conserved strains of viruses (Yan et al., 2017, Vaccine 36:3079-89). In the cancer setting, this consensus design strategy can be adapted here to help break tolerance against self-antigens (Walters et al., 2017, Mol Ther. 25:976-88; Duperret et al., 2017, Clin Cancer Res 24:1190-201).

Clinical studies have targeted MAGE-A3, a prototype antigen that is a member of the MAGE-A family of antigens, in melanoma and lung carcinoma. However, these studies have not yet had a significant impact due to poor CD8+ T cell immunogenicity, platform toxicity, or perhaps limited target antigen availability. There have been several attempts to target MAGE in the clinic, all of which have focused on MAGE-A3 in patients with melanoma or non-small cell lung cancer. Recently 2 recent clinical trials have been carried out to target HLA-restricted peptides within the MAGE-A3 antigen. While some clinical regression was observed in these patients, there was unexpected toxicity. Three patients experienced mental status changes and 2 of these patients died due to neurological toxicity. This was later found to be due to extremely low levels of MAGE-A9 or MAGE-A12 expression in the brain of patients.

Accordingly, a need exists for the identification and development of compositions and methods for the prevention and/or treatment of cancer. Furthermore, more effective treatments are required to delay disease progression and/or decrease mortality in subjects suffering from cancer.

SUMMARY OF INVENTION

In one aspect, the present invention provides a vaccine comprising a nucleotide sequence encoding a consensus MAGE-A antigen. In one embodiment, the consensus MAGE-A antigen comprises an amino acid sequence selected from the group consisting of SEQ ID NO:1, SEQ ID NO:3, SEQ ID NO:5, SEQ ID NO:7, SEQ ID NO:9, SEQ ID NO:11, an amino acid sequence that is 95% identical or greater to SEQ ID NO:1, an amino acid sequence that is 95% identical or greater to SEQ ID NO:3, an amino acid sequence that is 95% identical or greater to SEQ ID NO:5, an amino acid sequence that is 95% identical or greater to SEQ ID NO:7, an amino acid sequence that is 95% identical or greater to SEQ ID NO:9 and an amino acid sequence that is 95% identical or greater to SEQ ID NO:11.

In one embodiment, the vaccine further comprises one or more nucleotide sequences encoding one or more additional cancer antigens. In one embodiment, the one or more additional cancer antigens comprise one or more antigens selected from the group consisting of the amino acid sequence of tyrosinase (Tyr), the amino acid sequence of tyrosinase-related protein 1 (TYRP1), the amino acid sequence of tyrosinase-related protein 2 (TYRP2), the amino acid sequence of hTERT, the amino acid sequence of growth hormone release hormone (GHRH), the amino acid sequence of MART-1/melan-A antigen (MART-1/Melan-A), the amino acid sequence of cancer testis antigen (NY-ESO-1), the amino acid sequence of cancer testis antigen II (NY-ESO-2), the amino acid sequence of PRAME, the amino acid sequence of WT1, the amino acid sequence of PSA, the amino acid sequence of PSMA, the amino acid sequence of STEAP, the amino acid sequence of PSCA, the amino acid sequence of gp100, the amino acid sequence of a viral antigen, and a combination thereof.

In one embodiment, the vaccine further comprises one or more nucleotide sequences encoding one or more immune checkpoint inhibitors. In one embodiment, the immune checkpoint inhibitor is selected from the group consisting of: anti-PD-1 antibody, anti-PD-L1 antibody, anti-TIM-3 antibody, anti-LAG-3 antibody, anti-CTLA4 antibody, and a combination thereof.

In one embodiment, the nucleotide sequence comprises a nucleotide sequence selected from the group consisting of: SEQ ID NO:2, SEQ ID NO:4, SEQ ID NO:6, SEQ ID NO:8 SEQ ID NO:10, SEQ ID NO:12, a nucleotide sequence that is 95% identical or greater to SEQ ID NO:2, a nucleotide sequence that is 95% identical or greater to SEQ ID NO:4, a nucleotide sequence that is 95% identical or greater to SEQ ID NO:6, a nucleotide sequence that is 95% identical or greater to SEQ ID NO:8, a nucleotide sequence that is 95% identical or greater to SEQ ID NO:10, and a nucleotide sequence that is 95% identical or greater to SEQ ID NO:12.

In one embodiment, the vaccine comprises one or more plasmids.

In one embodiment, the vaccine comprises a nucleotide sequence encoding an adjuvant. In one embodiment, the adjuvant is IL-12, IL-15, IL-28, or RANTES.

In one aspect, the present invention provides a method of treating cancer in a subject in need thereof. In one embodiment, the method comprises administering a vaccine comprising a nucleotide sequence encoding a consensus MAGE-A antigen. In one embodiment the consensus MAGE-A antigen comprises an amino acid sequence selected from the group consisting of SEQ ID NO:1, SEQ ID NO:3, SEQ ID NO:5, SEQ ID NO:7, SEQ ID NO:9, SEQ ID NO:11, an amino acid sequence that is 95% identical or greater to SEQ ID NO:1, an amino acid sequence that is 95% identical or greater to SEQ ID NO:3, an amino acid sequence that is 95% identical or greater to SEQ ID NO:5, an amino acid sequence that is 95% identical or greater to SEQ ID NO:7, an amino acid sequence that is 95% identical or greater to SEQ ID NO:9 and an amino acid sequence that is 95% identical or greater to SEQ ID NO:11.

In one embodiment, the administering step comprises electroporation. In one embodiment, the method further comprises administering one or more nucleotide sequences encoding one or more immune checkpoint inhibitors. In one embodiment, the immune checkpoint inhibitor is selected from the group consisting of: anti-PD-1 antibody, anti-PD-L1 antibody, anti-TIM-3 antibody, anti-LAG-3 antibody, anti-CTLA4 antibody, and a combination thereof.

In one embodiment, the cancer is selected from the group consisting of: a blood cancer, lung cancer, melanoma, head and neck cancer, prostate cancer, liver cancer, cervical cancer, anal cancer, a papilloma and a combination thereof.

In one aspect, the present invention provides a nucleic acid molecule comprising one or more nucleotide sequences selected from the group consisting of: SEQ ID NO:2, SEQ ID NO:4, SEQ ID NO:6, SEQ ID NO:8 SEQ ID NO:10, SEQ ID NO:12, a nucleotide sequence that is 95% identical or greater to SEQ ID NO:2, a nucleotide sequence that is 95% identical or greater to SEQ ID NO:4, a nucleotide sequence that is 95% identical or greater to SEQ ID NO:6, a nucleotide sequence that is 95% identical or greater to SEQ ID NO:8, a nucleotide sequence that is 95% identical or greater to SEQ ID NO:10, and a nucleotide sequence that is 95% identical or greater to SEQ ID NO:12. In one embodiment, the nucleotide sequence comprises one or more plasmids.

In one aspect, the present invention provides a protein comprising one or more amino acid sequences selected from the group consisting of: SEQ ID NO:1, SEQ ID NO:3, SEQ ID NO:5, SEQ ID NO:7, SEQ ID NO:9, SEQ ID NO:11, an amino acid sequence that is 95% identical or greater to SEQ ID NO:1, an amino acid sequence that is 95% identical or greater to SEQ ID NO:3, an amino acid sequence that is 95% identical or greater to SEQ ID NO:5, an amino acid sequence that is 95% identical or greater to SEQ ID NO:7, an amino acid sequence that is 95% identical or greater to SEQ ID NO:9 and an amino acid sequence that is 95% identical or greater to SEQ ID NO:11.

BRIEF DESCRIPTION OF THE DRAWINGS

FIG. 1, comprising FIG. 1A depict the percentage of tumors expressing indicated MAGE-A isoform, based on RSEM RNAseq expression data. FIG. 1B depicts the overall percentage of all tumor samples available from GDAC that express the indicated isoform. FIG. 1C depicts the percentage of tumors expressing multiple MAGE-A isoforms simultaneously.

FIG. 2, comprising FIG. 2A depicts the general domain structure of the MAGE-A proteins. The N terminal is predicted to be unstructured using methods for detecting putative intrinsically disordered regions in proteins. FIG. 2B depicts the phylogenetic tree for murine MAGE-A families. Sequences were aligned using ClustalX2. Indicated are the sequences used for each consensus vaccine. FIG. 2C depicts the phylogenetic tree for human MAGE-A families. Sequences were aligned using ClustalX2. Indicated are the sequences used for each consensus vaccine. FIG. 2D depicts a comparative model, shown in cpk format, for the MHD region of the murine consensus vaccine. FIG. 2E depicts a comparative model, shown in cpk format, for the MHD region of the human consensus 1 vaccine. FIG. 2F depicts a comparative model, shown in cpk format, for the MHD region of the human consensus 2 vaccine. Red residues indicate identity in the consensus with all sequences and yellow indicates residues that differ in one or more of the MAGE-A native isoforms.

FIG. 3, comprising FIG. 3A depicts a schematic of the immunization schedule. C57Bl/6 mice were immunized 3 times at 2 week intervals and sacrificed 1 week following final vaccination. Mice were immunized with 25 µg of DNA followed by electroporation. FIG. 3B depicts the frequency of mouse MAGE-A isoform-specific IFNγ spot-forming units (SFU) per million splenocytes isolated from vaccinated mice. Splenocytes were stimulated with consensus peptides matching the vaccine sequence. FIG. 3C depicts the frequency of mouse MAGE-A isoform-specific IFNγ spot-forming units (SFU) per million splenocytes isolated from vaccinated mice. Splenocytes were stimulated with mouse MAGE-A1 specific peptides. FIG. 3D depicts the frequency of mouse MAGE-A isoform-specific IFNγ spot-forming units (SFU) per million splenocytes isolated from vaccinated mice. Splenocytes were stimulated with mouse MAGE-A2 specific peptides. FIG. 3E depicts the frequency of mouse MAGE-A isoform-specific IFNγ spot-forming units (SFU) per million splenocytes isolated from vaccinated mice. Splenocytes were stimulated with mouse MAGE-A3 specific peptides. FIG. 3F depicts the frequency of mouse MAGE-A isoform-specific IFNγ spot-forming units (SFU) per million splenocytes isolated from vaccinated mice. Splenocytes were stimulated with mouse MAGE-A5 specific peptides. FIG. 3G depicts the frequency of mouse MAGE-A isoform-specific IFNγ spot-forming units (SFU) per million splenocytes isolated from vaccinated mice. Splenocytes were stimulated with mouse MAGE-A6 specific peptides. FIG. 3H depicts the frequency of mouse MAGE-A isoform-specific IFNγ spot-forming units (SFU) per million splenocytes isolated from vaccinated mice. Splenocytes were stimulated with mouse MAGE-A8 specific peptides. FIG. 3I depicts the intracellular cytokine staining of splenocytes isolated from control (pVax) or immunized (MAGE-A) mice, stimulated with the indicated peptides. Shown is the frequency of IFNγ+ CD8 T cells. FIG. 3J depicts the intracellular cytokine staining of splenocytes isolated from control (pVax) or immunized (MAGE-A) mice, stimulated with the indicated peptides. Shown is the frequency of CD107a+/IFNγ+/T-bet+ CD8 T cells. FIG. 3K depicts the intracellular cytokine staining of splenocytes isolated from control (pVax) or immunized (MAGE-A) mice, stimulated with the indicated peptides. Shown is the frequency of TNFα+CD8 T cells. Significance was determined by a student's t-test. *$p<0.05$, $p<0.01$, *$p<0.001$, ****$p<0.0001$. n=5 mice per group. A representative of two independent experiments is shown. Error bars indicate ±SEM.

FIG. 4, comprising FIG. 4A depicts IFNγ ELISpot responses to consensus vaccine-matched peptides. FIG. 4B depicts IFNγ ELISpot responses to consensus individual MAGE-A isoform matched peptides. 5 mice were used in the control group, and 15 mice were used in the consensus MAGE-A immunized group. Error bars indicate ±SEM.

FIG. 5, comprising FIG. 5A depicts a schematic of the tumor study outline. Tyr:: CreER; BRAF$^{Ca/+}$; Pten$^{lox/lox}$ transgenic mice were administered topical tamoxifen on their backs on day 0 to initiate melanoma formation. Mice were immunized with either control (pVax) or MAGE-A vaccine once weekly starting on day 7 for a total of 4 immunizations. Mice were monitored for tumor growth and survival. FIG. 5F depicts the quantification of invasion depth in mm from H&E images of tumor tissue harvested from pVax or MAGE-A immunized mice at day 50. For (B), N=11 mice for pVax control group and 16 mice for MAGE-A immunized group. 8 mice from the MAGE-A group were sacrificed for immune analysis on day 50, and the remaining mice were followed for survival (C). Significance for tumor volume measurements over time was determined by multiple t-tests for each time point. Significance for mouse survival was determined by the Gehan-Breslow-Wilcoxon test. *$p<0.05$, $p<0.01$, *$p<0.001$, ****$p<0.0001$. Error bars indicate ±SEM. Scale bar=100 µm.

FIG. 6, comprising FIG. 6A depicts representative images of immunofluorescence staining of melanomas for CD8 (green) T cells and DAPI (blue). FIG. 6D depicts surface staining of tumor infiltrating CD4+ T cells for CD44 and PD1 expression Significance was determined by a student's t-test. *$p<0.05$, $p<0.01$, *$p<0.001$, ****$p<0.0001$. Scale bar=50 µm.

FIG. 7, comprising FIG. 7A depicts a schematic of the immunization schedule. C57Bl/6 mice were immunized 3 times at 2 week intervals and sacrificed 1 week following final vaccination. Mice were immunized with 25 μg of DNA followed by electroporation. FIG. 7B depicts the frequency of human MAGE-A isoform-specific IFNγ spot-forming units (SFU) per million splenocytes isolated from mice immunized with the human MAGE-A consensus #1 vaccine. Mouse splenocytes were stimulated with human MAGE-A consensus #1 peptides matching the vaccine sequence. FIG. 7C depicts the frequency of human MAGE-A isoform-specific IFNγ spot-forming units (SFU) per million splenocytes isolated from mice immunized with the human MAGE-A consensus #1 vaccine. Mouse splenocytes were stimulated with isoform specific peptides matching human MAGE-A2, MAGE-A3, MAGE-A6 or MAGE-A12. FIG. 7D depicts the frequency of human MAGE-A isoform-specific IFNγ spot-forming units (SFU) per million splenocytes isolated from mice immunized with the human MAGE-A consensus #2 vaccine. Mouse splenocytes were stimulated with human MAGE-A consensus #2 peptides matching the vaccine sequence. FIG. 7E depicts the frequency of human MAGE-A isoform-specific IFNγ spot-forming units (SFU) per million splenocytes isolated from mice immunized with the human MAGE-A consensus #2 vaccine. Mouse splenocytes were stimulated isoform specific peptides matching human MAGE-A1, MAGE-A4 or MAGE-A5. n=5 mice per group. Error bars indicate ±SEM.

DETAILED DESCRIPTION

Figures 1A, 1B:
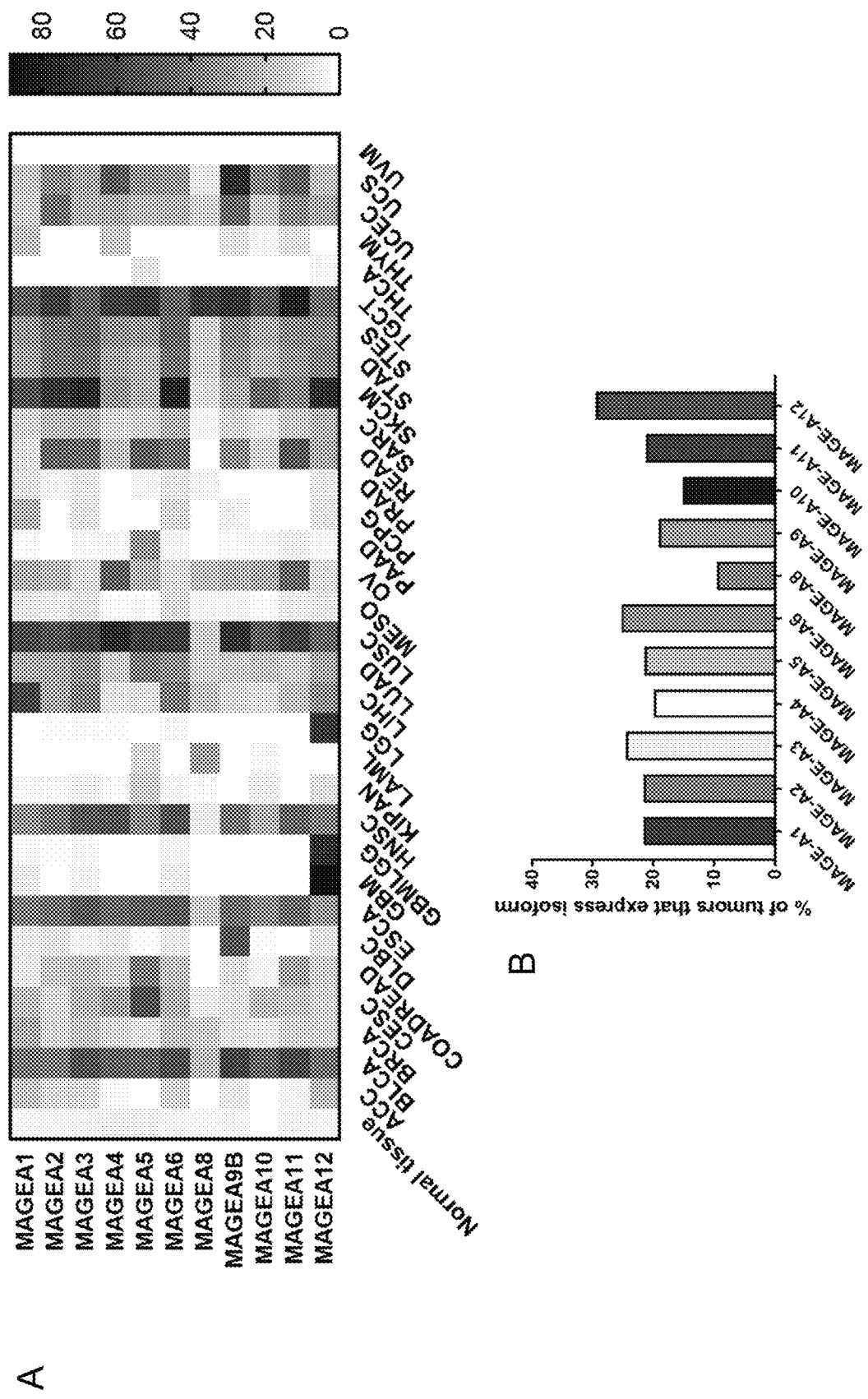
FIG. 1A through FIG. 1C, depicts experimental results demonstrating the expression of MAGE-A isoforms in human tumors.

The present invention is directed to a vaccine for use in treating cancers and tumors in mammals. Antigen consensus sequences have been designed for the cancer related antigen MAGE-A to be used in the vaccine to allow customized vaccine-mediated prevention and treatment of cancers. For example, MAGE-A antigen may be used in the vaccine for prevention or treatment of lung cancers, melanoma, breast cancers, ovarian cancers, and multiple myeloma. The vaccine of the invention can be used along with any combination of additional cancer antigens for the treatment or prevention of a cancer in a subject in need thereof.

One manner for designing the nucleic acid and its encoded amino acid sequence of the recombinant cancer antigen is by introducing mutations that change particular amino acids in the overall amino acid sequence of the native cancer antigen. The introduction of mutations does not alter the cancer antigen so much that it cannot be universally applied across a mammalian, but changes it enough that the resulting amino acid sequence breaks tolerance or is considered a foreign antigen in order to generate an immune response. Another manner may be creating a consensus recombinant cancer antigen that has at least 85% and up to 99% amino acid sequence identity to its corresponding native cancer antigen; at least 90% and up to 98% sequence identity; at least 93% and up to 98% sequence identity; or at least 95% and up to 98% sequence identity. In some instances the recombinant cancer antigen has 95%, 96%, 97%, 98%, or 99% amino acid sequence identity to its corresponding native cancer antigen. The native cancer antigen is the antigen normally associated with the particular cancer or cancer tumor (e.g., native MAGE-A). Depending upon the cancer antigen, the consensus sequence of the cancer antigen can be across mammalian species. Some cancer antigens do not vary greatly from the wild type amino acid sequence of the cancer antigen. Some cancer antigens have nucleic acid/amino acid sequences that are so divergent across species, that a consensus sequence cannot be generated. In these instances, a recombinant cancer antigen that will break tolerance and generate an immune response is generated that has at least 85% and up to 99% amino acid sequence identity to its corresponding native cancer antigen; at least 90% and up to 98% sequence identity; at least 93% and up to 98% sequence identity; or at least 95% and up to 98% sequence identity. In some instances the recombinant cancer antigen has up to 95%, 96%, 97%, 98%, or 99% amino acid sequence identity to its corresponding native cancer antigen. In some embodiments, the consensus sequence of the cancer antigen can be isoforms (e.g. MAGE-A isoforms). Some cancer antigens do not vary greatly from the wild type amino acid sequence of the cancer antigen. Some cancer antigens have nucleic acid/amino acid sequences that are so divergent across isoforms, that a consensus sequence cannot be generated. In these instances, a recombinant cancer antigen that will break tolerance and generate an immune response is generated that has at least 85% and up to 99% amino acid sequence identity to its corresponding native cancer antigen; at least 90% and up to 98% sequence identity; at least 93% and up to 98% sequence identity; or at least 95% and up to 98% sequence identity. In some instances, the recombinant cancer antigen has up to 95%, 96%, 97%, 98%, or 99% amino acid sequence identity to its corresponding native cancer antigen.

The recombinant cancer antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune response. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, factors that down regulate MEW presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule.

The vaccine may be combined further with antibodies to checkpoint molecules, including but not limited to PD-1, PDL-1, TIM3, LAG3 and CTLA4 to increase the stimulation of both the cellular and humoral immune responses. Using anti-checkpoint molecule antibodies prevents the immune checkpoint from suppressing T-cell and/or B-cell responses. Overall, by designing the cancer antigens to be recognized by the immune system helps to overcome other forms of immune suppression by tumor cells, and these vaccines can be used in combination with suppression or inhibition therapies (such as anti-PD-1, anti-PDL-1, anti-TIM3, anti-LAG3 and anti-CTLA4 antibody therapies) to further increase T-cell and/or B-cell responses.

1. DEFINITIONS

Unless otherwise defined, all technical and scientific terms used herein have the same meaning as commonly understood by one of ordinary skill in the art. In case of conflict, the present document, including definitions, will control. Exemplary methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting. The terminology used herein is for the purpose of describing particular embodiments only and is not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

"Adjuvant" as used herein means any molecule added to the DNA plasmid vaccines described herein to enhance the immunogenicity of the antigens encoded by the DNA plasmids and the encoding nucleic acid sequences described hereinafter.

"Antibody" as used herein means an antibody of classes IgG, IgM, IgA, IgD or IgE, or fragments, or derivatives thereof, including Fab, F(ab')2, Fd, and single chain antibodies, diabodies, bispecific antibodies, bifunctional antibodies and derivatives thereof. The antibody can be an antibody isolated from the serum sample of mammal, a polyclonal antibody, affinity purified antibody, or mixtures thereof which exhibits sufficient binding specificity to a desired epitope or a sequence derived therefrom.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered.

"Complement" or "complementary" as used herein means a nucleic acid can mean Watson-Crick (e.g., A-T/U and C-G) or Hoogsteen base pairing between nucleotides or nucleotide analogs of nucleic acid molecules.

"Consensus" or "consensus sequence" as used herein means a polypeptide sequence based on analysis of an alignment of multiple sequences for the same gene from different organisms. Nucleic acid sequences that encode a consensus polypeptide sequence can be prepared. Vaccines comprising proteins that comprise consensus sequences and/or nucleic acid molecules that encode such proteins can be used to induce broad immunity against an antigen.

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Fragment" as used herein with respect to nucleic acid sequences means a nucleic acid sequence or a portion thereof, that encodes a polypeptide capable of eliciting an immune response in a mammal that cross reacts with an antigen disclosed herein. The fragments can be DNA fragments selected from at least one of the various nucleotide sequences that encode protein fragments set forth below. Fragments can comprise at least 10%, at least 20%, at least 30%, at least 40%, at least 50%, at least 60%, at least 70%, at least 80%, at least 90%, or at least 95% of one or more of the nucleic acid sequences set forth below. In some embodiments, fragments can comprise at least 20 nucleotides or more, at least 30 nucleotides or more, at least 40 nucleotides or more, at least 50 nucleotides or more, at least 60 nucleotides or more, at least 70 nucleotides or more, at least 80 nucleotides or more, at least 90 nucleotides or more, at least 100 nucleotides or more, at least 150 nucleotides or more, at least 200 nucleotides or more, at least 250 nucleotides or more, at least 300 nucleotides or more, at least 350 nucleotides or more, at least 400 nucleotides or more, at least 450 nucleotides or more, at least 500 nucleotides or more, at least 550 nucleotides or more, at least 600 nucleotides or more, at least 650 nucleotides or more, at least 700 nucleotides or more, at least 750 nucleotides or more, at least 800 nucleotides or more, at least 850 nucleotides or more, at least 900 nucleotides or more, at least 950 nucleotides or more, or at least 1000 nucleotides or more of at least one of the nucleic acid sequences set forth below.

"Fragment" or "immunogenic fragment" with respect to polypeptide sequences means a polypeptide capable of eliciting an immune response in a mammal that cross reacts with an antigen disclosed herein. The fragments can be polypeptide fragments selected from at least one of the various amino acids sequences below. Fragments of consensus proteins can comprise at least 10%, at least 20%, at least 30%, at least 40%, at least 50%, at least 60%, at least 70%, at least 80%, at least 90% or at least 95% of a consensus protein. In some embodiments, fragments of consensus proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more of a protein sequence disclosed herein.

As used herein, the term "genetic construct" refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operably linked to a coding sequence that encodes a protein such that when present in the cell of the individual, the coding sequence will be expressed.

The term "homology," as used herein, refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous." When used in reference to a double-stranded nucleic acid sequence such as a cDNA or genomic clone, the term "substantially homologous," as used herein, refers to a probe that can hybridize to a strand of the double-stranded nucleic acid sequence under conditions of low stringency. When used in reference to a single-stranded nucleic acid sequence, the term "substantially homologous," as used herein, refers to a probe that can hybridize to (i.e., is the complement of) the single-stranded nucleic acid template sequence under conditions of low stringency.

"Identical" or "identity" as used herein in the context of two or more nucleic acids or polypeptide sequences means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Immune response" as used herein means the activation of a host's immune system, e.g., that of a mammal, in response to the introduction of antigen. The immune response can be in the form of a cellular or humoral response, or both.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively, or differentially with respect to the cell, tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein may facilitate secretion of the protein from the cell in which it is produced. Signal peptides/leader sequences are often cleaved from the remainder of the protein, often referred to as the mature protein, upon secretion from the cell. Signal peptides/leader sequences are linked at the amino terminus (i.e., N terminus) of the protein.

"Stringent hybridization conditions" as used herein means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5-10° C. lower than the thermal melting point (Tm) for the specific sequence at a defined ionic strength pH. The Tm can be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" as used herein can mean a mammal that is capable of being immunized with the vaccines described herein. The mammal can be, for example, a human, chimpanzee, dog, cat, horse, cow, mouse, or rat.

"Substantially complementary" as used herein means that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

"Substantially identical" as used herein means that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

"Treatment" or "treating" as used herein can mean protecting an animal from a disease through means of preventing, suppressing, repressing, or completely eliminating the disease. Preventing the disease involves administering a vaccine of the present invention to an animal prior to onset of the disease. Suppressing the disease involves administering a vaccine of the present invention to an animal after induction of the disease but before its clinical appearance. Repressing the disease involves administering a vaccine of the present invention to an animal after clinical appearance of the disease.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequence substantially identical thereto.

"Variant" with respect to a peptide or polypeptide refers to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art, for example, see Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full-length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full-length of the gene sequence or a fragment thereof. A variant may be an amino acid sequence that is substantially identical over the full-length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full-length of the amino acid sequence or a fragment thereof.

"Vector" as used herein means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and for example, may be a DNA plasmid. The vector can contain or include one or more heterologous nucleic acid sequences.

2. VACCINE

The present invention is directed to an anti-cancer vaccine. The vaccine can comprise MAGE-A alone or in combination with one or more cancer antigens. The vaccine can prevent tumor growth. The vaccine can reduce tumor growth. The vaccine can prevent metastasis of tumor cells. The vaccine can be targeted to treat blood cancers, liver cancer, prostate cancer, melanomas, head and neck cancer, glioblastoma, recurrent respiratory papillomatosis, anal cancer, cervical cancer, and brain cancer.

In one embodiment, the vaccine comprises a synthetic consensus MAGE-A antigen that is recognized by the immune system and breaks tolerance to a self-antigen. The MAGE-A antigen identified is modified from a self-antigen in order to be recognized by the immune system as a foreign antigen, while retaining sufficient similarity to the self-antigen to promote an immune response against the self-antigen. The redesign of the nucleic acid and amino acid sequence of the recombinant cancer antigen from a self to a foreign antigen breaks tolerance of antigen by the immune system. In order to break tolerance, several redesign measures can be applied to the cancer antigen as described below.

The synthetic consensus MAGE-A antigen of the vaccine is not recognized as self, and therefore can break tolerance. The breaking of tolerance can induce antigen-specific T cell and/or high titer antibody responses, thereby inducing or eliciting an immune response that is directed to or reactive against the cancer or tumor expressing native MAGE-A. In some embodiments, the induced or elicited immune response can be a cellular, humoral, or both cellular and humoral immune response. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate WIC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule.

In a particular embodiment, the vaccine can mediate clearance or prevent growth of tumor cells by inducing (1) humoral immunity via B cell responses to generate antibodies that block monocyte chemoattractant protein-1 (MCP-1) production, thereby retarding myeloid derived suppressor cells (MDSCs) and suppressing tumor growth; (2) increase cytotoxic T lymphocyte such as $CD8^+$ (CTL) to attack and kill tumor cells; (3) increase T helper cell responses; (4) and increase inflammatory responses via IFN-γ and TNF-α or all of the aforementioned. The vaccine can increase tumor free survival by at least 1%, 5%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, or more than 45% relative to tumor free survival in the absence of the vaccine. The vaccine can reduce tumor mass by at least 1%, 5%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60% or more than 60% after immunization relative to the tumor mass prior to immunization. The vaccine can prevent and block increases in monocyte chemoattractant protein 1 (MCP-1), a cytokine secreted by myeloid derived suppressor cells. The vaccine can increase survival by at least 1%, 5%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60% or more than 60% after immunization relative to survival in the absence of the vaccine.

The vaccine can increase a cellular immune response in a subject administered the vaccine by about 2-fold to about 6000-fold, about 3-fold to about 6000-fold, about 4-fold to about 6000-fold, about 5-fold to about 6000-fold, about 6-fold to about 6000-fold, about 7-fold to about 6000-fold, about 8-fold to about 6000-fold, about 9-fold to about 6000-fold, about 10-fold to about 6000-fold, about 15-fold to about 6000-fold, about 10-fold to about 6000-fold, about 25-fold to about 6000-fold, about 30-fold to about 6000-fold, about 35-fold to about 6000-fold, about 40-fold to about 6000-fold, about 45-fold to about 6000-fold, about 50-fold to about 6000-fold, about 2-fold to about 5500-fold, about 2-fold to about 5000-fold, about 2-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to a cellular immune response in a subject not administered the vaccine. In some embodiments the vaccine can increase the cellular immune response in the subject administered the vaccine by about 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to the cellular immune response in the subject not administered the vaccine.

The vaccine can increase interferon gamma (IFN-γ) levels in a subject administered the vaccine by about 2-fold to about 6000-fold, about 3-fold to about 6000-fold, about 4-fold to about 6000-fold, about 5-fold to about 6000-fold, about 6-fold to about 6000-fold, about 7-fold to about 6000-fold, about 8-fold to about 6000-fold, about 9-fold to about 6000-fold, about 10-fold to about 6000-fold, about 15-fold to about 6000-fold, about 10-fold to about 6000-fold, about 25-fold to about 6000-fold, about 30-fold to about 6000-fold, about 35-fold to about 6000-fold, about 40-fold to about 6000-fold, about 45-fold to about 6000-fold, 50-fold to about 6000-fold, about 2-fold to about 5500-fold, about 2-fold to about 5000-fold, about 2-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to IFN-γ levels in a subject not administered the vaccine. In some embodiments the vaccine can increase IFN-γ levels in the subject administered the vaccine by about 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to IFN-γ levels in the subject not administered the vaccine.

The vaccine can be a DNA vaccine. DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome.

The vaccine can be an RNA of the one or more cancer antigens. The RNA vaccine can be introduced into the cell.

The vaccine can be an attenuated live vaccine, a vaccine using recombinant vectors to deliver antigen, subunit vaccines, and glycoprotein vaccines, for example, but not limited, the vaccines described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

The vaccine of the present invention can have features required of effective vaccines such as being safe so that the vaccine itself does not cause illness or death; being protective against illness; inducing neutralizing antibody; inducing protective T cell responses; and providing ease of administration, few side effects, biological stability, and low cost per dose. The vaccine can accomplish some or all of these features by comprising the cancer antigen as discussed below.

As described in more detail below, the vaccine can further comprise one or more inhibitors of one or more immune checkpoint molecules (i.e., an immune checkpoint inhibitor). Immune checkpoint molecules are described below in more detail. The immune checkpoint inhibitor may be any nucleic acid or protein that prevents the suppression of any component in the immune system such as MEW class presentation, T cell presentation and/or differentiation, B cell presentation and/or differentiation, any cytokine, chemokine or signaling for immune cell proliferation and/or differentiation. As also described below in more detail, the vaccine may be combined further with one or more antibodies to checkpoint molecules such as PD-1, PDL-1, TIM-3, LAG-3 and CTLA4 to increase the stimulation of both the cellular and humoral immune responses. Using anti-checkpoint molecule antibodies prevents immune checkpoint proteins from suppressing T-cell and/or B-cell responses.

The synthetic consensus antigen can be a nucleic acid sequence, an amino acid sequence, or a combination thereof. The at least one cancer antigen can be a nucleic acid sequence, an amino acid sequence, or a combination thereof. The nucleic acid sequence can be DNA, RNA, cDNA, a variant thereof, a fragment thereof, or a combination thereof. The nucleic acid sequence can also include additional sequences that encode linker or tag sequences that are linked to the antigen by a peptide bond. The amino acid sequence can be a protein, a peptide, a variant thereof, a fragment thereof, or a combination thereof. The cancer antigen can be a recombinant cancer antigen.

One manner for designing the nucleic acid and its encoded amino acid sequence of the recombinant cancer antigen is by introducing mutations that change particular amino acids in the overall amino acid sequence of the native cancer antigen. The introduction of mutations does not alter the cancer antigen so much that it cannot be universally applied across a mammalian subject but changes it enough that the resulting amino acid sequence breaks tolerance or is considered a foreign antigen in order to generate an immune response. Another manner may be creating a consensus recombinant cancer antigen that has at least 85% and up to 99% amino acid sequence identity to its corresponding native cancer antigen; at least 90% and up to 98% sequence identity; at least 93% and up to 98% sequence identity; or at least 95% and up to 98% sequence identity. In some instances the recombinant cancer antigen is 95%, 96%, 97%, 98%, or 99% amino acid sequence identity to its corresponding native cancer antigen. The native cancer antigen is the antigen normally associated with the particular cancer or cancer tumor. Depending upon the cancer antigen, the consensus sequence of the cancer antigen can be across mammalian species or within subtypes of a species or across viral strains or serotypes or across isotypes of an antigen. Some cancer antigens do not vary greatly from the wild type amino acid sequence of the cancer antigen. Some cancer antigens have nucleic acid/amino acid sequences that are so divergent across species or isotypes, that a consensus sequence cannot be generated. In these instances, a recombinant cancer antigen that will break tolerance and generate an immune response is generated that has at least 85% and up to 99% amino acid sequence identity to its corresponding native cancer antigen; preferably at least 90% and up to 98% sequence identity; more preferably at least 93% and up to 98% sequence identity; or even more preferably at least 95% and up to 98% sequence identity. In some instances the recombinant cancer antigen is 95%, 96%, 97%, 98%, or 99% amino acid sequence identity to its corresponding native cancer antigen. The aforementioned approaches can be combined so that the final recombinant cancer antigen has a percent similarity to native cancer antigen amino acid sequence as discussed, above.

a. Melanoma-Associated Antigen-A Antigen

The vaccine of the present invention can comprise the cancer antigen MAGE-A, a fragment thereof, or a variant thereof. Melanoma-associated Antigen-A (MAGE-A) family of proteins includes of twelve homologous proteins MAGE-A1, MAGE-A2, MAGE-A3, MAGE-A4, MAGE-A5, MAGE-A6, MAGE-A7, MAGE-A8, MAGE-A9, MAGE-A10, MAGE-A11, and MAGE-A12. The MAGE-A proteins are cancer testis antigens (CTA), which are expressed only in tumor cells and non-MHC expressing germ cells of the testis and placenta. MAGE-A proteins are expressed in a variety of human cancers including, but not limited to, melanoma, breast cancer, leukemia, thyroid cancer, gastric cancer, pancreatic cancer, liver cancer (e.g., hepatocellular carcinoma), lung cancer (e.g., non-small cell lung carcinoma), ovarian cancer, multiple myeloma, esophageal cancer, kidney cancer, head cancers (e.g., squamous cell carcinoma), neck cancers (e.g., squamous cell carcinoma), prostate cancer, synovial cell sarcoma, and urothelial cancer.

The MAGE-A antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune response. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The MAGE-A antigen can comprise protein epitopes that make them particularly effective as immunogens against which anti-MAGE-A immune responses can be induced. The MAGE-A antigen can comprise the full-length translation product, a variant thereof, a fragment thereof or a combination thereof. The MAGE-A antigen can comprise a consensus protein.

The nucleic acid sequence encoding the MAGE-A antigen or consensus MAGE-A antigen can be optimized with regards to codon usage and corresponding RNA transcripts. The nucleic acid encoding the MAGE-A antigen or consensus MAGE-A antigen can be codon and RNA optimized for expression in mammals, for example in humans. In some embodiments, the nucleic acid sequence encoding the MAGE-A antigen or consensus MAGE-A antigen can include a Kozak sequence to increase the efficiency of translation. The nucleic acid encoding the MAGE-A antigen or consensus MAGE-A antigen can include or be operably linked to one or multiple stop codons (e.g., encoded by a sequence such as TGA or TGATAA) to increase the efficiency of translation termination.

The nucleic acid encoding the MAGE-A antigen or consensus MAGE-A antigen can also encode an immunoglobulin E (IgE) leader sequence. The nucleic acid encoding the MAGE-A antigen or consensus MAGE-A antigen can further encode the IgE leader sequence such that the amino acid sequence of the IgE leader sequence is linked to the amino acid sequence of the MAGE-A antigen or consensus MAGE-A antigen by a peptide bond, respectively. In one embodiment, an amino acid sequences of consensus MAGE-A antigens operably linked to an IgE leader sequence is set forth in SEQ ID NOs:3, 7 and 11. The nucleic acid encoding the MAGE-A antigen or consensus MAGE-A antigen can also include a nucleotide sequence encoding the IgE leader sequence. In one embodiment, nucleotide sequences encoding a consensus MAGE-A antigens operably linked to a sequence encoding an IgE leader sequence are set forth in SEQ ID NO:4, 8 and 12. In some embodiments, the nucleic acid encoding the MAGE-A antigen or consensus MAGE-A antigen is free of or does not contain a nucleotide sequence encoding the IgE leader sequence. In one embodiment, a nucleotide sequence encoding a consensus MAGE-A antigen that does not contain a nucleotide sequence encoding the IgE leader sequence is set forth in SEQ ID NOs: 2, 6, and 10, and encodes a MAGE-A antigens as set forth in SEQ ID NOs:1, 5 and 9.

In one embodiment, the nucleotide sequence encoding any component of a composition of the present invention may comprise an RNA sequence. For example, in one embodiment, the nucleotide sequence comprises an RNA sequence transcribed by the DNA sequence of SEQ ID NOs: 2, 4, 6, 8, 10, 12, or a variant thereof or a fragment thereof. In another embodiment, the nucleotide sequence comprises an RNA sequence transcribed by a DNA sequence encoding the polypeptide sequence of SEQ ID NOs: 1, 3, 5, 7, 9, 11, or a variant thereof or a fragment thereof.

In some embodiments, the nucleic acid encoding the MAGE-A antigen or consensus MAGE-A antigen can be a heterologous nucleic acid sequence and/or contain one or more heterologous nucleic acid sequences. The nucleic acid encoding the MAGE-A antigen or consensus MAGE-A antigen can be mutated relative to the wild-type MAGE-A antigen such that one or more amino acids or residues in the amino acid sequence of the MAGE-A antigen or consensus MAGE-A antigen, respectively, is replaced or substituted with another amino acid or residue. The nucleic acid encoding the MAGE-A antigen or consensus MAGE-A antigen can be mutated relative to the wild-type MAGE-A antigen such that one or more residues in the amino acid sequence of the MAGE-A antigen or consensus MAGE-A antigen, respectively, are replaced or substituted with another residue, thereby causing the immune system to no longer be tolerant of MAGE-A in the mammal administered the nucleic acid encoding the MAGE-A antigen or consensus MAGE-A antigen, the MAGE-A antigen or consensus MAGE-A antigen, or combinations thereof.

In one aspect, a MAGE-A antigen can comprise the amino acid sequence of SEQ ID NO: 1, which is encoded by the nucleic acid sequence SEQ ID NO:2. SEQ ID NO:3 comprises a MAGE-A protein linked to an IgE leader sequence. SEQ ID NO:4 encodes the MAGE-A protein linked to an IgE leader sequence. The MAGE-A protein can be linked to the IgE leader sequence and an HA tag. In other embodiments, the MAGE-A protein can be free of or not linked to an IgE leader sequence and/or an HA tag. In one embodiment, the MAGE-A antigen is a human MAGE-A consensus antigen. In one embodiment, the MAGE-A consensus antigen is derived from human MAGEA1, MAGEA4, and MAGEA5.

In one aspect, a MAGE-A antigen can comprise the amino acid sequence of SEQ ID NO: 5, which is encoded by the nucleic acid sequence SEQ ID NO:6. SEQ ID NO:7 comprises a MAGE-A protein linked to an IgE leader sequence. SEQ ID NO:8 encodes the MAGE-A protein linked to an IgE leader sequence. The MAGE-A protein can be linked to the IgE leader sequence and an HA tag. In other embodiments, the MAGE-A protein can be free of or not linked to an IgE leader sequence and/or an HA tag. In one embodiment, the MAGE-A antigen is a human MAGE-A consensus antigen. In one embodiment, the MAGE-A consensus antigen is derived from human MAGEA2, MAGEA2b, MAGEA3, MAGEA6, and MAGEA12.

In one aspect, a MAGE-A antigen can comprise the amino acid sequence of SEQ ID NO: 9, which is encoded by the nucleic acid sequence SEQ ID NO:10. SEQ ID NO:11 comprises a MAGE-A protein linked to an IgE leader sequence. SEQ ID NO:12 encodes the MAGE-A protein linked to an IgE leader sequence. The MAGE-A protein can be linked to the IgE leader sequence and an HA tag. In other embodiments, the MAGE-A protein can be free of or not linked to an IgE leader sequence and/or an HA tag. In one embodiment, the MAGE-A antigen is a mouse MAGE-A consensus antigen. In one embodiment, the MAGE-A consensus antigen is derived from mouse MAGEA1, MAGEA2, MAGEA3, MAGEA5, MAGEA6, and MAGEA8.

In some embodiments, the MAGE-A antigen can be encoded by a nucleic acid sequence encoding a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino sequence set forth in the SEQ ID NO:1. In some embodiments, the MAGE-A antigen can be encoded by a nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:2. In some embodiments, the MAGE-A antigen can be encoded an RNA encoded by a DNA sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:2. In some embodiments, the MAGE-A antigen can be encoded by an RNA that encodes an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:1. The MAGE-A antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:1.

In some embodiments, the MAGE-A antigen can be encoded by a nucleic acid sequence encoding a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino sequence set forth in the SEQ ID NO:3. In some embodiments, the MAGE-A antigen can be encoded by a nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:4. In some embodiments, the MAGE-A antigen can be encoded an RNA encoded by a DNA sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:4. In some embodiments, the MAGE-A antigen can be encoded by an RNA that encodes an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:3. The MAGE-A antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:3.

In some embodiments, the MAGE-A antigen can be encoded by a nucleic acid sequence encoding a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino sequence set forth in the SEQ ID NO:5. In some embodiments, the MAGE-A antigen can be encoded by a nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:6. In some embodiments, the MAGE-A antigen can be encoded an RNA encoded by a DNA sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:6. In some embodiments, the MAGE-A antigen can be encoded by an RNA that encodes an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:5. The MAGE-A antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:5.

In some embodiments, the MAGE-A antigen can be encoded by a nucleic acid sequence encoding a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino sequence set forth in the SEQ ID NO:7. In some embodiments, the MAGE-A antigen can be encoded by a nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:8. In some embodiments, the MAGE-A antigen can be encoded an RNA encoded by a DNA sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:8. In some embodiments, the MAGE-A antigen can be encoded by an RNA that encodes an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:7. The MAGE-A antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:7.

In some embodiments, the MAGE-A antigen can be encoded by a nucleic acid sequence encoding a protein having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino sequence set forth in the SEQ ID NO:9. In some embodiments, the MAGE-A antigen can be encoded by a nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:10. In some embodiments, the MAGE-A antigen can be encoded an RNA encoded by a DNA sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NO:10. In some embodiments, the MAGE-A antigen can be encoded by an RNA that encodes an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:9. The MAGE-A antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:9

Some embodiments relate to nucleic acid sequences encoding proteins homologous to the MAGE-A protein, an immunogenic fragment of the MAGE-A protein, and immunogenic fragments of homologous proteins. Such nucleic acid molecules that encode immunogenic proteins that have at least 95% homology to a sequence, at least 96% homology to a sequence, at least 97% homology to a sequence, at least 98% homology to a sequence and at least 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have at least 95% homology to the nucleic acid coding sequences herein. Some embodiments relate to nucleic acid molecules that encode immunogenic proteins that have at least 96% homology to the nucleic acid coding sequences herein. Some embodiments relate to nucleic acid molecules that encode immunogenic proteins that have at least 97% homology to the nucleic acid coding sequences herein. Some embodiments relate to nucleic acid molecules that encode immunogenic proteins that have at least 98% homology to the nucleic acid coding sequences herein. Some embodiments relate to nucleic acid molecules that encode immunogenic proteins that have at least 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full-length MAGE-A protein, immunogenic fragment of the MAGE-A protein, and immunogenic fragments of proteins having identity to the MAGE-A protein. Such nucleic acid molecules that encode immunogenic proteins that have at least 80% identity to a full-length MAGE-A sequence, at least 85% identity to a full-length sequence, at least 90% identity to a full-length MAGE-A sequence, at least 91% identity to a full-length MAGE-A sequence, at least 92% identity to a full-length MAGE-A sequence, at least 93% identity to a full-length MAGE-A sequence, at least 94% identity to a full-length MAGE-A sequence, at least 95% identity to a full-length MAGE-A sequence, at least 96% identity to a full-length MAGE-A sequence, at least 97% identity to a full-length MAGE-A sequence, at least 98% identity to a full-length MAGE-A sequence, and at least 99% identity to a full-length MAGE-A sequence can be provided. Likewise, nucleic acid sequences encoding the immunogenic fragments set forth herein and the immunogenic fragments of proteins with similar percent identities as indicated above to the MAGE-A antigens set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NOs:2, 4, 6, 8, 10 or 12. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NOs:2, 4, 6, 8, 10 or 12. Fragments can be at least 95%, at least 96%, at least 97%, at least 98%, or at least 99% homologous to fragments of SEQ ID NOs:2, 4, 6, 8, 10 or 12. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NOs:2, 4, 6, 8, 10 or 12. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, in one embodiment, the amino acid sequence of the MAGE-A protein can comprise one of SEQ ID NOs:1, 3, 5, 7, 9, or 11. In one embodiment, the amino acid sequence of the MAGE-A protein linked to an IgE leader comprises SEQ ID NOs:3, 7, or 11. The amino acid sequence of the MAGE-A protein linked to the IgE leader may be linked to an HA tag.

Some embodiments relate to proteins that are homologous to SEQ ID NO:1. Some embodiments relate to immunogenic proteins that have at least 95% homology to the protein sequences as set forth in SEQ ID NO:1. Some embodiments relate to immunogenic proteins that have at least 96% homology to the protein sequences as set forth in SEQ ID NO:1. Some embodiments relate to immunogenic proteins that have at least 97% homology to the protein sequences as set forth in SEQ ID NO:1. Some embodiments relate to immunogenic proteins that have at least 98% homology to the protein sequences as set forth in SEQ ID NO:1. Some embodiments relate to immunogenic proteins that have at least 99% homology to the protein sequences as set forth in SEQ ID NO:1.

Some embodiments relate to proteins that are homologous to SEQ ID NO:3. Some embodiments relate to immunogenic proteins that have at least 95% homology to the protein sequences as set forth in SEQ ID NO:3. Some embodiments relate to immunogenic proteins that have at least 96% homology to the protein sequences as set forth in SEQ ID NO:3. Some embodiments relate to immunogenic proteins that have at least 97% homology to the protein sequences as set forth in SEQ ID NO:3. Some embodiments relate to immunogenic proteins that have at least 98% homology to the protein sequences as set forth in SEQ ID NO:3. Some embodiments relate to immunogenic proteins that have at least 99% homology to the protein sequences as set forth in SEQ ID NO:3.

Some embodiments relate to proteins that are homologous to SEQ ID NO:5. Some embodiments relate to immunogenic proteins that have at least 95% homology to the protein sequences as set forth in SEQ ID NO:5. Some embodiments relate to immunogenic proteins that have at least 96% homology to the protein sequences as set forth in SEQ ID NO:5. Some embodiments relate to immunogenic proteins that have at least 97% homology to the protein sequences as set forth in SEQ ID NO:5. Some embodiments relate to immunogenic proteins that have at least 98% homology to the protein sequences as set forth in SEQ ID NO:5. Some embodiments relate to immunogenic proteins that have at least 99% homology to the protein sequences as set forth in SEQ ID NO:5.

Some embodiments relate to proteins that are homologous to SEQ ID NO:7. Some embodiments relate to immunogenic proteins that have at least 95% homology to the protein sequences as set forth in SEQ ID NO:7. Some embodiments relate to immunogenic proteins that have at least 96% homology to the protein sequences as set forth in SEQ ID NO:7. Some embodiments relate to immunogenic proteins that have at least 97% homology to the protein sequences as set forth in SEQ ID NO:7. Some embodiments relate to immunogenic proteins that have at least 98% homology to the protein sequences as set forth in SEQ ID NO:7. Some embodiments relate to immunogenic proteins that have at least 99% homology to the protein sequences as set forth in SEQ ID NO:7.

Some embodiments relate to proteins that are homologous to SEQ ID NO:9. Some embodiments relate to immunogenic proteins that have at least 95% homology to the protein sequences as set forth in SEQ ID NO:9. Some embodiments relate to immunogenic proteins that have at least 96% homology to the protein sequences as set forth in SEQ ID NO:9. Some embodiments relate to immunogenic proteins that have at least 97% homology to the protein sequences as set forth in SEQ ID NO:9. Some embodiments relate to immunogenic proteins that have at least 98% homology to the protein sequences as set forth in SEQ ID NO:9. Some embodiments relate to immunogenic proteins that have at least 99% homology to the protein sequences as set forth in SEQ ID NO:9.

Some embodiments relate to proteins that are homologous to SEQ ID NO:11. Some embodiments relate to immunogenic proteins that have at least 95% homology to the protein sequences as set forth in SEQ ID NO:11. Some embodiments relate to immunogenic proteins that have at least 96% homology to the protein sequences as set forth in SEQ ID NO:11. Some embodiments relate to immunogenic proteins that have at least 97% homology to the protein sequences as set forth in SEQ ID NO:11. Some embodiments relate to immunogenic proteins that have at least 98% homology to the protein sequences as set forth in SEQ ID NO:11. Some embodiments relate to immunogenic proteins that have at least 99% homology to the protein sequences as set forth in SEQ ID NO:11.

Some embodiments relate to proteins that are identical to SEQ ID NO:1. Some embodiments relate to immunogenic proteins that have an amino acid sequence that is at least 80% identical to the full-length amino acid sequences as set forth in SEQ ID NO:1. Some embodiments relate to immunogenic proteins that have an amino acid sequence that is at least 85% identical to the full-length amino acid sequences as set forth in SEQ ID NO:1. Some embodiments relate to immunogenic proteins that have an amino acid sequence that is at least 90% identical to the full-length amino acid sequences as set forth in SEQ ID NO:1. Some embodiments relate to immunogenic proteins that have an amino acid sequence that is at least 91% identical to the full-length amino acid sequences as set forth in SEQ ID NO:1. Some embodiments relate to immunogenic proteins that have an amino acid sequence that is at least 92% identical to the full-length amino acid sequences as set forth in SEQ ID NO:1. Some embodiments relate to immunogenic proteins that have an amino acid sequence that is at least 93% identical to the full-length amino acid sequences as set forth in SEQ ID NO:1. Some embodiments relate to immunogenic proteins that have an amino acid sequence that is at least 94% identical to the full-length amino acid sequences as set forth in SEQ ID NO:1. Some embodiments relate to immunogenic proteins that have an amino acid sequence that is at least 95% identical to the full-length amino acid sequences as set forth in SEQ ID NO:1. Some embodiments relate to immunogenic proteins that have an amino acid sequence that is at least 96% identical to the full-length amino acid sequences as set forth in SEQ ID NO:1. Some embodiments relate to immunogenic proteins that have an amino acid sequence that is at least 97% identical to the full-length amino acid sequences as set forth in SEQ ID NO:1. Some embodiments relate to immunogenic proteins that have an amino acid sequence that is at least 98% identical to the full-length amino acid sequences as set forth in SEQ ID NO:1. Some embodiments relate to immunogenic proteins that have an amino acid sequence that is at least 99% identical to the full-length amino acid sequences as set forth in SEQ ID NO:1 .

Some embodiments relate to proteins that are identical to SEQ ID NO:5. Some embodiments relate to immunogenic proteins that have an amino acid sequence that is at least 80% identical to the full-length amino acid sequences as set forth in SEQ ID NO:5. Some embodiments relate to immunogenic proteins that have an amino acid sequence that is at least 85% identical to the full-length amino acid sequences as set forth in SEQ ID NO:5. Some embodiments relate to immunogenic proteins that have an amino acid sequence that is at least 90% identical to the full-length amino acid sequences as set forth in SEQ ID NO:5. Some embodiments relate to immunogenic proteins that have an amino acid sequence that is at least 91% identical to the full-length amino acid sequences as set forth in SEQ ID NO:5. Some embodiments relate to immunogenic proteins that have an amino acid sequence that is at least 92% identical to the full-length amino acid sequences as set forth in SEQ ID NO:5. Some embodiments relate to immunogenic proteins that have an amino acid sequence that is at least 93% identical to the full-length amino acid sequences as set forth in SEQ ID NO:5. Some embodiments relate to immunogenic proteins that have an amino acid sequence that is at least 94% identical to the full-length amino acid sequences as set forth in SEQ ID NO:5. Some embodiments relate to immunogenic proteins that have an amino acid sequence that is at least 95% identical to the full-length amino acid sequences as set forth in SEQ ID NO:5. Some embodiments relate to immunogenic proteins that have an amino acid sequence that is at least 96% identical to the full-length amino acid sequences as set forth in SEQ ID NO:5. Some embodiments relate to immunogenic proteins that have an amino acid sequence that is at least 97% identical to the full-length amino acid sequences as set forth in SEQ ID NO:5. Some embodiments relate to immunogenic proteins that have an amino acid sequence that is at least 98% identical to the full-length amino acid sequences as set forth in SEQ ID NO:5. Some embodiments relate to immunogenic proteins that have an amino acid sequence that is at least 99% identical to the full-length amino acid sequences as set forth in SEQ ID NO:5.

Some embodiments relate to proteins that are identical to SEQ ID NO:9. Some embodiments relate to immunogenic proteins that have an amino acid sequence that is at least 80% identical to the full-length amino acid sequences as set forth in SEQ ID NO:9. Some embodiments relate to immunogenic proteins that have an amino acid sequence that is at least 85% identical to the full-length amino acid sequences as set forth in SEQ ID NO:9. Some embodiments relate to immunogenic proteins that have an amino acid sequence that is at least 90% identical to the full-length amino acid sequences as set forth in SEQ ID NO:9. Some embodiments relate to immunogenic proteins that have an amino acid sequence that is at least 91% identical to the full-length amino acid sequences as set forth in SEQ ID NO:9. Some embodiments relate to immunogenic proteins that have an amino acid sequence that is at least 92% identical to the full-length amino acid sequences as set forth in SEQ ID NO:9. Some embodiments relate to immunogenic proteins that have an amino acid sequence that is at least 93% identical to the full-length amino acid sequences as set forth in SEQ ID NO:9. Some embodiments relate to immunogenic proteins that have an amino acid sequence that is at least 94% identical to the full-length amino acid sequences as set forth in SEQ ID NO:9. Some embodiments relate to immunogenic proteins that have an amino acid sequence that is at least 95% identical to the full-length amino acid sequences as set forth in SEQ ID NO:9. Some embodiments relate to immunogenic proteins that have an amino acid sequence that is at least 96% identical to the full-length amino acid sequences as set forth in SEQ ID NO:9. Some embodiments relate to immunogenic proteins that have an amino acid sequence that is at least 97% identical to the full-length amino acid sequences as set forth in SEQ ID NO:9. Some embodiments relate to immunogenic proteins that have an amino acid sequence that is at least 98% identical to the full-length amino acid sequences as set forth in SEQ ID NO:9. Some embodiments relate to immunogenic proteins that have an amino acid sequence that is at least 99% identical to the full-length amino acid sequences as set forth in SEQ ID NO:9.

In some embodiments, the protein is free of a leader sequence. In some embodiments, the protein is free of the IgE leader. In some embodiments, the protein comprises a leader sequence. In some embodiments, the protein comprises an IgE leader. In one embodiment, the IgE leader comprises a sequence of SEQ ID NO:13

Fragments of proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a protein. Immunogenic fragments of SEQ ID NO:1, 3, 5, 7, 9 or 11 can be provided. Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NO:1, 3, 5, 7, 9 or 11. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:1, 3, 5, 7, 9 or 11 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NO:1, 3, 5, 7, 9 or 11. Some embodiments relate to immunogenic fragments that have at least 96% homology to the immunogenic fragments of protein sequences herein. Some embodiments relate to immunogenic fragments that have at least 97% homology to the immunogenic fragments of protein sequences herein. Some embodiments relate to immunogenic fragments that have at least 98% homology to the immunogenic fragments of protein sequences herein. Some embodiments relate to immunogenic fragments that have at least 99% homology to the immunogenic fragments of protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences that are at least 80%, 85%, 90%, 91%, 92%, 93%, 94%, 95%, 96%, 97%, 98%, or 99% identical to immunogenic fragments of SEQ ID NO:1, 3, 5, 7, 9 or 11 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are at least 80%, 85%, 90%, 91%, 92%, 93%, 94%, 95%, 96%, 97%, 98%, or 99% identical to the amino acid sequence set forth in SEQ ID NOs:1, 3, 5, 7, 9 or 11. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, in one embodiment, the signal peptide/leader sequence comprises an N terminal methionine of a protein. In one embodiment, an N-terminal methionine is encoded by a start codon. In one embodiment, a start codon is operably linked to the 5' end of a nucleic acid sequence that encodes the protein.

Fragments of SEQ ID NOs:2, 4, 6, 8, 10, or 12 may comprise at least 30, 45, 60, 75, 90, 120, 150, 180, 210, 240, 270, 300, 360, 420, 480, 540, 600, 660, 720, 780, 840, 900, 960, 1000, or more nucleotides of SEQ ID NOs:2, 4, 6, 8, 10, or 12. In some embodiments, fragments of SEQ ID NOs:2, 4, 6, 8, 10, or 12 may comprise coding sequences for the IgE leader sequences. In some embodiments, fragments of SEQ ID NOs:2, 4, 6, 8, 10, or 12 do not comprise coding sequences for the IgE leader sequences.

Fragments of SEQ ID NOs:2, 4, 6, 8, 10, or 12 may comprise fewer than 60, 75, 90, 120, 150, 180, 210, 240, 270, 300, 360, 420, 480, 540, 600, 660, 720, 780, 840, 900, 960, or fewer than 1000 nucleotides of SEQ ID NOs:2, 4, 6, 8, 10, or 12.

Fragments of SEQ ID NOs:1, 3, 5, 7, 9 or 11 may comprise at least 15, 18, 21, 24, 30, 36, 42, 48, 54, 60, 72, 90, 120, 150, 180, 210, 240, 270, 300, 330 or more amino acids of SEQ ID NOs:1, 3, 5, 7, 9 or 11. In some embodiments, fragments of SEQ ID NOs:1, 3, 5, 7, 9 or 11 may comprise coding sequences for the IgE leader sequences. In some embodiments, fragments of SEQ ID NOs:1, 3, 5, 7, 9 or 11 do not comprise coding sequences for the IgE leader sequences.

Fragments of SEQ ID NOs:1, 3, 5, 7, 9 or 11 may comprise fewer than 24, 30, 36, 42, 48, 54, 60, 72, 90, 120, 150, 180, 210, 240, 270, 300, 330, or fewer than 330 amino acids of SEQ ID NOs:1, 3, 5, 7, 9 or 11.

In one embodiment, the consensus MAGE-A antigen is a synthetic consensus MAGE-A. In certain embodiments, the synthetic consensus MAGE-A comprises 1 or more, 2 or more, 3 or more, 4 or more, 5 or more, 6 or more, 7 or more, 8 or more 9 or more, 10 or more, 15 or more, 20 or more, 30 or more, or 50 or more amino acid mutations relative to the wild-type MAGE-A. For example, the consensus MAGE-A antigen can be encoded the nucleic acid sequence SEQ ID NO:1, 5 or 9, which encodes for the amino acid sequence SEQ ID NO:2, 6 or 8. SEQ ID NOs:3, 7 and 11 encodes the consensus MAGE-A proteins linked to an IgE leader sequence. The consensus MAGE-A protein can be linked to the IgE leader sequence and an HA tag. In other embodiments, the consensus MAGE-A protein can be free of or not linked to an IgE leader sequence and/or an HA tag.

In some embodiments, the consensus MAGE-A antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in the SEQ ID NOs:3, 7 or 11. In other embodiments, the consensus MAGE-A antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NOs:4, 8 or 12. The consensus MAGE-A antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NOs:4, 8 or 12.

Some embodiments relate to nucleic acid sequences encoding proteins homologous to the consensus MAGE-A protein, immunogenic fragment of the consensus MAGE-A protein, and immunogenic fragments of homologous proteins. Such nucleic acid molecules that encode immunogenic proteins that have at least 95% homology to a sequence, at least 96% homology to a sequence, at least 97% homology to a sequence, at least 98% homology to a sequence and at least 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have at least 95% homology to the nucleic acid coding sequences herein. Some embodiments relate to nucleic acid molecules that encode immunogenic proteins that have at least 96% homology to the nucleic acid coding sequences herein. Some embodiments relate to nucleic acid molecules that encode immunogenic proteins that have at least 97% homology to the nucleic acid coding sequences herein. Some embodiments relate to nucleic acid molecules that encode immunogenic proteins that have at least 98% homology to the nucleic acid coding sequences herein. Some embodiments relate to nucleic acid molecules that encode immunogenic proteins that have at least 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full-length consensus MAGE-A protein, immunogenic fragment of the consensus MAGE-A protein, and immunogenic fragments of proteins having identity to the consensus MAGE-A protein. Such nucleic acid molecules that encode immunogenic proteins that have up to 80% identity to a full-length consensus MAGE-A sequence, up to 85% identity to a full-length sequence, up to 90% identity to a full-length consensus MAGE-A sequence, up to 91% identity to a full-length consensus MAGE-A sequence, up to 92% identity to a full-length consensus MAGE-A sequence, up to 93% identity to a full-length consensus MAGE-A sequence, up to 94% identity to a full-length consensus MAGE-A sequence, up to 95% identity to a full-length consensus MAGE-A sequence, up to 96% identity to a full-length consensus MAGE-A sequence, up to 97% identity to a full-length consensus MAGE-A sequence, up to 98% identity to a full-length consensus MAGE-A sequence, and up to 99% identity to a full-length consensus MAGE-A sequence can be provided. Likewise, nucleic acid sequences encoding the immunogenic fragments set forth herein and the immunogenic fragments of proteins with similar percent identities as indicated above to the consensus MAGE-A proteins set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NOs:2, 4, 6, 8, 10 or 12. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of SEQ ID NOs:2, 4, 6, 8, 10 or 12. Fragments can be at least 95%, at least 96%, at least 97%, at least 98%, or at least 99% homologous to fragments of SEQ ID NOs:2, 4, 6, 8, 10 or 12. Fragments can be at least 80%, at least 85%, at least 90% at least 91%, at least 92%, at least 93%, at least 94%, at least 95%, at least 96%, at least 97%, at least 98%, or at least 99% identical to fragments of SEQ ID NOs:2, 4, 6, 8, 10 or 12. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, in one embodiment, the amino acid sequence of the consensus MAGE-A protein is SEQ ID NO:1, 5, or 9. The amino acid sequence of the consensus MAGE-A protein linked to an IgE leader may be SEQ ID NO:3, 7 or 9. The amino acid sequence of the consensus MAGE-A protein linked to the IgE leader may be linked to HA tag.

Some embodiments relate to proteins that are homologous to SEQ ID NOs:1, 3, 5, 7, 9 or 11. Some embodiments relate to immunogenic proteins that have 95% homology to the protein sequences as set forth in SEQ ID NOs:1, 3, 5, 7, 9 or 11. Some embodiments relate to immunogenic proteins that have 96% homology to the protein sequences as set forth in SEQ ID NOs:1, 3, 5, 7, 9 or 11. Some embodiments relate to immunogenic proteins that have 97% homology to the protein sequences as set forth in SEQ ID NOs:1, 3, 5, 7, 9 or 11. Some embodiments relate to immunogenic proteins that have 98% homology to the protein sequences as set forth in SEQ ID NOs:1, 3, 5, 7, 9 or 11. Some embodiments relate to immunogenic proteins that have 99% homology to the protein sequences as set forth in SEQ ID NOs:1, 3, 5, 7, 9 or 11.

Some embodiments relate to proteins that are identical to SEQ ID NOS:1, 3, 5, 7, 9 or 11. Some embodiments relate to immunogenic proteins that have an amino acid sequence that is 80% identical to the full-length amino acid sequences as set forth in SEQ ID NOS:1, 3, 5, 7, 9 or 11. Some embodiments relate to immunogenic proteins that have an amino acid sequence that is 85% identical to the full-length amino acid sequences as set forth in SEQ ID NOS:1, 3, 5, 7, 9 or 11. Some embodiments relate to immunogenic proteins that have an amino acid sequence that is 90% identical to the full-length amino acid sequences as set forth in SEQ ID NOS:1, 3, 5, 7, 9 or 11. Some embodiments relate to immunogenic proteins that have an amino acid sequence that is 91% identical to the full-length amino acid sequences as set forth in SEQ ID NOS:1, 3, 5, 7, 9 or 11. Some embodiments relate to immunogenic proteins that have an amino acid sequence that is 92% identical to the full-length amino acid sequences as set forth in SEQ ID NOS:1, 3, 5, 7, 9 or 11. Some embodiments relate to immunogenic proteins that have an amino acid sequence that is 93% identical to the full-length amino acid sequences as set forth in SEQ ID NOS:1, 3, 5, 7, 9 or 11. Some embodiments relate to immunogenic proteins that have an amino acid sequence that is 94% identical to the full-length amino acid sequences as set forth in SEQ ID NOS:1, 3, 5, 7, 9 or 11. Some embodiments relate to immunogenic proteins that have an amino acid sequence that is 95% identical to the full-length amino acid sequences as set forth in SEQ ID NOS:1, 3, 5, 7, 9 or 11. Some embodiments relate to immunogenic proteins that have an amino acid sequence that is 96% identical to the full-length amino acid sequences as set forth in SEQ ID NOS:1, 3, 5, 7, 9 or 11. Some embodiments relate to immunogenic proteins that have an amino acid sequence that is 97% identical to the full-length amino acid sequences as set forth in SEQ ID NOS:1, 3, 5, 7, 9 or 11. Some embodiments relate to immunogenic proteins that have an amino acid sequence that is 98% identical to the full-length amino acid sequences as set forth in SEQ ID NOS:1, 3, 5, 7, 9 or 11. Some embodiments relate to immunogenic proteins that have an amino acid sequence that is 99% identical to the full-length amino acid sequences as set forth in SEQ ID NOS:1, 3, 5, 7, 9 or 11.

In some embodiments, the protein is free of a leader sequence. In some embodiments, the protein is free of the IgE leader. Fragments of proteins can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of a protein. Immunogenic fragments of SEQ ID NOS:1, 3, 5, 7, 9 or 11 can be provided. Immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of SEQ ID NOS:1, 3, 5, 7, 9 or 11. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NOS:1, 3, 5, 7, 9 or 11 can be provided. Such immunogenic fragments can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% of proteins that are 95% or greater homologous to SEQ ID NOS:1, 3, 5, 7, 9 or 11. Some embodiments relate to immunogenic fragments that have 96% homology to the immunogenic fragments of protein sequences herein. Some embodiments relate to immunogenic fragments that have 97% homology to the immunogenic fragments of protein sequences herein. Some embodiments relate to immunogenic fragments that have 98% homology to the immunogenic fragments of protein sequences herein. Some embodiments relate to immunogenic fragments that have 99% homology to the immunogenic fragments of protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader. In one embodiment, the immunogenic fragment comprises the dominant MAGE-A epitope. In one embodiment, the dominant MAGE-A epitope comprises the sequence FASINKTHPRAYPEK (SEQ ID NO:14) In one embodiment, the dominant MAGE-A epitope comprises the sequence MKVLQFFASINKTHP (SEQ ID NO:15). In one embodiment, the dominant MAGE-A epitope comprises the sequence VLQFFASI (SEQ ID NO:16). In one embodiment, the dominant MAGE-A epitope comprises the sequence KVLQFFASI (SEQ ID NO:17).

Immunogenic fragments of proteins with amino acid sequences identical to immunogenic fragments of SEQ ID NOS:1, 3, 5, 7, 9 or 11 can be provided. Such immunogenic fragments can comprise at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, or 99% identical to the amino acid sequences set forth in SEQ ID NOS:1, 3, 5, 7, 9 or 11. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence that encodes the protein without a signal peptide coding sequence.

Fragments of SEQ ID NOs:2, 4, 6, 8, 10 or 12 may comprise 30 or more nucleotides. In some embodiments, fragments of SEQ ID NOS:2, 4, 6, 8, 10 or 12 may comprise 45 or more nucleotides. In some embodiments, fragments of SEQ ID NOS:2, 4, 6, 8, 10 or 12 may comprise 60 or more nucleotides. In some embodiments, fragments of SEQ ID NOS:2, 4, 6, 8, 10 or 12 may comprise 75 or more nucleotides. In some embodiments, fragments of SEQ ID NOS:2, 4, 6, 8, 10 or 12 may comprise 90 or more nucleotides. In some embodiments, fragments of SEQ ID NOS:2, 4, 6, 8, 10 or 12 may comprise 120 or more nucleotides. In some embodiments, fragments of SEQ ID NOS:2, 4, 6, 8, 10 or 12 may comprise 150 or more nucleotides. In some embodiments, fragments of SEQ ID NOS:2, 4, 6, 8, 10 or 12 may comprise 180 or more nucleotides. In some embodiments, fragments of SEQ ID NOS:2, 4, 6, 8, 10 or 12 may comprise 210 or more nucleotides. In some embodiments, fragments of SEQ ID NOS:2, 4, 6, 8, 10 or 12 may comprise 240 or more nucleotides. In some embodiments, fragments of SEQ ID NOS:2, 4, 6, 8, 10 or 12 may comprise 270 or more nucleotides. In some embodiments, fragments of SEQ ID NOS:2, 4, 6, 8, 10 or 12 may comprise 300 or more nucleotides. In some embodiments, fragments of SEQ ID NOS:2, 4, 6, 8, 10 or 12 may comprise 360 or more nucleotides. In some embodiments, fragments of SEQ ID NOS:2, 4, 6, 8, 10 or 12 may comprise 420 or more nucleotides. In some embodiments, fragments of SEQ ID NOS:2, 4, 6, 8, 10 or 12 may comprise 480 or more nucleotides. In some embodiments, fragments of SEQ ID NOS:2, 4, 6, 8, 10 or 12 may comprise 540 or more nucleotides. In some embodiments, fragments of SEQ ID NOS:2, 4, 6, 8, 10 or 12 may comprise 600 or more nucleotides. In some embodiments, fragments of SEQ ID NOS:2, 4, 6, 8, 10 or 12 may comprise 300 or more nucleotides. In some embodiments, fragments of SEQ ID NOS:2, 4, 6, 8, 10 or 12 may comprise 660 or more nucleotides. In some embodiments, fragments of SEQ ID NOS:2, 4, 6, 8, 10 or 12 may comprise 720 or more nucleotides. In some embodiments, fragments of SEQ ID NOS:2, 4, 6, 8, 10 or 12 may comprise 780 or more nucleotides. In some embodiments, fragments of SEQ ID NOS:2, 4, 6, 8, 10 or 12 may comprise 840 or more nucleotides. In some embodiments, fragments of SEQ ID NOS:2, 4, 6, 8, 10 or 12 may comprise 900 or more nucleotides. In some embodiments, fragments of SEQ ID NOS:2, 4, 6, 8, 10 or 12 may comprise 960 or more nucleotides. In some embodiments, fragments of SEQ ID NOS:2, 4, 6, 8, 10 or 12 may comprise coding sequences for the IgE leader sequence. In some embodiments, fragments of SEQ ID NOS:2, 4, 6, 8, 10 or 12 do not comprise coding sequences for the IgE leader sequence.

Fragments may comprise fewer than 60 nucleotides, in some embodiments fewer than 75 nucleotides, in some embodiments fewer than 90 nucleotides, in some embodiments fewer than 120 nucleotides, in some embodiments fewer than 150 nucleotides, in some embodiments fewer than 180 nucleotides, in some embodiments fewer than 210 nucleotides, in some embodiments fewer than 240 nucleotides, in some embodiments fewer than 270 nucleotides, in some embodiments fewer than 300 nucleotides, in some embodiments fewer than 360 nucleotides, in some embodiments fewer than 420 nucleotides, in some embodiments fewer than 480 nucleotides, in some embodiments fewer than 540 nucleotides, in some embodiments fewer than 600 nucleotides, in some embodiments fewer than 660 nucleotides, in some embodiments fewer than 720 nucleotides, in some embodiments fewer than 780 nucleotides, in some embodiments fewer than 840 nucleotides, in some embodiments fewer than 900 nucleotides, in some embodiments fewer than 960 nucleotides.

Fragments of SEQ ID NOS:1, 3, 5, 7, 9 or 11 may comprise 15 or more amino acids. In some embodiments, fragments of SEQ ID NOS:1, 3, 5, 7, 9 or 11 may comprise 18 or more amino acids. In some embodiments, fragments of SEQ ID NOS:1, 3, 5, 7, 9 or 11 may comprise 21 or more amino acids. In some embodiments, fragments of SEQ ID NOS:1, 3, 5, 7, 9 or 11 may comprise 24 or more amino acids. In some embodiments, fragments of SEQ ID NOS:1, 3, 5, 7, 9 or 11 may comprise 30 or more amino acids. In some embodiments, fragments of SEQ ID NOS:1, 3, 5, 7, 9 or 11 may comprise 36 or more amino acids. In some embodiments, fragments of SEQ ID NOS:1, 3, 5, 7, 9 or 11 may comprise 42 or more amino acids. In some embodiments, fragments of SEQ ID NOS:1, 3, 5, 7, 9 or 11 may comprise 48 or more amino acids. In some embodiments, fragments of SEQ ID NOS:1, 3, 5, 7, 9 or 11 may comprise 54 or more amino acids. In some embodiments, fragments of SEQ ID NOS:1, 3, 5, 7, 9 or 11 may comprise 60 or more amino acids. In some embodiments, fragments of SEQ ID NOS:1, 3, 5, 7, 9 or 11 may comprise 66 or more amino acids. In some embodiments, fragments of SEQ ID NOS:1, 3, 5, 7, 9 or 11 may comprise 72 or more amino acids. In some embodiments, fragments of SEQ ID NOS:1, 3, 5, 7, 9 or 11 may comprise 90 or more amino acids. In some embodiments, fragments of SEQ ID NOS:1, 3, 5, 7, 9 or 11 may comprise 120 or more amino acids. In some embodiments, fragments of SEQ ID NOS:1, 3, 5, 7, 9 or 11 may comprise 150 or more amino acids. In some embodiments, fragments of SEQ ID NOS:1, 3, 5, 7, 9 or 11 may comprise 180 or more amino acids. In some embodiments, fragments of SEQ ID NOS:1, 3, 5, 7, 9 or 11 may comprise 210 or more amino acids. In some embodiments, fragments of SEQ ID NOS:1, 3, 5, 7, 9 or 11 may comprise 240 or more amino acids. In some embodiments, fragments of SEQ ID NOS:1, 3, 5, 7, 9 or 11 may comprise 270 or more amino acids. In some embodiments, fragments of SEQ ID NOS:1, 3, 5, 7, 9 or 11 may comprise 300 or more amino acids. In some embodiments, fragments of SEQ ID NOS:1, 3, 5, 7, 9 or 11 may comprise 330 or more amino acids. In some embodiments, fragments of SEQ ID NOS:1, 3, 5, 7, 9 or 11 may comprise coding sequences for the IgE leader sequences. In some embodiments, fragments of SEQ ID NOS:1, 3, 5, 7, 9 or 11 do not comprise coding sequences for the IgE leader sequences.

Fragments may comprise fewer than 24 amino acids, in some embodiments fewer than 30 amino acids, in some embodiments fewer than 36 amino acids, in some embodiments fewer than 42 amino acids, in some embodiments fewer than 48 amino acids, in some embodiments fewer than 54 amino acids, in some embodiments fewer than 60 amino acids, in some embodiments fewer than 72 amino acids, in some embodiments fewer than 90 amino acids, in some embodiments fewer than 120 amino acids, in some embodiments fewer than 150 amino acids, in some embodiments fewer than 180 amino acids, in some embodiments fewer than 210 amino acids in some embodiments fewer than 240 amino acids, in some embodiments fewer than 260 amino acids, in some embodiments fewer than 290 amino acids, in some embodiments fewer than 320 amino acids, in some embodiments fewer than 330 amino acids.

b. Combination with Tumor Antigen

The vaccine can comprise a synthetic consensus MAGE-A antigen alone or in combination with one or more tumor antigens. In the context of the present invention, "tumor antigen", "cancer antigen" or "hyperproliferative disorder antigen" or "antigen associated with a hyperproliferative disorder," refers to antigens that are common to specific hyperproliferative disorders such as cancer. The antigens discussed herein are merely included by way of example. The list is not intended to be exclusive and further examples will be readily apparent to those of skill in the art.

Tumor antigens are proteins that are produced by tumor cells that elicit an immune response, particularly T-cell mediated immune responses. The selection of the antigen binding moiety of the invention will depend on the particular type of cancer to be treated. Tumor antigens are well known in the art and include, for example, a glioma-associated antigen, carcinoembryonic antigen (CEA), β-human chorionic gonadotropin, alphafetoprotein (AFP), lectin-reactive AFP, thyroglobulin, tyrosinase (TYR), TYRP1, TYRP2, RAGE-1, MN-CA IX, RU1, RU2 (AS), intestinal carboxyl esterase, mut hsp70-2, M-CSF, prostase, prostate-specific antigen (PSA), PAP, NY-ESO-1, NY-ESO-2, LAGE-1a, p53, prostein, PSMA, GHRH, Her2/neu, survivin and telomerase, prostate-carcinoma tumor antigen-1 (PCTA-1), TERT, ELF2M, neutrophil elastase, ephrinB2, CD22, insulin growth factor (IGF)-I, IGF-II, IGF-I receptor and mesothelin.

In one embodiment, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and GP100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

The type of tumor antigen referred to in the invention may also be a tumor-specific antigen (TSA) or a tumor-associated antigen (TAA). A TSA is unique to tumor cells and does not occur on other cells in the body. A TAA is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSA or TAA antigens include the following: Differentiation antigens such as MART-1/MelanA (MART-I), gp100 (Pmel 17), tyrosinase, TYRP1, TYRP2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; and unique tumor antigens resulting from chromosomal translocations; such as BCR-ABL, E2A-PRL, H4-RET, IGH-IGK, and MYL-RAR. Other large, protein-based antigens include TSP-180, MAGE-B, MAGE-C, RAGE, NY-ESO-1, NY-ESO-2, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

The MAGE-A antigen or fragment of variant thereof of the invention can be associated or combined with one or more additional tumor antigen or fragment or variant thereof. By methodology of generating antigens that represent such markers in a way to break tolerance to self, a cancer vaccine can be generated. Such cancer vaccines can optionally include one or more antibodies targeting one or more additional immune checkpoint proteins to enhance the immune response.

Immune suppression can be facilitated by myeloid derived suppressor cells (MDSCs), which are a mixed population of immature macrophages, granulocytes, dendritic cells, and myeloid cells. The myeloid cells can be a heterogenous population of myeloid progenitor cells and immature myeloid cells (IMCs). Markers of MDSCs can include expression of Gr-1 and CD11b (i.e., Gr-1$^+$ and CD11b$^+$ cells).

Circulation of MDSCs can increase due to chronic infection and expansion of MDSC populations can be associated with autoimmunity and inflammation. Particularly, MDSC expansion (or presence in the tumor or cancerous tissue) can facilitate tumor growth and escape from immune detection and/or regulation, and thus, MDSCs can affect immune responses to anticancer vaccines.

MDSCs can be regulated by Regulator of G-protein signaling 2 (Rgs2) and Rgs2 can be highly expressed in MDSCs derived from tumors. Rgs2 can also be widely expressed in a variety of cells, for example, myeloid cells. MDSCs derived from tumor bearing mice can function differently from MDSCs derived from non-tumor bearing mice. One such difference can be the up-regulation of the production of the chemokine MCP-1, which is secreted by MDSCs. MCP-1 can promote cell migration by signaling through CCR2, a G-protein coupled receptor (GPCR) found on monocytes, endothelial cells, and T cells. Accordingly, MCP-1 can cause migration of endothelial cells, thereby promoting vascularization. Blocking MCP-1 via neutralizing antibodies can inhibit angiogenesis, and thus, can lead to decreased tumor metastases and increased survival. As such, MCP-1 can be considered an angiogenic factor. Besides secreting MCP-1, MDSCs can secrete growth factors, thereby further contributing to tumor growth.

The following are some exemplary tumor antigens:
(1) Tyrosinase (Tyr)

The vaccine of the present invention can comprise the cancer antigen tyrosinase (Tyr), a fragment thereof, or a variant thereof. Tyrosinase is a copper-containing enzyme having tyrosine hydroxylase and dopa oxidase catalytic activities that can be found in microorganisms and plant and animal tissues. Specifically, tyrosinase catalyzes the production of melanin and other pigments by the oxidation of phenols such as tyrosine. Mutations in the TYR gene result in oculocutaneous albinism in mammals and non-pathological polymorphisms in the TYR gene contribute to variation in skin pigmentation.

Additionally, in cancer or tumors such as melanoma, tyrosinase can become unregulated, resulting in increased melanin synthesis. Accordingly, tyrosinase can be a cancer antigen associated with melanoma. In subjects suffering from melanoma, tyrosinase can be a target of cytotoxic T cell recognition. In some instances, however, the immune response to the cancer or tumor (including melanoma) can be suppressed, leading to a microenvironment that supports tumor formation and/or growth and thus, disease progression.

In one embodiment, the tyrosinase antigen is a mammalian tyrosinase antigen. In one embodiment, the tyrosinase antigen is a consensus tyrosinase antigen derived from multiple mammalian tyrosinase antigen sequences. In one embodiment, a tyrosinase antigen is operably linked to a signal peptide.

In one embodiment, a tyrosinase antigen can be administered in vectors described herein, and combined with the MAGE-A antigen and optionally one or more antibodies targeting one or more additional immune checkpoint proteins in various vaccination schedules.

The Tyr antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune response. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

As demonstrated herein, the Tyr antigen induces antigen-specific T-cell and high titer antibody responses against cancerous or tumor cells (e.g., melanoma cells). Specifically, the Tyr antigen is an important target for immune mediated clearance by inducing (1) humoral immunity via B cell responses to generate antibodies that block monocyte chemoattractant protein-1 (MCP-1) production, thereby retarding myeloid derived suppressor cells (MDSCs) and suppressing tumor growth; (2) increase cytotoxic T lymphocyte such as CD8$^+$ (CTL) to attack and kill tumor cells; (3) increase T helper cell responses; and (4) increase inflammatory responses via IFN-γ and TNF-α or all of the aforementioned. As such, a protective immune response is provided against tumor formation and tumor growth by vaccines comprising the Tyr antigen (e.g., the consensus Tyr antigen, which is described below in more detail) because these vaccines prevent immune suppression by decreasing the population of MDSCs found within the cancerous or tumor tissue and block vascularization of the cancerous or tumor tissue by reducing production or secretion of MCP-1. Accordingly, any user can design a vaccine of the present invention to include a Tyr antigen to provide broad immunity against tumor formation, metastasis of tumors, and tumor growth.

The Tyr antigen can comprise protein epitopes that make them particularly effective as immunogens against which anti-Tyr immune responses can be induced. The Tyr antigen can comprise the full-length translation product, a variant thereof, a fragment thereof or a combination thereof. The Tyr antigen can comprise a consensus protein.

The nucleic acid sequence encoding the Tyr antigen can be optimized with regards to codon usage and corresponding RNA transcripts. The nucleic acid encoding the Tyr antigen can be codon and RNA optimized for expression in mammals. In some embodiments, the nucleic acid sequence encoding the Tyr antigen can include a Kozak sequence to increase the efficiency of translation. The nucleic acid encoding the consensus Tyr antigen can include multiple stop codons to increase the efficiency of translation termination.

The nucleic acid encoding the Tyr antigen can also encode an immunoglobulin E (IgE) leader sequence. The nucleic acid encoding the consensus Tyr antigen can further encode the IgE leader sequence such that the amino acid sequence of the IgE leader sequence is linked to the amino acid sequence of the Tyr antigen by a peptide bond. The nucleic acid encoding the Tyr antigen can also include a nucleotide sequence encoding the IgE leader sequence. In some embodiments, the nucleic acid encoding the Tyr antigen is free of or does not contain a nucleotide sequence encoding the IgE leader sequence.

(2) Tyrosinase-Related Protein 1 (TYRP1)

The vaccine of the present invention can comprise the cancer antigen tyrosinase-related Protein 1 (TYRP1), a fragment thereof, or a variant thereof. TYRP1, encoded by the TYRP1 gene, is a 75 kDa transmembrane glycoprotein and is expressed in both normal and malignant melanocytes and melanoma cells. Like tyrosinase, TYRP1 contains a motif termed M-box that can bind to the microphtalmia transcription factor (MITF), which plays a central role within the melanocyte in activating pigmentation, cell proliferation and differentiation. TYRP1 may help to stabilize tyrosinase and can form a heterodimer, which may prevent the premature death of melanocytes by attenuating tyrosinase-mediated cytotoxicity.

As described above for tyrosinase, tyrosinase-related protein 1 (TYRP-1) can also be involved in the synthesis of melanin and pigmentary machinery of the melanocyte, and can be recognized by the immune system in subjects suffering from melanoma. Accordingly, TYRP-1 can be an antigen associated with melanoma.

In one embodiment, the TYRP-1 antigen is a mammalian TYRP-1 antigen. In one embodiment, the TYRP-1 antigen is a consensus TYRP-1 antigen derived from multiple mammalian TYRP-1 antigen sequences. In one embodiment, a TYRP-1 antigen is operably linked to a signal peptide.

In one embodiment, a TYRP-1 antigen can be administered in vectors described herein, and combined with the MAGE-A antigen and optionally one or more antibodies targeting one or more additional immune checkpoint proteins in various vaccination schedules.

The TYRP-1 antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune response. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up-regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The TYRP-1 antigen can comprise protein epitopes that make them particularly effective as immunogens against which anti-TYRP-1 immune responses can be induced. The TYRP-1 antigen can comprise the full-length translation product, a variant thereof, a fragment thereof or a combination thereof. The TYRP-1 antigen can comprise a consensus protein.

The nucleic acid sequence encoding the consensus TYRP-1 antigen can be optimized with regards to codon usage and corresponding RNA transcripts. The nucleic acid encoding the consensus TYRP-1 antigen can be codon and RNA optimized for expression in mammals. In some embodiments, the nucleic acid sequence encoding the consensus TYRP-1 antigen can include a Kozak sequence to increase the efficiency of translation. The nucleic acid encoding the consensus TYRP-1 antigen can include one or more stop codons to increase the efficiency of translation termination.

The nucleic acid encoding the consensus TYRP-1 antigen can also encode an immunoglobulin E (IgE) leader sequence. The nucleic acid encoding the consensus TYRP-1 antigen can further encode the IgE leader sequence such that the amino acid sequence of the IgE leader sequence is linked to the amino acid sequence of the consensus TYRP-1 antigen by a peptide bond. The nucleic acid encoding the consensus TYRP-1 antigen can also include a nucleotide sequence encoding the IgE leader sequence. In some embodiments, the nucleic acid encoding the consensus TYRP-1 antigen is free of or does not contain a nucleotide sequence encoding the IgE leader sequence.

As referred to herein with regard to linking a signal peptide or leader sequence to the N terminus of a protein, the signal peptide/leader sequence replaces the N terminal methionine of a protein which is encoded by the start codon of the nucleic acid sequence that encodes the protein without a signal peptide coding sequence.

(3) Tyrosinase-Related Protein 2 (TYRP2)

The vaccine of the present invention can comprise the cancer antigen tyrosinase-related Protein 2 (TYRP2; also known as dopachrome tautomerase (DCT)), a fragment thereof, or a variant thereof. TYRP2/DCT, encoded by the TYRP2/DCT gene, is a protein comprised of 519 amino acids and is expressed in both normal and malignant melanocytes and melanoma cells. TYRP2/DCT is a well-characterized melanocyte-specific enzyme that, in conjunction with tyrosinase and TYRP1, functions in the conversion of L-tyrosine to melanin in melanocytes. DCT specifically catalyzes the tautomerization of the melanin precursors L-dopachrome to 5,6-dihydroindole-2-carboxylic acid (DHICA), which is subsequently oxidized by TYRP1 (as discussed above) to form eumelanin. Studies have shown that TYRP2/DCT may be a mediator of drug resistance in melanoma cells, with specificity for DNA-damaging agents. Since TYRP2/DCT has frequently been reported to be highly expressed in melanomas, this melanocyte-specific enzyme plays an important role contributing to intrinsic resistance phenotype of melanomas to various anticancer DNA-damaging drugs.

As described above for tyrosinase, tyrosinase-related protein 2 (TYRP-2) can also be involved in the synthesis of melanin and recognized by the immune system in subjects suffering from melanoma. Additionally, TYRP-2 can mediate drug resistance in melanoma cells. Accordingly, TYRP-2 can be an antigen associated with melanoma.

In one embodiment, the TYRP-2 antigen is a mammalian TYRP-2 antigen. In one embodiment, the TYRP-2 antigen is a consensus TYRP-2 antigen derived from multiple mammalian TYRP-2 antigen sequences. In one embodiment, a TYRP-2 antigen is operably linked to a signal peptide.

In one embodiment, a TYRP-2 antigen can be administered in vectors described herein, and combined with the MAGE-A antigen and optionally one or more antibodies targeting one or more additional immune checkpoint proteins in various vaccination schedules.

The TYRP-2 antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune response. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The TYRP2 antigen can comprise protein epitopes that make them particularly effective as immunogens against which anti-TYRP2 immune responses can be induced. The TYRP2 antigen can comprise the full-length translation product, a variant thereof, a fragment thereof or a combination thereof. The TYRP2 antigen can comprise a consensus protein.

The nucleic acid sequence encoding the consensus TYRP2 antigen can be optimized with regards to codon usage and corresponding RNA transcripts. The nucleic acid encoding the consensus TYRP2 antigen can be codon and RNA optimized for expression in mammals. In some embodiments, the nucleic acid sequence encoding the consensus TYRP2 antigen can include a Kozak sequence to increase the efficiency of translation. The nucleic acid encoding the consensus TYRP2 antigen can include multiple stop codons to increase the efficiency of translation termination.

The nucleic acid encoding the consensus TYRP2 antigen can also encode an immunoglobulin E (IgE) leader sequence. The nucleic acid encoding the consensus TYRP2 antigen can further encode the IgE leader sequence such that the amino acid sequence of the IgE leader sequence is linked to the amino acid sequence of the consensus TYRP2 antigen by a peptide bond. The nucleic acid encoding the consensus TYRP2 antigen can also include a nucleotide sequence encoding the IgE leader sequence. In some embodiments, the nucleic acid encoding the consensus TYRP2 antigen is free of or does not contain a nucleotide sequence encoding the IgE leader sequence.

As referred to herein with regard to linking a signal peptide or leader sequence to the N terminus of a protein, the signal peptide/leader sequence replaces the N terminal methionine of a protein which is encoded by the start codon of the nucleic acid sequence that encodes the protein without a signal peptide coding sequence.

(4) hTERT

The vaccine of the present invention can comprise the cancer antigen hTERT, a fragment thereof, or a variant thereof hTERT is a human telomerase reverse transcriptase that synthesizes a TTAGGG tag on the end of telomeres to prevent cell death due to chromosomal shortening. Hyperproliferative cells can have abnormally high expression of hTERT. Abnormal expression of hTERT can also occur in hyperproliferative cells infected with HCV and HPV. Thus, immunotherapy for both HPV and HCV may be enhanced by targeting cells that express hTERT at abnormal levels. HPV and HCV antigens are discussed below in more detail. The hTERT cancer antigen can further be defined by U.S. patent application Ser. No. 14/139,660, filed Dec. 23, 2013, which is incorporated by reference in its' entirety.

Additionally, hTERT expression in dendritic cells transfected with hTERT genes can induce CD8$^+$ cytotoxic T cells and elicit CD4$^+$ T cells in an antigen-specific fashion. Therefore, use of hTERT expression within antigen presenting cells (APCs) to delay senescence and sustain their capacity to present the antigen of choice can be used in immunotherapeutic methods such as in the methods described herein.

The hTERT antigen can be associated with or expressed by any number of cancers including, but not limited to, melanoma, prostate cancer, liver cancer, cervical cancer, recurrent respiratory papillomatosis (RRP), anal cancer, head and neck cancer, and blood cancers. Accordingly, the vaccine, when including the hTERT antigen described herein, can be used for treating subjects suffering from any number of cancers including, but not limited to, melanoma, prostate cancer, liver cancer, cervical cancer, recurrent respiratory papillomatosis (RRP), anal cancer, head and neck cancer, and blood cancers.

The hTERT antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

In one embodiment, the hTERT antigen is a consensus hTERT antigen derived from multiple hTERT antigen sequences. In one embodiment, a hTERT antigen is operably linked to a signal peptide.

In one embodiment, an hTERT antigen can be administered in vectors described herein, and combined with the MAGE-A antigen and optionally one or more antibodies targeting one or more additional immune checkpoint proteins in various vaccination schedules.

The hTERT antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune response. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The hTERT antigen can comprise protein epitopes that make them particularly effective as immunogens against which anti-hTERT immune responses can be induced. The hTERT antigen can comprise the full-length translation product, a variant thereof, a fragment thereof or a combination thereof. The hTERT antigen can comprise a consensus protein.

The nucleic acid sequence encoding the consensus hTERT antigen can be optimized with regards to codon usage and corresponding RNA transcripts. The nucleic acid encoding the consensus hTERT antigen can be codon and RNA optimized for expression in mammals. In some embodiments, the nucleic acid sequence encoding the consensus hTERT antigen can include a Kozak sequence to increase the efficiency of translation. The nucleic acid encoding the consensus hTERT antigen can include one or more stop codons to increase the efficiency of translation termination.

The nucleic acid encoding the consensus hTERT antigen can also encode an immunoglobulin E (IgE) leader sequence. The nucleic acid encoding the consensus Tyr antigen can further encode the IgE leader sequence such that the amino acid sequence of the IgE leader sequence is linked to the amino acid sequence of the consensus hTERT antigen by a peptide bond. The nucleic acid encoding the consensus hTERT antigen can also include a nucleotide sequence encoding the IgE leader sequence. In some embodiments, the nucleic acid encoding the consensus hTERT antigen is free of or does not contain a nucleotide sequence encoding the IgE leader sequence.

(5) Growth Hormone Releasing Hormone (GHRH)

The vaccine of the present invention can comprise the cancer antigen growth hormone releasing hormone (GHRH; also known as growth-hormone-releasing factor (GRF or GHRF) or somatocrinin), a fragment thereof, or a variant thereof. GHRH is a 44 amino acid peptide hormone produced in the arcuate nucleus of the hypothalamus. GHRH is secreted by the hypothalamus and stimulates the release of growth hormone, a regulator of growth, metabolism, and body structure, from the pituitary gland. GHRH also stimulates the product of growth hormone. Antagonists of GHRH can inhibit the growth of a variety of cancers, for example, osteosarcomas, glioblastomas, prostate cancer, renal cancer, pancreatic cancer, colorectal cancer, and breast cancer. Accordingly, GHRH can be an antigen associated with a variety of tumors.

In one embodiment, the GHRH antigen is a mammalian GHRH antigen. In one embodiment, the GHRH antigen is a consensus GHRH antigen derived from multiple mammalian GHRH antigen sequences. In one embodiment, a GHRH antigen is operably linked to a signal peptide.

In one embodiment, a GHRH antigen can be administered in vectors described herein, and combined with the MAGE-A antigen and optionally one or more antibodies targeting one or more additional immune checkpoint proteins in various vaccination schedules.

The GHRH antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune response. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The GHRH antigen can comprise protein epitopes that make them particularly effective as immunogens against which anti-GHRH immune responses can be induced. The GHRH antigen can comprise the full-length translation product, a variant thereof, a fragment thereof or a combination thereof. The GHRH antigen can comprise a consensus protein.

The nucleic acid sequence encoding the consensus GHRH antigen can be optimized with regards to codon usage and corresponding RNA transcripts. The nucleic acid encoding the consensus GHRH antigen can be codon and RNA optimized for expression in mammals. In some embodiments, the nucleic acid sequence encoding the consensus GHRH antigen can include a Kozak sequence to increase the efficiency of translation. The nucleic acid encoding the consensus GHRH antigen can include one or more stop codons to increase the efficiency of translation termination.

The nucleic acid encoding the consensus GHRH antigen can also encode an immunoglobulin E (IgE) leader sequence. The nucleic acid encoding the consensus GHRH antigen can further encode the IgE leader sequence such that the amino acid sequence of the IgE leader sequence is linked to the amino acid sequence of the consensus GHRH antigen by a peptide bond. The nucleic acid encoding the consensus GHRH antigen can also include a nucleotide sequence encoding the IgE leader sequence. In some embodiments, the nucleic acid encoding the consensus GHRH antigen is free of or does not contain a nucleotide sequence encoding the IgE leader sequence.

(6) MART-1/Melan-A

The vaccine of the present invention can comprise the cancer antigen MART-1 (also known as Melan-A), a fragment thereof, or a variant thereof. MART-1, encoded by MLANA gene, is a 118-amino acid protein containing a single transmembrane domain and is expressed in most melanoma cells. MART-1 forms a complex with a structural protein and affects its expression, stability, trafficking and processing which is required for melanosome structure and maturation. Accordingly, MART-1 is indispensable for regulating mammalian pigmentation. Defects in melanosome maturation have been linked to susceptibility to cancer. MART-1 may be expressed in numerous cancers, including, but not limited to, melanomas.

In one embodiment, the MART-1 antigen is a mammalian MART-1 antigen. In one embodiment, the MART-1 antigen is a consensus MART-1 antigen derived from multiple mammalian MART-1 antigen sequences. In one embodiment, a MART-1 antigen is operably linked to a signal peptide.

In one embodiment, a MART-1 antigen can be administered in vectors described herein, and combined with the MAGE-A antigen and optionally one or more antibodies targeting one or more additional immune checkpoint proteins in various vaccination schedules.

Melan-A, also known as melanoma antigen recognized by T cells (MART-1) is a melanocyte differentiation antigen and can be found in normal skin, retina, and melanocytes. Melan-A can be associated with the endoplasmic reticulum and melanosomes. Melan-A can be recognized by cytotoxic T cells as an antigen on melanoma cells, but can also be associated with other tumors having melanocytic origin or differentiation (i.e., cells have melanosomes), for example, clear cell sarcoma and melanotic neurofibroma. Accordingly, Melan-A can be an antigen associated with a variety of tumors derived from cells having melanosomes.

In one embodiment, the MELAN-A antigen is a mammalian MELAN-A antigen. In one embodiment, the MELAN-A antigen is a consensus MELAN-A antigen derived from multiple mammalian MELAN-A antigen sequences. In one embodiment, a MELAN-A antigen is operably linked to a signal peptide.

In one embodiment, a MELAN-A antigen can be administered in vectors described herein, and combined with the MAGE-A antigen and optionally one or more antibodies targeting one or more additional immune checkpoint proteins in various vaccination schedules.

The Melan-A antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune response. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The Melan-A antigen can comprise protein epitopes that make them particularly effective as immunogens against which anti-Melan-A immune responses can be induced. The Melan-A antigen can comprise the full-length translation product, a variant thereof, a fragment thereof or a combination thereof. The Melan-A antigen can comprise a consensus protein.

The nucleic acid sequence encoding the consensus Melan-A antigen can be optimized with regards to codon usage and corresponding RNA transcripts. The nucleic acid encoding the consensus Melan-A antigen can be codon and RNA optimized for expression in mammals. In some embodiments, the nucleic acid sequence encoding the consensus Melan-A antigen can include a Kozak sequence to increase the efficiency of translation. The nucleic acid encoding the consensus Melan-A antigen can include one or more stop codons to increase the efficiency of translation termination.

The nucleic acid encoding the consensus Melan-A antigen can also encode an immunoglobulin E (IgE) leader sequence. The nucleic acid encoding the consensus Melan-A antigen can further encode the IgE leader sequence such that the amino acid sequence of the IgE leader sequence is linked to the amino acid sequence of the consensus Melan-A antigen by a peptide bond. The nucleic acid encoding the consensus Melan-A antigen can also include a nucleotide sequence encoding the IgE leader sequence. In some embodiments, the nucleic acid encoding the consensus Melan-A antigen is free of or does not contain a nucleotide sequence encoding the IgE leader sequence.

(7) NY-ESO-1

The vaccine of the present invention can comprise the cancer antigen New York-esophageal cancer-1 (NY-ESO-1; also called CTAG1), a fragment thereof, or a variant thereof. NY-ESO-1, encoded by the CTAG1B gene, is a 180 amino-acid long protein, with a glycine-rich N-terminal region and an extremely hydrophobic C-terminal region. NY-ESO-1 has restricted expression in normal tissues but frequent occurrence in cancer. NY-ESO-1 may be expressed in numerous cancers including, but not limited to, bladder, colorectal, esophagus, gastric, hepatocarcinoma, head and neck, melanoma, non-small cell lung, ovarian, pancreatic, synovial carcinoma and prostate cancers.

Cancer-testis antigen (NY-ESO-1) can be expressed in the testis and ovary. NY-ESO-1 can be associated with a variety of cancers and can induce humoral immune responses. Subjects suffering from cancer or tumors can develop immunogenicity to NY-ESO-1. Accordingly, NY-ESO-1 can be an antigen associated with a variety of tumors.

In one embodiment, the NY-ESO-1 antigen is a mammalian NY-ESO-1 antigen. In one embodiment, the NY-ESO-1 antigen is a consensus NY-ESO-1 antigen derived from multiple mammalian NY-ESO-1 antigen sequences. In one embodiment, a NY-ESO-1 antigen is operably linked to a signal peptide.

In one embodiment, a NY-ESO-1 antigen can be administered in vectors described herein, and combined with the MAGE-A antigen and optionally one or more antibodies targeting one or more additional immune checkpoint proteins in various vaccination schedules.

The NY-ESO-1 antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune response. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TGF-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The NY-ESO-1 antigen can comprise protein epitopes that make them particularly effective as immunogens against which anti-NY-ESO-1 immune responses can be induced. The NY-ESO-1 antigen can comprise the full-length translation product, a variant thereof, a fragment thereof or a combination thereof. The NY-ESO-1 antigen can comprise a consensus protein.

The nucleic acid sequence encoding the consensus NY-ESO-1 antigen can be optimized with regards to codon usage and corresponding RNA transcripts. The nucleic acid encoding the consensus NY-ESO-1 antigen can be codon and RNA optimized for expression in mammals. In some embodiments, the nucleic acid sequence encoding the consensus NY-ESO-1 antigen can include a Kozak sequence to increase the efficiency of translation. The nucleic acid encoding the consensus NY-ESO-1 antigen can include one or more stop codons to increase the efficiency of translation termination.

The nucleic acid encoding the consensus NY-ESO-1 antigen can also encode an immunoglobulin E (IgE) leader sequence. The nucleic acid encoding the consensus NY-ESO-1 antigen can further encode the IgE leader sequence such that the amino acid sequence of the IgE leader sequence is linked to the amino acid sequence of the consensus NY-ESO-1 antigen by a peptide bond. The nucleic acid encoding the consensus NY-ESO-1 antigen can also include a nucleotide sequence encoding the IgE leader sequence. In some embodiments, the nucleic acid encoding the consensus NY-ESO-1 antigen is free of or does not contain a nucleotide sequence encoding the IgE leader sequence.

(8) NY-ESO-2

The vaccine of the present invention can comprise the cancer antigen New York-esophageal cancer-2 (NY-ESO-2; also known as cancer/testis antigen 2, ESO2, and LAGE1), a fragment thereof, or a variant thereof. NY-ESO-2 is an autoimmunogenic tumor antigen that belongs to the ESO/LAGE family of cancer-testis antigens. NY-ESO-2 can be expressed in a variety of cancers including melanoma, breast cancer, bladder cancer and prostate cancer and is normally expressed in testis tissue. Additionally, NY-ESO-2 can be observed in 25-50% of tumor samples of melanomas, non-small-cell lung carcinomas, bladder, prostate and head and neck cancers. The gene encoding NY-ESO-2 also contains an alternative open reading frame that encodes the protein named CAMEL, a tumor antigen that is recognized by melanoma-specific cytotoxic T-lymphocytes.

Similar to NY-ESO-1, NY-ESO-2 can be expressed in the testis and ovary. NY-ESO-2 can also be associated with a variety of cancers and immunogenic in subjects suffering from cancer or tumors. Accordingly, NY-ESO-2 can be an antigen associated with numerous tumors.

In one embodiment, the NY-ESO-2 antigen is a mammalian NY-ESO-2 antigen. In one embodiment, the NY-ESO-2 antigen is a consensus NY-ESO-2 antigen derived from multiple mammalian NY-ESO-2 antigen sequences. In one embodiment, a NY-ESO-2 antigen is operably linked to a signal peptide.

In one embodiment, a NY-ESO-2 antigen can be administered in vectors described herein, and combined with the MAGE-A antigen and optionally one or more antibodies targeting one or more additional immune checkpoint proteins in various vaccination schedules.

The NY-ESO-2 antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune response. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The NY-ESO-2 antigen can comprise protein epitopes that make them particularly effective as immunogens against which anti-NY-ESO-2 immune responses can be induced. The NY-ESO-2 antigen can comprise the full-length translation product, a variant thereof, a fragment thereof or a combination thereof. The NY-ESO-2 antigen can comprise a consensus protein.

The nucleic acid sequence encoding the consensus NY-ESO-2 antigen can be optimized with regards to codon usage and corresponding RNA transcripts. The nucleic acid encoding the consensus NY-ESO-2 antigen can be codon and RNA optimized for expression in mammals. In some embodiments, the nucleic acid sequence encoding the consensus NY-ESO-2 antigen can include a Kozak sequence to increase the efficiency of translation. The nucleic acid encoding the consensus NY-ESO-2 antigen can include one or more stop codons to increase the efficiency of translation termination.

The nucleic acid encoding the consensus NY-ESO-2 antigen can also encode an immunoglobulin E (IgE) leader sequence. The nucleic acid encoding the consensus NY-ESO-2 antigen can further encode the IgE leader sequence such that the amino acid sequence of the IgE leader sequence is linked to the amino acid sequence of the consensus NY-ESO-2 antigen by a peptide bond. The nucleic acid encoding the consensus NY-ESO-2 antigen can also include a nucleotide sequence encoding the IgE leader sequence. In some embodiments, the nucleic acid encoding the consensus NY-ESO-2 antigen is free of or does not contain a nucleotide sequence encoding the IgE leader sequence.

(9) PRAME

The vaccine of the present invention can comprise the cancer antigen PRAME, a fragment thereof, or a variant thereof. PRAME, encoded by the PRAME gene, is a protein comprised of 509 amino acids and is expressed in testis, placenta, endometrium, ovary, adrenals, and in tissues derived from melanoma, lung, kidney, and head and neck carcinomas. PRAME is also expressed in adult and pediatric acute leukemias, and multiple myeloma. PRAME contains an immunogenic nonapeptide able to elicit a cytotoxic response when presented by HLA-A24. Studies show that overexpression of PRAME in cultured cells induces a caspase-independent cell death responsible for a slower proliferation rate. Other studies demonstrate that overexpression of PRAME also confers growth or survival advantages by antagonizing retinoic acid receptor (RAR) signaling, and is causally involved in the tumorigenic process. Interference of RAR signaling leads to a loss in regulating cellular proliferation, development and differentiation.

PRAME can have an expression pattern similar to the cancer-testis antigens MAGE, BAGE, and GAGE, namely expression in the testis. PRAME, however, can be expressed in human melanomas and acute leukemias. PRAME can be recognized by cytolytic T lymphocytes. Accordingly, PRAME can be an antigen associated with melanoma and leukemias.

In one embodiment, the PRAME antigen is a mammalian PRAME antigen. In one embodiment, the PRAME antigen is a consensus PRAME antigen derived from multiple mammalian PRAME antigen sequences. In one embodiment, a PRAME antigen is operably linked to a signal peptide.

In one embodiment, a PRAME antigen can be administered in vectors described herein, and combined with the MAGE-A antigen and optionally one or more antibodies targeting one or more additional immune checkpoint proteins in various vaccination schedules.

The PRAME antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune response. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The PRAME antigen can comprise protein epitopes that make it particularly effective as an immunogen against which anti-PRAME immune responses can be induced. The PRAME antigen can comprise the full-length translation product, a variant thereof, a fragment thereof or a combination thereof. The PRAME antigen can comprise a consensus protein.

The nucleic acid sequence encoding the consensus PRAME antigen can be optimized with regards to codon usage and corresponding RNA transcripts. The nucleic acid encoding the consensus PRAME antigen can be codon and RNA optimized for expression in mammals. In some embodiments, the nucleic acid sequence encoding the consensus PRAME antigen can include a Kozak sequence to increase the efficiency of translation. The nucleic acid encoding the consensus PRAME antigen can include one or more stop codons to increase the efficiency of translation termination.

The nucleic acid encoding the consensus PRAME antigen can also encode an immunoglobulin E (IgE) leader sequence. The nucleic acid encoding the consensus PRAME antigen can further encode the IgE leader sequence such that the amino acid sequence of the IgE leader sequence is linked to the amino acid sequence of the consensus PRAME antigen by a peptide bond. The nucleic acid encoding the consensus PRAME antigen can also include a nucleotide sequence encoding the IgE leader sequence. In some embodiments, the nucleic acid encoding the consensus PRAMS antigen is free of or does not contain a nucleotide sequence encoding the IgE leader sequence.

(10) PSA

The vaccine of the present invention can comprise the cancer antigen prostate specific antigen (PSA; also known as gamma-seminoprotein or kallikrein-3 (KLK3)), a fragment thereof, or a variant thereof. PSA is an androgen-regulated serine protease produced by prostate epithelial cells and prostate cancer cells and encoded by the KLK3 gene. PSA is often used as a serum marker for prostate cancer. PSA is a member of the tissue kallikrein family and cleaves semenogelins in seminal coagulum after cleavage of the proenzyme to release the active enzyme, thereby liquefying semen to allow sperm to swim freely. Additionally, PSA enzymatic activity is regulated by zinc concentration, namely high zinc concentrations inhibit enzymatic activity of PSA.

In one embodiment, the PSA antigen is a mammalian PSA antigen. In one embodiment, the PSA antigen is a consensus PSA antigen derived from multiple mammalian PSA antigen sequences. In one embodiment, a PSA antigen is operably linked to a signal peptide.

In one embodiment, a PSA antigen can be administered in vectors described herein, and combined with the MAGE-A antigen and optionally one or more antibodies targeting one or more additional immune checkpoint proteins in various vaccination schedules.

The PSA antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune response. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The PSA antigen can comprise protein epitopes that make them particularly effective as immunogens against which anti-PSA immune responses can be induced. The PSA antigen can comprise the full-length translation product, a variant thereof, a fragment thereof or a combination thereof. The PSA antigen can comprise a consensus protein.

The nucleic acid sequence encoding the consensus PSA antigen can be optimized with regards to codon usage and corresponding RNA transcripts. The nucleic acid encoding the consensus PSA antigen can be codon and RNA optimized for expression in mammals. In some embodiments, the nucleic acid sequence encoding the consensus PSA antigen can include a Kozak sequence to increase the efficiency of translation. The nucleic acid encoding the consensus PSA antigen can include one or more stop codons to increase the efficiency of translation termination.

The nucleic acid encoding the consensus PSA antigen can also encode an immunoglobulin E (IgE) leader sequence. The nucleic acid encoding the consensus PSA antigen can further encode the IgE leader sequence such that the amino acid sequence of the IgE leader sequence is linked to the amino acid sequence of the consensus PSA P antigen by a peptide bond. The nucleic acid encoding the consensus PSA antigen can also include a nucleotide sequence encoding the IgE leader sequence. In some embodiments, the nucleic acid encoding the consensus PSA antigen is free of or does not contain a nucleotide sequence encoding the IgE leader sequence.

In some embodiments, the nucleic acid encoding the consensus PSA antigen can be a heterologous nucleic acid sequence and/or contain one or more heterologous nucleic acid sequences.

(11) PSMA

The vaccine of the present invention can comprise the cancer antigen prostate specific membrane antigen (PSMA; also known as Glutamate carboxypeptidase II (GCPII), N-acetyl-L-aspartyl-L-glutamate peptidase I (NAALADase I), and NAAG peptidase), a fragment thereof, or a variant thereof. PSMA is encoded by the folate hydrolase 1 (FOLH1) gene. PSMA is a zinc metalloenzyme found residing in membranes and the extracellular space. PSMA is highly expressed in the human prostate and is upregulated in prostate cancer. PSMA is also found to be overexpressed in other cancers such as solid tumors of the kidney, breast, and colon.

In one embodiment, the PSMA antigen is a mammalian PSMA antigen. In one embodiment, the PSMA antigen is a consensus PSMA antigen derived from multiple mammalian PSMA antigen sequences. In one embodiment, a PSMA antigen is operably linked to a signal peptide.

In one embodiment, a PSMA antigen can be administered in vectors described herein, and combined with the MAGE-A antigen and optionally one or more antibodies targeting one or more additional immune checkpoint proteins in various vaccination schedules.

The PSMA antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune response. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The PSMA antigen can comprise protein epitopes that make them particularly effective as immunogens against which anti-PSMA immune responses can be induced. The PSMA antigen can comprise the full-length translation product, a variant thereof, a fragment thereof or a combination thereof. The PSMA antigen can comprise a consensus protein.

The nucleic acid sequence encoding the consensus PSMA antigen can be optimized with regards to codon usage and corresponding RNA transcripts. The nucleic acid encoding the consensus PSMA antigen can be codon and RNA optimized for expression in mammals. In some embodiments, the nucleic acid sequence encoding the consensus PSMA antigen can include a Kozak sequence to increase the efficiency of translation. The nucleic acid encoding the consensus PSMA antigen can include one or more stop codons to increase the efficiency of translation termination.

The nucleic acid encoding the consensus PSMA antigen can also encode an immunoglobulin E (IgE) leader sequence. The nucleic acid encoding the consensus PSMA antigen can further encode the IgE leader sequence such that the amino acid sequence of the IgE leader sequence is linked to the amino acid sequence of the consensus PSMA antigen by a peptide bond. The nucleic acid encoding the consensus PSMA antigen can also include a nucleotide sequence encoding the IgE leader sequence. In some embodiments, the nucleic acid encoding the consensus PSMA antigen is free of or does not contain a nucleotide sequence encoding the IgE leader sequence.

In some embodiments, the nucleic acid encoding the consensus PSMA antigen can be a heterologous nucleic acid sequence and/or contain one or more heterologous nucleic acid sequences.

(12) STEAP

The vaccine of the present invention can comprise the cancer antigen six-transmembrane epithelial antigen of the prostate antigen (STEAP), a fragment thereof, or a variant thereof. STEAP is a metalloreductase encoded by the STEAP1 gene. STEAP is largely expressed in prostate tissues and is upregulated in cancer cells. STEAP is predicted to be a six-transmembrane protein and is a cell surface antigen found at cell-cell junctions.

In one embodiment, the STEAP antigen is a mammalian STEAP antigen. In one embodiment, the STEAP antigen is a consensus STEAP antigen derived from multiple mammalian STEAP antigen sequences. In one embodiment, a STEAP antigen is operably linked to a signal peptide.

In one embodiment, a STEAP antigen can be administered in vectors described herein, and combined with the MAGE-A antigen and optionally one or more antibodies targeting one or more additional immune checkpoint proteins in various vaccination schedules.

The STEAP antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune response. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The STEAP antigen can comprise protein epitopes that make them particularly effective as immunogens against which anti-STEAP immune responses can be induced. The STEAP antigen can comprise the full-length translation product, a variant thereof, a fragment thereof or a combination thereof. The STEAP antigen can comprise a consensus protein.

The nucleic acid sequence encoding the consensus STEAP antigen can be optimized with regards to codon usage and corresponding RNA transcripts. The nucleic acid encoding the consensus STEAP antigen can be codon and RNA optimized for expression in mammals. In some embodiments, the nucleic acid sequence encoding the consensus STEAP antigen can include a Kozak sequence to increase the efficiency of translation. The nucleic acid encoding the consensus STEAP antigen can include one or more stop codons to increase the efficiency of translation termination.

The nucleic acid encoding the consensus STEAP antigen can also encode an immunoglobulin E (IgE) leader sequence. The nucleic acid encoding the consensus STEAP antigen can further encode the IgE leader sequence such that the amino acid sequence of the IgE leader sequence is linked to the amino acid sequence of the consensus STEAP antigen by a peptide bond. The nucleic acid encoding the consensus STEAP antigen can also include a nucleotide sequence encoding the IgE leader sequence. In some embodiments, the nucleic acid encoding the consensus STEAP antigen is free of or does not contain a nucleotide sequence encoding the IgE leader sequence.

In some embodiments, the nucleic acid encoding the consensus STEAP antigen can be a heterologous nucleic acid sequence and/or contain one or more heterologous nucleic acid sequences.

(13) PSCA

The vaccine of the present invention can comprise the cancer antigen prostate specific stem cell antigen (PSCA), a fragment thereof, or a variant thereof. PSCA is a glycosylphosphatidylinositol (GPI)-anchored cell surface protein and is encoded by an androgen-responsive gene. PSCA is a member of the Thy-1/Ly-6 family of GPI-anchored cell surface antigens. PSCA is upregulated in many cancers including prostate, bladder, and pancreatic cancers.

In one embodiment, the PSCA antigen is a mammalian PSCA antigen. In one embodiment, the PSCA antigen is a consensus PSCA antigen derived from multiple mammalian PSCA antigen sequences. In one embodiment, a PSCA antigen is operably linked to a signal peptide.

In one embodiment, a PSCA antigen can be administered in vectors described herein, and combined with the MAGE-A antigen and optionally one or more antibodies targeting one or more additional immune checkpoint proteins in various vaccination schedules.

The PSCA antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune response. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The PSCA antigen can comprise protein epitopes that make them particularly effective as immunogens against which anti-PSCA immune responses can be induced. The PSCA antigen can comprise the full-length translation product, a variant thereof, a fragment thereof or a combination thereof. The PSCA antigen can comprise a consensus protein.

The nucleic acid sequence encoding the consensus PSCA antigen can be optimized with regards to codon usage and corresponding RNA transcripts. The nucleic acid encoding the consensus PSCA antigen can be codon and RNA optimized for expression in mammals. In some embodiments, the nucleic acid sequence encoding the consensus PSCA antigen can include a Kozak sequence to increase the efficiency of translation. The nucleic acid encoding the consensus PSCA antigen can include one or more stop codons to increase the efficiency of translation termination.

The nucleic acid encoding the consensus PSCA antigen can also encode an immunoglobulin E (IgE) leader sequence. The nucleic acid encoding the consensus PSCA antigen can further encode the IgE leader sequence such that the amino acid sequence of the IgE leader sequence is linked to the amino acid sequence of the consensus PSCA antigen by a peptide bond. The nucleic acid encoding the consensus PSCA antigen can also include a nucleotide sequence encoding the IgE leader sequence. In some embodiments, the nucleic acid encoding the consensus PSCA antigen is free of or does not contain a nucleotide sequence encoding the IgE leader sequence.

In some embodiments, the nucleic acid encoding the consensus PSCA antigen can be a heterologous nucleic acid sequence and/or contain one or more heterologous nucleic acid sequences.

(14) WT1

The vaccine of the present invention can comprise the cancer antigen Wilm's tumor 1 (WT1), a fragment thereof, or a variant thereof. WT1 is a transcription factor containing at the N-terminus, a proline/glutamine-rich DNA-binding domain and at the C-terminus, four zinc finger motifs. WT1 plays a role in the normal development of the urogenital system and interacts with numerous factors, for example, p53, a known tumor suppressor and the serine protease HtrA2, which cleaves WT1 at multiple sites after treatment with a cytotoxic drug.

Mutation of WT1 can lead to tumor or cancer formation, for example, neproblastoma or tumors expressing WT1. Neproblastoma often forms in one or both kidneys before metastasizing to other tissues, for example, but not limited to, liver tissue, urinary tract system tissue, lymph tissue, and lung tissue. Accordingly, neproblastoma can be considered a metastatic tumor.

In one embodiment, the WT1 antigen is a mammalian WT1 antigen. In one embodiment, the WT1 antigen is a consensus WT1 antigen derived from multiple mammalian WT1 antigen sequences. In one embodiment, a WT1 antigen is operably linked to a signal peptide.

In one embodiment, a WT1 antigen can be administered in vectors described herein, and combined with the MAGE-A antigen and optionally one or more antibodies targeting one or more additional immune checkpoint proteins in various vaccination schedules.

The WT-1 antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune response. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

Accordingly, the vaccine can be used for treating subjects suffering from neproblastoma. The vaccine can be used for treating subjects suffering from any number of cancers including, but not limited to, melanoma, prostate cancer, liver cancer, cervical cancer, recurrent respiratory papillomatosis (RRP), anal cancer, head and neck cancer, and blood cancers. The vaccine can also be used for treating subjects with cancers or tumors that express WT1 for preventing development of such tumors in subjects. The WT1 antigen can differ from the native, "normal" WT1 gene, and thus, provide therapy or prophylaxis against an WT1 antigen-expressing tumor. Accordingly, WT1 antigen sequences that differ from the native WT1 gene (i.e., mutated WT1 genes or sequences) are provided herein.

The WT1 antigen can be a consensus antigen (or immunogen) sequence derived from two or more species. The WT1 antigen can comprise a consensus sequence and/or modification(s) for improved expression. Modification can include codon optimization, RNA optimization, additional of a kozak sequence for increased translation initiation and/or the addition of an immunoglobulin leader sequence to increase the immunogenicity of the WT1 antigen. The WT1 antigen can comprise a signal peptide such as an immunoglobulin signal peptide, for example, but not limited to, an immunoglobulin E (IgE) or immunoglobulin G (IgG) signal peptide. In some embodiments, the WT1 consensus antigen can comprise a hemagglutinin (HA) tag. The WT1 consensus antigen can be designed to elicit stronger and broader cellular and/or humoral immune responses than a corresponding codon optimized WT1 antigen.

(15) gp100

The vaccine of the present invention can comprise the cancer antigen glycoprotein 100 (gp100; also known as Trp2 and premelanosome protein (PMEL)), a fragment thereof, or a variant thereof. gp100 is encoded by the PMEL gene. It is a 70 kDa type 1 transmembrane glycoprotein, comprised of 661 amino acids that plays a central role in the biogenesis of melanosomes as it is involved in the maturation of melanosomes from stage I to II. gp100 drives the formation of striations from within multivesicular bodies and is directly involved in the biogenesis of premelanosomes. gp100 is enriched in premelanosomes relative to mature melanosomes, but overexpressed by proliferating neonatal melanocytes and during tumor growth. The gp100 protein includes a variety of immunogenic epitopes that are recognized by cytotoxic T lymphocytes from peripheral blood of melanoma patients and from tumor infiltrating lymphocytes.

In one embodiment, the GP100 antigen is a mammalian GP100 antigen. In one embodiment, the GP100 antigen is a consensus GP100 antigen derived from multiple mammalian GP100 antigen sequences. In one embodiment, a GP100 antigen is operably linked to a signal peptide.

In one embodiment, a GP100 antigen can be administered in vectors described herein, and combined with the MAGE-A antigen and optionally one or more antibodies targeting one or more additional immune checkpoint proteins in various vaccination schedules.

The gp100 antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune response. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The gp100 antigen can comprise protein epitopes that make them particularly effective as immunogens against which anti-gp100 immune responses can be induced. The gp100 antigen can comprise the full-length translation product, a variant thereof, a fragment thereof or a combination thereof. The gp100 antigen can comprise a consensus protein.

The nucleic acid sequence encoding the consensus gp100 antigen can be optimized with regards to codon usage and corresponding RNA transcripts. The nucleic acid encoding the consensus gp100 antigen can be codon and RNA optimized for expression in mammals. In some embodiments, the nucleic acid sequence encoding the consensus gp100 antigen can include a Kozak sequence to increase the efficiency of translation. The nucleic acid encoding the consensus gp100 antigen can include one or more stop codons to increase the efficiency of translation termination.

The nucleic acid encoding the gp100 antigen can also encode an immunoglobulin E (IgE) leader sequence. The nucleic acid encoding the gp100 antigen can further encode the IgE leader sequence such that the amino acid sequence of the IgE leader sequence is linked to the amino acid sequence of the gp100 antigen by a peptide bond. The nucleic acid encoding the gp100 antigen can also include a nucleotide sequence encoding the IgE leader sequence. In some embodiments, the nucleic acid encoding the gp100 antigen is free of or does not contain a nucleotide sequence encoding the IgE leader sequence.

(16) FSHR

Follicle stimulating hormone receptor (FSHR) is an antigen that is selectively expressed in females in the ovarian granulosa cells (Simoni et al., Endocr Rev. 1997, 18:739-773) and at low levels in the ovarian endothelium (Vannier et al., Biochemistry, 1996, 35:1358-1366).

In various embodiments, the FSHR antigen comprises a consensus protein or a nucleic acid molecule encoding a consensus protein. FSHR antigens include sequences homologous to the FSHR antigens, fragments of the FSHR antigens and proteins with sequences homologous to fragments of the FSHR antigens.

The FSHR antigens can be administered in vectors described herein, and combined with the CTLA4 antibody and optionally one or more antibodies targeting one or more additional immune checkpoint proteins in various vaccination schedules.

In one embodiment, an FSHR antigen is mammalian FSHR. In one embodiment, an FSHR antigen is a consensus FSHR antigen derived from multiple mammal FSHR sequences. In one embodiment, a FSHR antigen is operably linked to a signal peptide.

In one embodiment, an FSHR antigen can be administered in vectors described herein, and combined with the MAGE-A antigen and optionally one or more antibodies targeting one or more additional immune checkpoint proteins in various vaccination schedules.

The FSHR antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune response. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The FSHR antigen can comprise protein epitopes that make them particularly effective as immunogens against which anti-F SHR immune responses can be induced. The FSHR antigen can comprise the full-length translation product, a variant thereof, a fragment thereof or a combination thereof. The FSHR antigen can comprise a consensus protein.

The nucleic acid sequence encoding the consensus FSHR antigen can be optimized with regards to codon usage and corresponding RNA transcripts. The nucleic acid encoding the consensus FSHR antigen can be codon and RNA optimized for expression in mammals. In some embodiments, the nucleic acid sequence encoding the consensus FSHR antigen can include a Kozak sequence to increase the efficiency of translation. The nucleic acid encoding the consensus FSHR antigen can include one or more stop codons to increase the efficiency of translation termination.

The nucleic acid encoding the FSHR antigen can also encode an immunoglobulin E (IgE) leader sequence. The nucleic acid encoding the FSHR antigen can further encode the IgE leader sequence such that the amino acid sequence of the IgE leader sequence is linked to the amino acid sequence of the FSHR antigen by a peptide bond. The nucleic acid encoding the FSHR antigen can also include a nucleotide sequence encoding the IgE leader sequence. In some embodiments, the nucleic acid encoding the FSHR antigen is free of or does not contain a nucleotide sequence encoding the IgE leader sequence.

(17) Tumor Microenvironment Antigens

Several proteins are overexpressed in the tumor microenvironment including, but not limited to, Fibroblast Activation Protein (FAP), and Platelet Derived Growth Factor Receptor Beta (PDGFR-β). FAP is a membrane-bound enzyme with gelatinase and peptidase activity that is up-regulated in cancer-associated fibroblasts in over 90% of human carcinomas. PDGFR-β is a cell surface tyrosine kinase receptor that has roles in the regulation of many biological processes including embryonic development, angiogenesis, cell proliferation and differentiation.

In various embodiments, the tumor microenvironment antigen comprises a consensus protein or a nucleic acid molecule encoding a consensus protein. Tumor microenvironment antigens include sequences homologous to the tumor microenvironment antigens, fragments of the tumor microenvironment antigens and proteins with sequences homologous to fragments of the tumor microenvironment antigens.

In one embodiment, the tumor microenvironment antigen is a mammalian tumor microenvironment antigen. In one embodiment, the tumor microenvironment antigen is a consensus tumor microenvironment antigen derived from multiple mammalian tumor microenvironment antigen sequences. In one embodiment, a tumor microenvironment antigen is operably linked to a signal peptide.

One or more tumor microenvironment antigens can be administered in vectors described herein, and combined with the MAGE-A antigen and optionally one or more antibodies targeting one or more additional immune checkpoint proteins in various vaccination schedules.

The tumor microenvironment antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune response. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The tumor microenvironment antigen can comprise protein epitopes that make them particularly effective as immunogens against which anti-tumor microenvironment immune responses can be induced. The tumor microenvironment antigen can comprise the full-length translation product, a variant thereof, a fragment thereof or a combination thereof. The tumor microenvironment antigen can comprise a consensus protein.

The nucleic acid sequence encoding the consensus tumor microenvironment antigen can be optimized with regards to codon usage and corresponding RNA transcripts. The nucleic acid encoding the consensus tumor microenvironment antigen can be codon and RNA optimized for expression in mammals. In some embodiments, the nucleic acid sequence encoding the consensus tumor microenvironment antigen can include a Kozak sequence to increase the efficiency of translation. The nucleic acid encoding the consensus tumor microenvironment antigen can include one or more stop codons to increase the efficiency of translation termination.

The nucleic acid encoding the tumor microenvironment antigen can also encode an immunoglobulin E (IgE) leader sequence. The nucleic acid encoding the tumor microenvironment antigen can further encode the IgE leader sequence such that the amino acid sequence of the IgE leader sequence is linked to the amino acid sequence of the tumor microenvironment antigen by a peptide bond. The nucleic acid encoding the tumor microenvironment antigen can also include a nucleotide sequence encoding the IgE leader sequence. In some embodiments, the nucleic acid encoding the tumor microenvironment antigen is free of or does not contain a nucleotide sequence encoding the IgE leader sequence.

(18) Viral Antigens

The cancer antigen can be a viral antigen, a fragment thereof, or a variant thereof. The viral antigen can be antigen from a mammalian virus (e.g., Papillomavirus or EBV-like virus). In one embodiment, the viral antigen is a consensus viral antigen derived from multiple mammalian virus antigen sequences. In one embodiment, a viral antigen is operably linked to a signal peptide.

In one embodiment, the viral antigen can be administered in vectors described herein, and combined with the MAGE-A antigen and optionally one or more antibodies targeting one or more additional immune checkpoint proteins in various vaccination schedules.

The viral antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune response. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule, which is described below in more detail.

The viral antigen can comprise protein epitopes that make them particularly effective as immunogens against which anti-viral immune responses can be induced. The viral antigen can comprise the full-length translation product, a variant thereof, a fragment thereof or a combination thereof. The viral antigen can comprise a consensus protein.

The nucleic acid sequence encoding the viral antigen can be optimized with regards to codon usage and corresponding RNA transcripts. The nucleic acid encoding the viral antigen can be codon and RNA optimized for expression in mammals. In some embodiments, the nucleic acid sequence encoding the viral antigen can include a Kozak sequence to increase the efficiency of translation. The nucleic acid encoding the viral antigen can include one or more stop codons to increase the efficiency of translation termination.

The nucleic acid encoding the viral antigen can also encode an immunoglobulin E (IgE) leader sequence. The nucleic acid encoding the viral antigen can further encode the IgE leader sequence such that the amino acid sequence of the IgE leader sequence is linked to the amino acid sequence of the viral antigen by a peptide bond. The nucleic acid encoding the viral antigen can also include a nucleotide sequence encoding the IgE leader sequence. In some embodiments, the nucleic acid encoding the viral antigen is free of or does not contain a nucleotide sequence encoding the IgE leader sequence.

3. VACCINE IN COMBINATION WITH IMMUNE CHECKPOINT INHIBITOR

The vaccine can further comprise one or more inhibitors of one or more immune checkpoint molecules (i.e., an immune checkpoint inhibitor). Immune checkpoint molecules are described below in more detail. The immune checkpoint inhibitor is any nucleic acid or protein that prevents the suppression of any component in the immune system such as WIC class presentation, T cell presentation and/or differentiation, B cell presentation and/or differentiation, any cytokine, chemokine or signaling for immune cell proliferation and/or differentiation.

Such an inhibitor can be a nucleic acid sequence, an amino acid sequence, a small molecule, or a combination thereof. The nucleic acid sequence can be DNA, RNA, cDNA, a variant thereof, a fragment thereof, or a combination thereof. The nucleic acid can also include additional sequences that encode linker or tag sequences that are linked to the immune checkpoint inhibitor by a peptide bond. The small molecule may be a low molecular weight, for example, less than 800 Daltons, organic or inorganic compound that can serve as an enzyme substrate, ligand (or analog thereof) bound by a protein or nucleic acid, or regulator of a biological process. The amino acid sequence can be protein, a peptide, a variant thereof, a fragment thereof, or a combination thereof.

In some embodiments, the immune checkpoint inhibitor can be one or more nucleic acid sequences encoding an antibody, a variant thereof, a fragment thereof, or a combination thereof. In other embodiments, the immune checkpoint inhibitor can be an antibody, a variant thereof, a fragment thereof, or a combination thereof.

a. Immune Checkpoint Molecule

The immune checkpoint molecule can be a nucleic acid sequence, an amino acid sequence, a small molecule, or a combination thereof. The nucleic acid sequence can be DNA, RNA, cDNA, a variant thereof, a fragment thereof, or a combination thereof. The nucleic acid can also include additional sequences that encode linker or tag sequences that are linked to the immune checkpoint inhibitor by a peptide bond. The small molecule may be a low molecular weight, for example, less than 800 Daltons, organic or inorganic compound that can serve as an enzyme substrate, ligand (or analog thereof) bound by a protein or nucleic acid, or regulator of a biological process. The amino acid sequence can be protein, a peptide, a variant thereof, a fragment thereof, or a combination thereof.

Checkpoint inhibitors can be any antagonist to the various immune checkpoints. In some instances, the checkpoint inhibitors are antibodies that block immune checkpoints. The antibodies can be a protein including a Fab, monoclonal or polyclonal. The antibodies can also be a DNA expression construct that encodes for and can express functional antibodies. The vaccine can further comprise a PD-1 antibody, PD-L1 antibody, LAG-3 antibody, GITR antibody, CD40 antibody, OX40 antibody, CTLA-4 antibody, TIM-3 antibody, and/or a 4-1BB antibody. The antibody can be a synthetic antibody comprised of DNA sequence encoding at least the variable regions of an immunoglobulin. Such antibody can be generated by identifying or screening for the antibody described above, which is reactive to or binds the antigen described above. The method of identifying or screening for the antibody can use the antigen in methodologies known to those skilled in art to identify or screen for the antibody. Such methodologies can include, but are not limited to, selection of the antibody from a library (e.g., phage display) and immunization of an animal followed by isolation and/or purification of the antibody. See for example methods available in Rajan, S., and Sidhu, S., *Methods in Enzymology*, vol 502, Chapter One "Simplified Synthetic Antibody Libraries (2012), which is incorporated herein in its entirety.

b. Anti-Immune Checkpoint Molecule Antibody

As described above, the immune checkpoint inhibitor can be an antibody. The antibody can bind or react with an antigen (i.e., the immune checkpoint molecule described above). Accordingly, the antibody may be considered an anti-immune checkpoint molecule antibody or an immune checkpoint molecule antibody. The antibody can be encoded by a nucleic acid sequence.

The antibody can include a heavy chain polypeptide and a light chain polypeptide. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region.

In some embodiments, the heavy chain polypeptide can include a VH region and a CH1 region. In other embodiments, the heavy chain polypeptide can include a VH region, a CH1 region, a hinge region, a CH2 region, and a CH3 region.

The heavy chain polypeptide can include a complementarity determining region ("CDR") set. The CDR set can contain three hypervariable regions of the VH region. Proceeding from N-terminus of the heavy chain polypeptide, these CDRs are denoted "CDR1," "CDR2," and "CDR3," respectively. CDR1, CDR2, and CDR3 of the heavy chain polypeptide can contribute to binding or recognition of the antigen.

The light chain polypeptide can include a variable light chain (VL) region and/or a constant light chain (CL) region. The light chain polypeptide can include a complementarity determining region ("CDR") set. The CDR set can contain three hypervariable regions of the VL region. Proceeding from N-terminus of the light chain polypeptide, these CDRs are denoted "CDR1," "CDR2," and "CDR3," respectively. CDR1, CDR2, and CDR3 of the light chain polypeptide can contribute to binding or recognition of the antigen.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

Additionally, the proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment, which comprises both antigen-binding sites. Accordingly, the antibody can be the Fab or F(ab')$_2$. The Fab can include the heavy chain polypeptide and the light chain polypeptide. The heavy chain polypeptide of the Fab can include the VH region and the CH1 region. The light chain of the Fab can include the VL region and CL region.

The antibody can be a polyclonal or monoclonal antibody. The antibody can be a chimeric antibody, a single chain antibody, an affinity matured antibody, a human antibody, a humanized antibody, or a fully human antibody. The humanized antibody can be an antibody from a non-human species that binds the desired antigen having one or more complementarity determining regions (CDRs) from the non-human species and framework regions from a human immunoglobulin molecule.

4. VACCINE CONSTRUCTS AND PLASMIDS

The vaccine can comprise nucleic acid constructs or plasmids that encode the above described antigens and/or antibodies. The nucleic acid constructs or plasmids can include or contain one or more heterologous nucleic acid sequences. Provided herein are genetic constructs that can comprise a nucleic acid sequence that encodes the above described antigens and/or antibodies. The genetic construct can be present in the cell as a functioning extrachromosomal molecule. The genetic construct can be a linear minichromosome including centromere, telomeres or plasmids or cosmids. The genetic constructs can include or contain one or more heterologous nucleic acid sequences.

The genetic constructs can be in the form of plasmids expressing the above described antigens and/or antibodies in any order.

The genetic construct can also be part of a genome of a recombinant viral vector, including recombinant adenovirus, recombinant adenovirus associated virus and recombinant vaccinia. The genetic construct can be part of the genetic material in attenuated live microorganisms or recombinant microbial vectors which live in cells.

The genetic constructs can comprise regulatory elements for gene expression of the coding sequences of the nucleic acid. The regulatory elements can be a promoter, an enhancer an initiation codon, a stop codon, or a polyadenylation signal.

The nucleic acid sequences can make up a genetic construct that can be a vector. The vector can be capable of expressing the above described antigens and/or antibodies in the cell of a mammal in a quantity effective to elicit an immune response in the mammal. The vector can be recombinant. The vector can comprise heterologous nucleic acid encoding the above described antigens and/or antibodies. The vector can be a plasmid. The vector can be useful for transfecting cells with nucleic acid encoding the above described antigens and/or antibodies, which the transformed host cell is cultured and maintained under conditions wherein expression of the above described antigens and/or antibodies takes place.

Coding sequences can be optimized for stability and high levels of expression. In some instances, codons are selected to reduce secondary structure formation of the RNA such as that formed due to intramolecular bonding.

The vector can comprise heterologous nucleic acid encoding the above described antigens and/or antibodies and can further comprise an initiation codon, which can be upstream of the one or more cancer antigen coding sequence(s), and a stop codon, which can be downstream of the coding sequence(s) of the above described antigens and/or antibodies. The initiation and termination codon can be in frame with the coding sequence(s) of the above described antigens and/or antibodies. The vector can also comprise a promoter that is operably linked to the coding sequence(s) of the above described antigens and/or antibodies. The promoter operably linked to the coding sequence(s) of the above described antigens and/or antibodies can be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter can also be a promoter from a human gene such as human actin, human myosin, human hemoglobin, human muscle creatine, or human metallothionein. The promoter can also be a tissue specific promoter, such as a muscle or skin specific promoter, natural or synthetic. Examples of such promoters are described in US patent application publication no. US20040175727, the contents of which are incorporated herein in its entirety.

The vector can also comprise a polyadenylation signal, which can be downstream of the coding sequence(s) of the above described antigens and/or antibodies. The polyadenylation signal can be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal can be a polyadenylation signal from a pCEP4 vector (Invitrogen, San Diego, CA).

The vector can also comprise an enhancer upstream of the above described antigens and/or antibodies. The enhancer can be necessary for DNA expression. The enhancer can be human actin, human myosin, human hemoglobin, human muscle creatine or a viral enhancer such as one from CMV, HA, RSV or EBV. Polynucleotide function enhancers are described in U.S. Pat. Nos. 5,593,972, 5,962,428, and WO94/016737, the contents of each are fully incorporated by reference.

The vector can also comprise a mammalian origin of replication in order to maintain the vector extrachromosomally and produce multiple copies of the vector in a cell. The vector can be pVAX1, pCEP4 or pREP4 from Invitrogen (San Diego, CA), which can comprise the Epstein Barr virus origin of replication and nuclear antigen EBNA-1 coding region, which can produce high copy episomal replication without integration. The vector can be pVAX1 or a pVax1 variant with changes such as the variant plasmid described herein. The variant pVax1 plasmid is a 2998 basepair variant of the backbone vector plasmid pVAX1 (Invitrogen, Carlsbad CA). The CMV promoter is located at bases 137-724. The T7 promoter/priming site is at bases 664-683. Multiple cloning sites are at bases 696-811. Bovine GH polyadenylation signal is at bases 829-1053. The Kanamycin resistance gene is at bases 1226-2020. The pUC origin is at bases 2320-2993.

The backbone of the vector can be pAV0242. The vector can be a replication defective adenovirus type 5 (Ad5) vector.

The vector can also comprise a regulatory sequence, which can be well suited for gene expression in a mammalian or human cell into which the vector is administered. The one or more cancer antigen sequences disclosed herein can comprise a codon, which can allow more efficient transcription of the coding sequence in the host cell.

The vector can be pSE420 (Invitrogen, San Diego, Calif.), which can be used for protein production in *Escherichia coli* (*E. coli*). The vector can also be pYES2 (Invitrogen, San Diego, Calif.), which can be used for protein production in *Saccharomyces cerevisiae* strains of yeast. The vector can also be of the MAXBAC™ complete baculovirus expression system (Invitrogen, San Diego, Calif.), which can be used for protein production in insect cells. The vector can also be pcDNA I or pcDNA3 (Invitrogen, San Diego, Calif.), which may be used for protein production in mammalian cells, such as Chinese hamster ovary (CHO) cells. The vector can be expression vectors or systems to produce protein by routine techniques and readily available starting materials including Sambrook et al., Molecular Cloning and Laboratory Manual, Second Ed., Cold Spring Harbor (1989), which is incorporated fully by reference.

In some embodiments, the vector can comprise one or more of the nucleic acid sequences of SEQ ID NOs: 1, and/or 3, or a fragment or variant thereof.

5. PHARMACEUTICAL COMPOSITIONS OF THE VACCINE

The vaccine can be in the form of a pharmaceutical composition. The pharmaceutical composition can comprise the vaccine. The pharmaceutical compositions can comprise about 5 nanograms to about 10 mg of the DNA of the vaccine. In some embodiments, pharmaceutical compositions according to the present invention comprise about 25 nanogram to about 5 mg of DNA of the vaccine. In some embodiments, the pharmaceutical compositions contain about 50 nanograms to about 1 mg of DNA of the vaccine. In some embodiments, the pharmaceutical compositions contain about 0.1 to about 500 micrograms of DNA of the vaccine. In some embodiments, the pharmaceutical compositions contain about 1 to about 350 micrograms of DNA of the vaccine. In some embodiments, the pharmaceutical compositions contain about 5 to about 250 micrograms of DNA of the vaccine. In some embodiments, the pharmaceutical compositions contain about 10 to about 200 micrograms of DNA of the vaccine. In some embodiments, the pharmaceutical compositions contain about 15 to about 150 micrograms of DNA of the vaccine. In some embodiments, the pharmaceutical compositions contain about 20 to about 100 micrograms of DNA of the vaccine. In some embodiments, the pharmaceutical compositions contain about 25 to about 75 micrograms of DNA of the vaccine. In some embodiments, the pharmaceutical compositions contain about 30 to about 50 micrograms of DNA of the vaccine. In some embodiments, the pharmaceutical compositions contain about 35 to about 40 micrograms of DNA of the vaccine. In some embodiments, the pharmaceutical compositions contain about 100 to about 200 micrograms of DNA of the vaccine. In some embodiments, the pharmaceutical compositions comprise about 10 micrograms to about 100 micrograms of DNA of the vaccine. In some embodiments, the pharmaceutical compositions comprise about 20 micrograms to about 80 micrograms of DNA of the vaccine. In some embodiments, the pharmaceutical compositions comprise about 25 micrograms to about 60 micrograms of DNA of the vaccine. In some embodiments, the pharmaceutical compositions comprise about 30 nanograms to about 50 micrograms of DNA of the vaccine. In some embodiments, the pharmaceutical compositions comprise about 35 nanograms to about 45 micrograms of DNA of the vaccine. In some embodiments, the pharmaceutical compositions contain about 0.1 to about 500 micrograms of DNA of the vaccine. In some embodiments, the pharmaceutical compositions contain about 1 to about 350 micrograms of DNA of the vaccine. In some embodiments, the pharmaceutical compositions contain about 25 to about 250 micrograms of DNA of the vaccine. In some embodiments, the pharmaceutical compositions contain about 100 to about 200 microgram DNA of the vaccine.

In some embodiments, pharmaceutical compositions according to the present invention comprise at least 10, 15, 20, 25, 30, 35, 40, 45, 50, 55, 60, 65, 70, 75, 80, 85, 90, 95 or 100 nanograms of DNA of the vaccine. In some embodiments, the pharmaceutical compositions can comprise at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995 or 1000 micrograms of DNA of the vaccine. In some embodiments, the pharmaceutical composition can comprise at least 1.5, 2, 2.5, 3, 3.5, 4, 4.5, 5, 5.5, 6, 6.5, 7, 7.5, 8, 8.5, 9, 9.5 or 10 mg or more of DNA of the vaccine.

In other embodiments, the pharmaceutical composition can comprise up to and including 15, 20, 25, 30, 35, 40, 45, 50, 55, 60, 65, 70, 75, 80, 85, 90, 95 or 100 nanograms of DNA of the vaccine. In some embodiments, the pharmaceutical composition can comprise up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995, or 1000 micrograms of DNA of the vaccine. In some embodiments, the pharmaceutical composition can comprise up to and including 1.5, 2, 2.5, 3, 3.5, 4, 4.5, 5, 5.5, 6, 6.5, 7, 7.5, 8, 8.5, 9, 9.5 or 10 mg of DNA of the vaccine.

The pharmaceutical composition can further comprise other agents for formulation purposes according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

The vaccine can further comprise a pharmaceutically acceptable excipient. The pharmaceutically acceptable excipient can be functional molecules as vehicles, adjuvants, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent may be a polyanion, polycation, including poly-L-glutamate (LGS), or lipid. The transfection facilitating agent may be poly-L-glutamate, and for example, the poly-L-glutamate is present in the vaccine at a concentration less than 6 mg/ml. The transfection facilitating agent can also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid can also be used administered in conjunction with the genetic construct. In some embodiments, the DNA vector vaccines can also include a transfection facilitating agent such as lipids, liposomes, including lecithin liposomes or other liposomes known in the art, as a DNA-liposome mixture (see for example WO1993024640A2), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can include an adjuvant. The adjuvant can be other genes that are expressed in a plasmid or are delivered as proteins in combination with the plasmid above in the vaccine. The adjuvant can be selected from α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MEW, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof. In an exemplary embodiment, the adjuvant is IL-12.

Other genes which can be useful adjuvants include those encoding: MCP-1, MIP-1a MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and/or functional fragments thereof.

6. COMBINATIONAL VACCINES FOR TREATING PARTICULAR CANCERS

The vaccine can be in the form of various combinations of the cancer antigens as described above to treat particular cancers or tumors. Depending upon the combination of one or more cancer antigens, various cancers or other tumor types may be targeted with the vaccine. These cancers can include melanoma, blood cancers (e.g., leukemia, lymphoma, myeloma), lung carcinomas, esophageal squamous cell carcinomas, bladder cancer, colorectal cancer, esophagus, gastric cancer, hepatocarcinoma, head and neck, brain, anal cancer, non-small cell lung carcinoma, pancreatic cancer, synovial carcinoma, prostate cancer, testicular cancer, liver cancer, cervical cancer, recurrent respiratory papillomatosis, skin cancer and stomach cancer.

a. Melanoma

The vaccine can combine one or more cancer antigens such as tyrosinase, PRAME, or GP100-Trp2 to treat or prevent melanoma. The vaccine can further combine one or more of cancer antigen tyrosinase, PRAME, and GP100-Trp2 with any one or more cancer antigens MAGE-A, NY-ESO-1, hTERT, and WT1 for treating or preventing melanoma. Other combinations of cancer antigens may also be applied for treating or preventing melanoma.

b. Head and Neck Cancer

The vaccine can comprise cancer antigen HPV 16 E6/E7 to treat or prevent head and neck cancer. The vaccine can further combine cancer antigen HPV 16 E6/E7 with any one or more of cancer antigens MAGE-A, NY-ESO-1, MAGE-A1, and WT1 for treating or preventing head and neck cancer. Other combinations of cancer antigens may also be applied for treating or preventing head and neck cancer.

c. Recurrent Respiratory Papillomatosis/Anal Cancer

The vaccine can combine one or more cancer antigens such as HPV 6, HPV11, and HPV 16 to treat or prevent recurrent respiratory papillomatosis and/or anal cancer. The vaccine can further combine one or more cancer antigens HPV 6, HPV11 and HPV16 with one or more cancer antigens MAGE-A, NY-ESO-1, MAGE-A1, and WT1 for treating or preventing recurrent respiratory papillomatosis and/or anal cancer. Other combinations of cancer antigens may also be applied for treating or preventing recurrent respiratory papillomatosis and/or anal cancer.

d. Cervical Cancer

The vaccine can combine one or more cancer antigens such as HPV 16 E6/E7 and HPV 18 E6/E7 to treat or prevent cervical cancer. The vaccine can further combine one or more cancer antigens such as HPV 16 E6/E7 and HPV 18 E6/E7 with one or more cancer antigens such as MAGE-A, NY-ESO-1, hTERT, and WT1 for treating or preventing cervical cancer. Other combinations of cancer antigens may also be applied for treating or preventing cervical cancer.

e. Liver Cancer

The vaccine can combine one or more cancer antigens such as HBV core antigen, HBV surface antigen, HCVNS34A, HCVNS5A, HCV NS5B, and HCVNS4B to treat or prevent liver cancer. The vaccine can further combine one or more cancer antigens HBV core antigen, HBV surface antigen, HCVNS34A, HCVNS5A, HCV NS5B, and HCVNS4B with one or more of cancer antigens MAGE-A, NY-ESO-1, hTERT, and WT1 for treating or preventing liver cancer. Other combinations of cancer antigens may also be applied for treating or preventing liver cancer.

f. Glioblastoma

The vaccine can comprise CMV to treat or prevent glioblastoma. The vaccine can further combine CMV with one or more of cancer antigens hTERT, NY-ESO-1, MAGE-A, or WT1 for treating or preventing glioblastoma. Other combinations of cancer antigens may also be applied for treating or preventing glioblastoma.

g. Prostate

The vaccine can combine one or more cancer antigens such as PSA, PSMA, and

STEAP to treat or prevent prostate cancer. The vaccine can further combine one or more cancer antigens PSA, PSMA, and STEAP with one or more of cancer antigens hTERT, NY-ESO-1, MAGE-A, and WT1 for treating or preventing prostate cancer. Other combinations of cancer antigens may also be applied for treating or preventing prostate cancer.

h. Blood Cancers (e.g., Leukemia, Lymphoma, Myeloma)

The vaccine can combine one or more cancer antigens such as PRAME, WT-1, and MAGE-A to treat or prevent blood cancers such as leukemia, lymphoma and myeloma. The vaccine can further combine one or more cancer antigens PRAME, WT-1, and MAGE-A with one or more of cancer antigens NY-ESO-1, and hTERT for treating or preventing blood cancers such as leukemia, lymphoma and myeloma. Other combinations of cancer antigens may also be applied for treating or preventing blood cancers such as leukemia, lymphoma and myeloma cancer.

7. METHOD OF VACCINATION

Provided herein is a method for treating or preventing cancer using the pharmaceutical formulations for providing genetic constructs and proteins of the one or more cancer antigens as described above, which comprise epitopes that make them particularly effective immunogens against which an immune response to the one or more cancer antigens can be induced. The method of administering the vaccine, or vaccination, can be provided to induce a therapeutic and/or prophylactic immune response. The vaccination process can generate in the mammal an immune response against one or more of the cancer antigens as disclosed herein. The vaccine can be administered to an individual to modulate the activity of the mammal's immune system and enhance the immune response. The administration of the vaccine can be the transfection of the one or more cancer antigens as disclosed herein as a nucleic acid molecule that is expressed in the cell and thus, delivered to the surface of the cell upon which the immune system recognizes and induces a cellular, humoral, or cellular and humoral response. The administration of the vaccine can be used to induce or elicit an immune response in mammals against one or more of the cancer antigens as disclosed herein by administering to the mammals the vaccine as discussed herein.

Upon administration of the vaccine to the mammal, and thereupon the vector into the cells of the mammal, the transfected cells will express and secrete one or more of the cancer antigens as disclosed herein. These secreted proteins, or synthetic antigens, will be recognized as foreign by the immune system, which will mount an immune response that can include antibodies made against the one or more cancer antigens, and a T-cell response specifically against the one or more cancer antigens. In some examples, a mammal vaccinated with the vaccines discussed herein will have a primed immune system and when challenged with the one or more cancer antigens as disclosed herein, the primed immune system will allow for rapid clearing of subsequent cancer antigens as disclosed herein, whether through the humoral, cellular, or both cellular and humoral immune response. The vaccine can be administered to an individual to modulate the activity of the individual's immune system, thereby enhancing the immune response.

Methods of administering the DNA of a vaccine are described in U.S. Pat. Nos. 4,945,050 and 5,036,006, both of which are incorporated herein in their entirety by reference.

The vaccine can be administered to a mammal to elicit an immune response in a mammal. The mammal can be human, non-human primate, cow, pig, sheep, goat, antelope, bison, water buffalo, bovids, deer, hedgehogs, elephants, llama, alpaca, mice, rats, or chicken. In an exemplary embodiment, the vaccine can be administered to a mammal.

The vaccine dose can be between 1 µg to 10 mg active component/kg body weight/time and can be 20 µg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, 10, or more doses.

a. Method of Generating an Immune Response with the Vaccine

The vaccine can be used to generate an immune response in a mammal, including a therapeutic or prophylactic immune response. The immune response can generate antibodies and/or killer T cells which are directed to the one or more cancer antigens as disclosed herein. Such antibodies and T cells can be isolated.

Some embodiments provide methods of generating immune responses against one or more of the cancer antigens as disclosed herein, which comprise administering to an individual the vaccine. Some embodiments provide methods of prophylactically vaccinating an individual against a cancer or tumor expressing one or more of the cancer antigens as described above, which comprise administering the vaccine. Some embodiments provide methods of therapeutically vaccinating an individual that has been suffering from the cancer or tumor expressing one or more of the cancer antigens, which comprise administering the vaccine. Diagnosis of the cancer or tumor expressing the one or more cancer antigens as disclosed herein prior to administration of the vaccine can be performed routinely.

b. Method of Cancer Treatment with the Vaccine

The vaccine can be used to generate or elicit an immune response in a mammal that is reactive or directed to a cancer or tumor (e.g., melanoma, head and neck, cervical, liver, prostate, blood cancers, esophageal squamous, gastric) of the mammal or subject in need thereof. The elicited immune response can prevent cancer or tumor growth.

The elicited immune response can prevent and/or reduce metastasis of cancerous or tumor cells. Accordingly, the vaccine can be used in a method that treats and/or prevents cancer or tumors in the mammal or subject administered the vaccine. Depending upon the antigen used in the vaccine, the treated cancer or tumor based growth can be any type of cancer such as, but not limited to, melanoma, blood cancers (e.g., leukemia, lymphoma, myeloma), lung carcinomas, esophageal squamous cell carcinomas, bladder cancer, colorectal cancer, esophagus, gastric cancer, hepatocarcinoma, head and neck, brain, anal cancer, non-small cell lung carcinoma, pancreatic cancer, synovial carcinoma, prostate cancer, testicular cancer, liver cancer, cervical cancer, recurrent respiratory papillomatosis, skin cancer and stomach cancer.

In some embodiments, the administered vaccine can mediate clearance or prevent growth of tumor cells by inducing (1) humoral immunity via B cell responses to generate antibodies that block monocyte chemoattractant protein-1 (MCP-1) production, thereby retarding myeloid derived suppressor cells (MDSCs) and suppressing tumor growth; (2) increase cytotoxic T lymphocyte such as $CD8^+$ (CTL) to attack and kill tumor cells; (3) increase T helper cell responses; (4) and increase inflammatory responses via IFN-$\gamma$ and TFN-$\alpha$ or preferably all of the aforementioned.

In some embodiments, the immune response can generate a humoral immune response and/or an antigen-specific cytotoxic T lymphocyte (CTL) response that does not cause damage to or inflammation of various tissues or systems (e.g., brain or neurological system, etc.) in the subject administered the vaccine.

In some embodiments, the administered vaccine can increase tumor free survival, reduce tumor mass, increase tumor survival, or a combination thereof in the subject. The administered vaccine can increase tumor free survival by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% or more in the subject. The administered vaccine can reduce tumor mass by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, and 70% or more in the subject after immunization. The administered vaccine can prevent and block increases in monocyte chemoattractant protein 1 (MCP-1), a cytokine secreted by myeloid derived suppressor cells, in the subject. In some embodiments, the administered vaccine can prevent and block increases in MCP-1 within the cancerous or tumor tissue in the subject, thereby reducing vascularization of the cancerous or tumor tissue in the subject.

The administered vaccine can increase tumor survival by 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, and 70% or more in the subject. In some embodiments, the vaccine can be administered to the periphery (as described in more detail below) to establish an antigen-specific immune response targeting the cancerous or tumor cells or tissue to clear or eliminate the cancer or tumor expressing the one or more cancer antigens without damaging or causing illness or death in the subject administered the vaccine.

The administered vaccine can increase a cellular immune response in the subject by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold. In some embodiments, the administered vaccine can increase the cellular immune response in the subject by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold.

The administered vaccine can increase interferon gamma (IFN-$\gamma$) levels in the subject by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold. In some embodiments, the administered vaccine can increase IFN-$\gamma$ levels in the subject by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold.

The vaccine dose can be between 1 µg to 10 mg active component/kg body weight/time and can be 20 µg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, or 10.

(1) Combinational Therapies with PD-1 and/or PD-L1 Antibodies

The present invention is also directed to a method of increasing an immune response in a mammal using the vaccine as described above. The vaccine as described above can comprise the cancer antigen and a PD1 antibody and/or PDL1 antibody as described above. The combination can be in a single formulation or can be separate and administered in sequence (either cancer antigen first and then PD1 antibody and/or PDL1 antibody, or PD1 antibody and/or PDL1 antibody first and then cancer antigen). In some embodiments, the cancer antigen can be administered to the subject about 30 seconds, 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 60 minutes, 0.25 hours, 0.5 hours, 0.75 hours, 1 hours, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours, 60 hours, 72 hours, 84 hours, 96 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 1 week, 2 weeks, 3 weeks, 4 weeks, 5 weeks, 6 weeks, 7 weeks, or 8 weeks before the PD-1 antibody and/or PD-L1 antibody is administered to the subject. In other embodiments, the PD-1 antibody and/or PD-L1 antibody can be administered to the subject about 30 seconds, 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 60 minutes, 0.25 hours, 0.5 hours, 0.75 hours, 1 hours, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours, 60 hours, 72 hours, 84 hours, 96 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 1 week, 2 weeks, 3 weeks, 4 weeks, 5 weeks, 6 weeks, 7 weeks, or 8 weeks before the cancer antigen is administered to the subject.

The combination of the cancer antigen and PD1 antibody and/or PDL1 antibody induces the immune system more efficiently than a vaccine comprising the cancer antigen alone. This more efficient immune response provides increased efficacy in the treatment and/or prevention of a particular cancer. Depending upon the antigen used in the vaccine combined with the PDL1 antibody or PD1 antibody, the treated cancer or tumor based growth can be any type of cancer such as, but not limited to, melanoma, blood cancers (e.g., leukemia, lymphoma, myeloma), lung carcinomas, esophageal squamous cell carcinomas, bladder cancer, colorectal cancer, esophagus, gastric cancer, hepatocarcinoma, head and neck, brain, anal cancer, non-small cell lung carcinoma, pancreatic cancer, synovial carcinoma, prostate cancer, testicular cancer, liver cancer, cervical cancer, recurrent respiratory papillomatosis, skin cancer and stomach cancer.

In some embodiments, the immune response can be increased by about 0.5-fold to about 15-fold, about 0.5-fold to about 10-fold, or about 0.5-fold to about 8-fold. Alternatively, the immune response in the subject administered the vaccine can be increased by at least about 0.5-fold, at least about 1.0-fold, at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, or at least about 15.0-fold.

In still other alternative embodiments, the immune response in the subject administered the vaccine can be increased about 50% to about 1500%, about 50% to about 1000%, or about 50% to about 800%. In other embodiments, the immune response in the subject administered the vaccine can be increased by at least about 50%, at least about 100%, at least about 150%, at least about 200%, at least about 250%, at least about 300%, at least about 350%, at least about 400%, at least about 450%, at least about 500%, at least about 550%, at least about 600%, at least about 650%, at least about 700%, at least about 750%, at least about 800%, at least about 850%, at least about 900%, at least about 950%, at least about 1000%, at least about 1050%, at least about 1100%, at least about 1150%, at least about 1200%, at least about 1250%, at least about 1300%, at least about 1350%, at least about 1450%, or at least about 1500%.

The vaccine dose can be between 1 µg to 10 mg active component/kg body weight/time, and can be 20 µg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, or 10.

(2) Melanoma

The vaccine can be used to generate or elicit an immune response in a mammal that is reactive or directed to melanoma in the mammal or subject in need thereof. The elicited immune response can prevent melanoma growth. The elicited immune response can reduce melanoma growth. The elicited immune response can prevent and/or reduce metastasis of cancerous or tumor cells from a melanoma. Accordingly, the vaccine can be used in a method that treats and/or prevents melanoma in the mammal or subject administered the vaccine.

In some embodiments, the administered vaccine can mediate clearance or prevent growth of melanoma cells by inducing (1) humoral immunity via B cell responses to generate antibodies that block monocyte chemoattractant protein-1 (MCP-1) production, thereby retarding myeloid derived suppressor cells (MDSCs) and suppressing melanoma growth; (2) increase cytotoxic T lymphocyte such as $CD8^+$ (CTL) to attack and kill melanoma cells; (3) increase T helper cell responses; and (4) increase inflammatory responses via IFN-γ and TFN-α or all of the aforementioned.

In some embodiments, the administered vaccine can increase melanoma free survival, reduce melanoma mass, increase melanoma survival, or a combination thereof in the subject. The administered vaccine can increase melanoma free survival by 30%, 31%, 32%, 33%, 34%, 35%, 36%, 37%, 38%, 39%, 40%, 41%, 42%, 43%, 44%, and 45% or more in the subject. The administered vaccine can reduce melanoma mass by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% or more in the subject after immunization. The administered vaccine can prevent and block increases in monocyte chemoattractant protein 1 (MCP-1), a cytokine secreted by myeloid derived suppressor cells, in the subject. In some embodiments, the administered vaccine can prevent and block increases in MCP-1 within the melanoma tissue in the subject, thereby reducing vascularization of the melanoma tissue in the subject. The administered vaccine can increase melanoma survival by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% or more in the subject.

8. ROUTES OF ADMINISTRATION

The vaccine or pharmaceutical composition can be administered by different routes including orally, parenterally, sublingually, transdermally, rectally, transmucosally, topically, via inhalation, via buccal administration, intrapleurally, intraarterial, intraperitoneal, subcutaneous, intramuscular, intranasal, intrathecal, and intraarticular or combinations thereof. For veterinary use, the composition can be administered as a suitably acceptable formulation in accordance with normal veterinary practice. The veterinarian can readily determine the dosing regimen and route of administration that is most appropriate for a particular animal. The vaccine can be administered by traditional syringes, needleless injection devices, "microprojectile bombardment gene guns", or other physical methods such as electroporation ("EP"), "hydrodynamic method", or ultrasound.

The vector of the vaccine can be administering to the mammal by several well-known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The one or more cancer antigens of the vaccine can be administered via DNA injection and along with in vivo electroporation.

a. Electroporation

The vaccine or pharmaceutical composition can be administered by electroporation. Administration of the vaccine via electroporation can be accomplished using electroporation devices that can be configured to deliver to a desired tissue of a mammal a pulse of energy effective to cause reversible pores to form in cell membranes, and preferable the pulse of energy is a constant current similar to a preset current input by a user. The electroporation device can comprise an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation can be accomplished using an in vivo electroporation device, for example CELLECTRA® EP system (Inovio Pharmaceuticals, Inc., Blue Bell, PA) or Elgen electroporator (Inovio Pharmaceuticals, Inc.) to facilitate transfection of cells by the plasmid.

Examples of electroporation devices and electroporation methods that can facilitate administration of the DNA vaccines of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that can be used for facilitating administration of the DNA vaccines include those provided in U.S. patent application Ser. No. 11/874,072, filed Oct. 17, 2007, which claims the benefit under 35 USC 119(e) to U.S. Provisional Application Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems can comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then administered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference in its entirety.

U.S. Patent Pub. 2005/0052630 submitted by Smith, et al. describes an electroporation device which can be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby fully incorporated by reference.

The electrode arrays and methods described in U.S. Pat. No. 7,245,963 and U.S. Patent Pub. 2005/0052630 can be adapted for deep penetration into not only tissues such as muscle, but also other tissues or organs. Because of the configuration of the electrode array, the injection needle is also inserted completely into the target organ, and the injection is administered perpendicular to the target issue, in the area that is pre-delineated by the electrodes. The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns administration of DNA using any of a variety of devices, and U.S. Pat. No. 7,328,064 issued Feb. 5, 2008, drawn to method of injecting DNA are contemplated herein. The above-mentioned patents are incorporated by reference in their entirety.

9. METHOD OF PREPARING THE VACCINE

Provided herein are methods for preparing the DNA plasmids that comprise the vaccines discussed herein. The DNA plasmids, after the final subcloning step into the mammalian expression plasmid, can be used to inoculate a cell culture in a large-scale fermentation tank, using known methods in the art.

The DNA plasmids for use with the EP devices of the present invention can be formulated or manufactured using a combination of known devices and techniques, but preferably they are manufactured using an optimized plasmid manufacturing technique that is described in a US published application no. 20090004716, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

The present invention has multiple aspects, illustrated by the following non-limiting examples.

10. EXAMPLES

Example 1

Figure 1C:
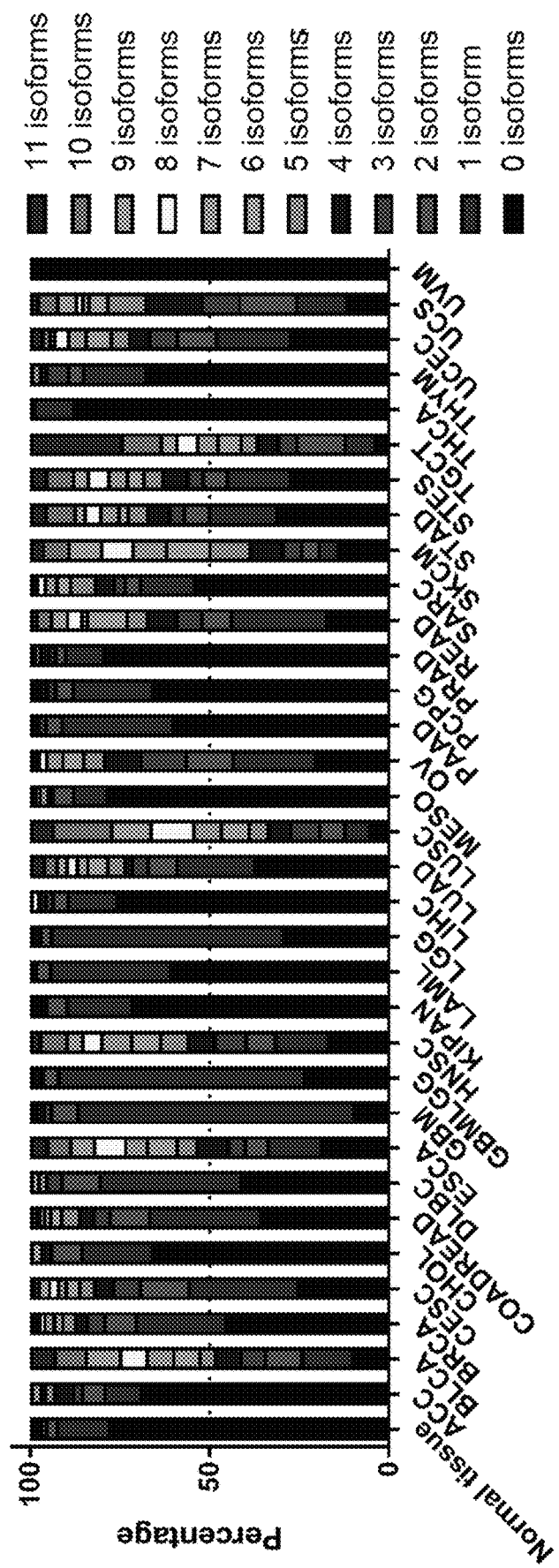

A Designer Cross-Reactive DNA Immunotherapeutic Vaccine that Targets Multiple Mage-A Family Members Simultaneously for Cancer Therapy The data presented herein analyzes MAGE-A RNA expression in The Cancer Genome Atlas and shows that a high proportion of patients express multiple MAGE-A isoforms, not limited to MAGE-A3, simultaneously in diverse tumors. Thus, optimized consensus MAGE-A DNA vaccine was designed which is capable of cross-reacting with many MAGE-A isoforms. Immunization of this MAGE-A vaccine by electroporation in C57Bl/6 mice, generated robust IFN-γ and TNF-α CD8+ T cell responses as well as cytotoxic CD107a/IFN-γ/T-bet triple-positive responses against multiple isoforms. The potency and cross-reactivity of this MAGE-A DNA immunogen were analyzed in genetically diverse, outbred mice, and 14 out of 15 of these mice mounted a cross-reactive immune response. The anti-tumor activity of this MAGE-A DNA vaccine was tested in Tyr::CreER;BRAF$^{Ca/+}$;Pten$^{lox/lox}$ transgenic mice that develop melanoma upon tamoxifen induction. The MAGE-A DNA therapeutic vaccine significantly slowed tumor growth doubled median mouse survival. These results support the further study of MAGE-A consensus vaccines in cancer immunotherapy Various MAGE-A family members have shown to be up-regulated in many different human cancers, including non-small cell lung cancer, melanoma, breast cancer, ovarian cancer, colon cancer, multiple myeloma, hepatocellular carcinoma, and others (Roeder et al., 2005, Arch Dermatol Res 296:314-9; Tajima et al., 2003, Lung cancer 42:23-33; Jungbluth et al., 2005, Blood 106:167-74). However, there are important limitations for distinguishing between different human MAGE-A isoforms by immunohistochemistry or western blot due to structural homology and cross-reactivity of available antibodies. To achieve a more global picture of MAGE-A isoform expression in human cancers, human patient RNA-seq data from the Cancer Genome Atlas (TCGA) was analyzed. Normalized RSEM counts were downloaded through the GDAC data portal for all human tumors and matched normal samples available (gdac.broadinstitute.org/). Log-transformed data was used for analysis. The threshold for expression was set to be greater than 2 standard deviations above the mean for the normal tissue control group for each isoform individually. Despite the fact that most immune therapies target the MAGE-A3 isoform, the other 10 isoforms are also highly expressed in a variety of human cancers (FIG. 1A). When examining all human cancer samples available from the GDAC data portal, tumors that express each isoform range from 9.5% (MAGE-A8) to 29.5% (MAGE-A12) (FIG. 1B). Expression of MAGE-A isoforms were particularly high for patients with bladder cancer, esophageal cancer, glioblastoma, head and neck cancer, lung squamous cell carcinoma, rectum adenocarcinoma, skin cutaneous melanoma, testicular germ center tumors, and uterine carcinosarcoma (FIG. 1A). Importantly, over 80% of patients with these tumor types show expression of one or more MAGE-A isoforms. It was common for patients to express multiple MAGE-A isoforms simultaneously (FIG. 1C). For instance, over half of patients with lung squamous cell carcinoma (LUSC), skin cutaneous melanoma (SKCM) or testicular germ center tumors (TGCT) show expression of more than 5 MAGE-A isoforms simultaneously (FIG. 1C). This analysis indicates that an immune therapy targeting multiple MAGE-A isoforms, not just MAGE-A3, would likely be beneficial for a large proportion of patients.

MAGE-A Vaccine Design and Expression

Figure 2A:
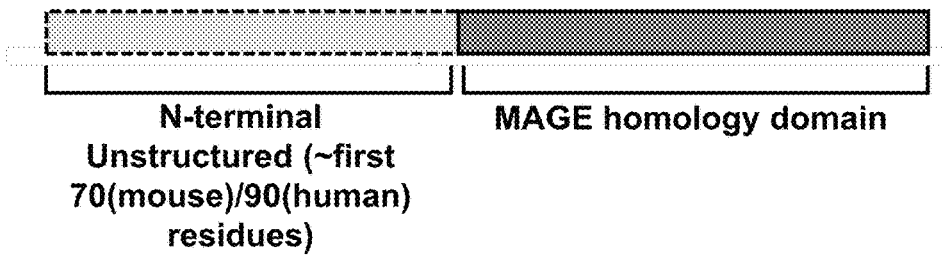
FIG. 2A through FIG. 2F, depicts the design of mouse and human consensus MAGE-A vaccines.
Figure 2B:
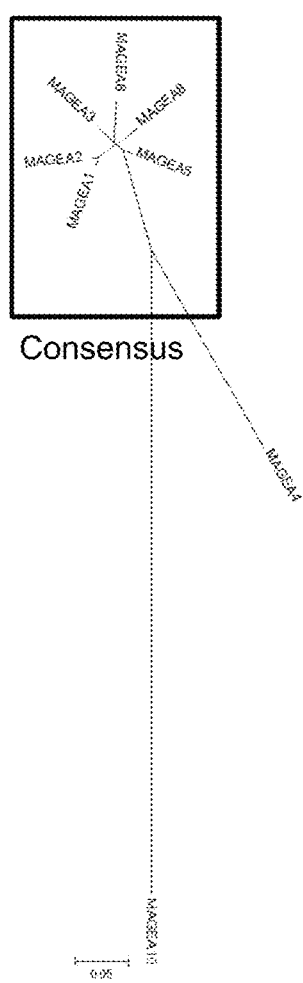
Figure 2C:
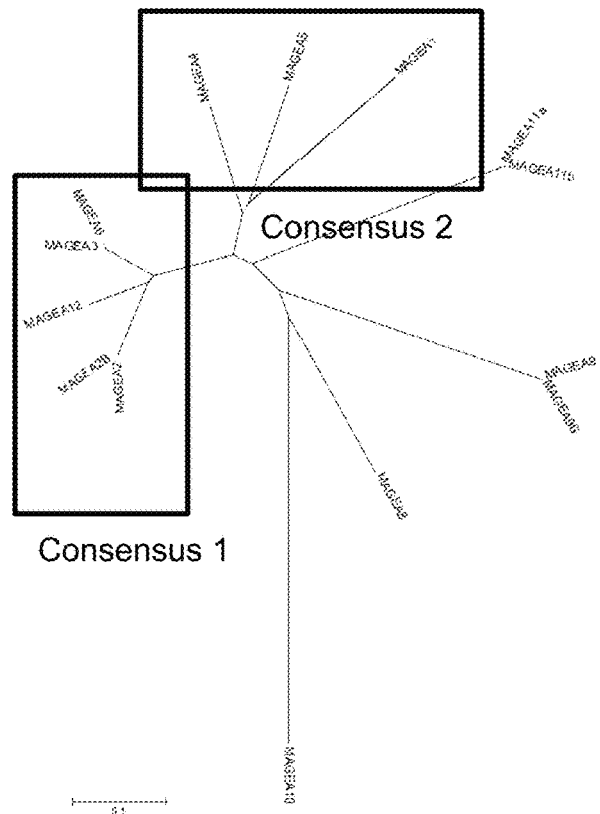
Figure 2D:
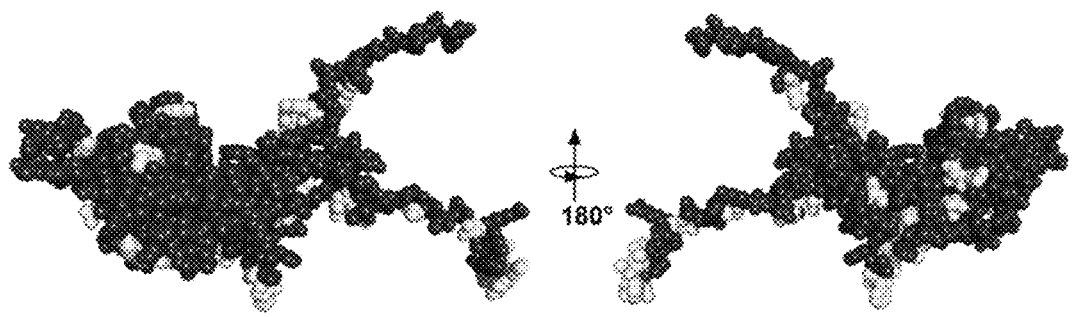
Figure 2E:
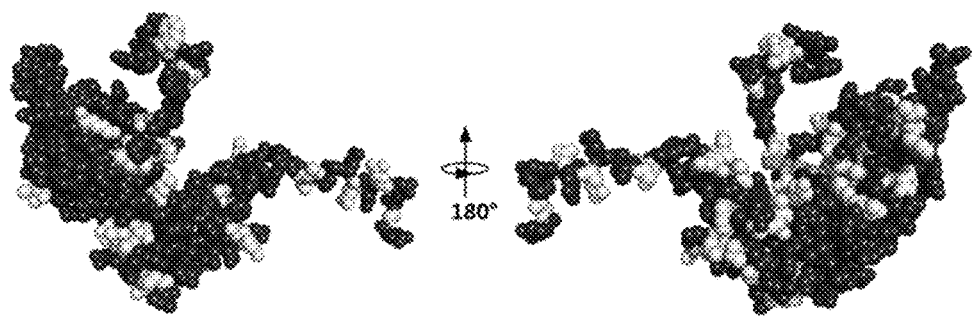
Figure 2F:
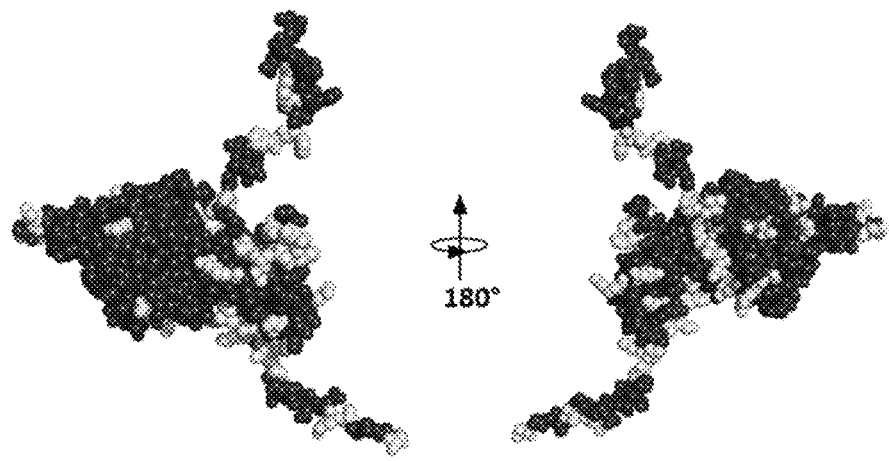

The MAGE-A family does exist in lower vertebrates, and the general domain structure of this antigen family is conserved between mouse and human, with an unstructured N-terminal domain and a MAGE homology domain (FIG. 2A). However, the sequence is poorly conserved. The mouse and human MAGE-A genes share between 25.3% (MAGE-A2) to 38.4% (MAGE-A10) identity at the protein level (calculated using sequence alignment with ClustalX2). Furthermore, the MAGE-A9, MAGE-A11 and MAGE-A12 isoforms have not been identified in mice. There separate vaccines were designed for testing in mice and for preclinical development for humans. A synthetic consensus MAGE-A vaccine was designed for proof-of-concept experiments in mice that shares 94.1% identity with MAGE-A1, 95.1% identity with MAGE-A2, 94.5% identity with MAGE-A3, 96.8% identity with MAGE-A5, 91% identity with MAGE-A6 and 94.8% identity with MAGE-A8 (FIG. 2B,D). For pre-clinical development for humans, two consensus MAGE-A vaccines were generated. The human MAGE-A consensus #1 shares 91.4% identity to human MAGE-A2, 92.7% identity to MAGE-A3, 92.4% identity to MAGE-A6 and 92% identity to MAGE-A12. The human MAGE-A consensus #2 shares 84.6% identity to MAGE-A1, 84.6% identity to MAGE-A4, and 86.3% identity to MAGE-A5 (FIG. 2C,E,F). These homologies were chosen as they would allow for theoretical T cell cross-reactivity for the majority of possible MAGE-A T cell epitopes. All of these vaccines were RNA and codon optimized for efficient translation and include the IgE leader sequence which promotes protein production and secretion.

Figure 8:
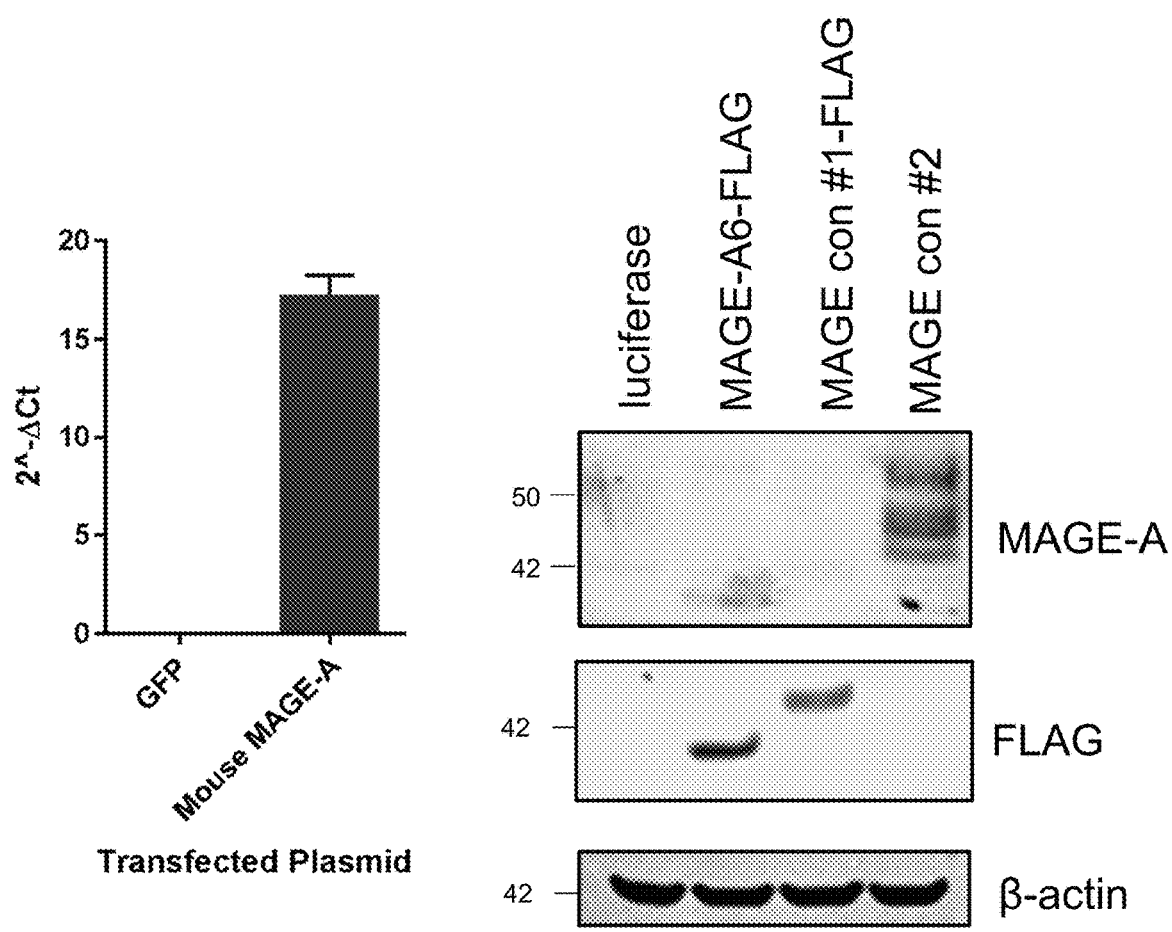
FIG. 8 depicts experimental results demonstrating the expression of human and mouse consensus MAGE-A plasmids in vitro.
Figure 8:
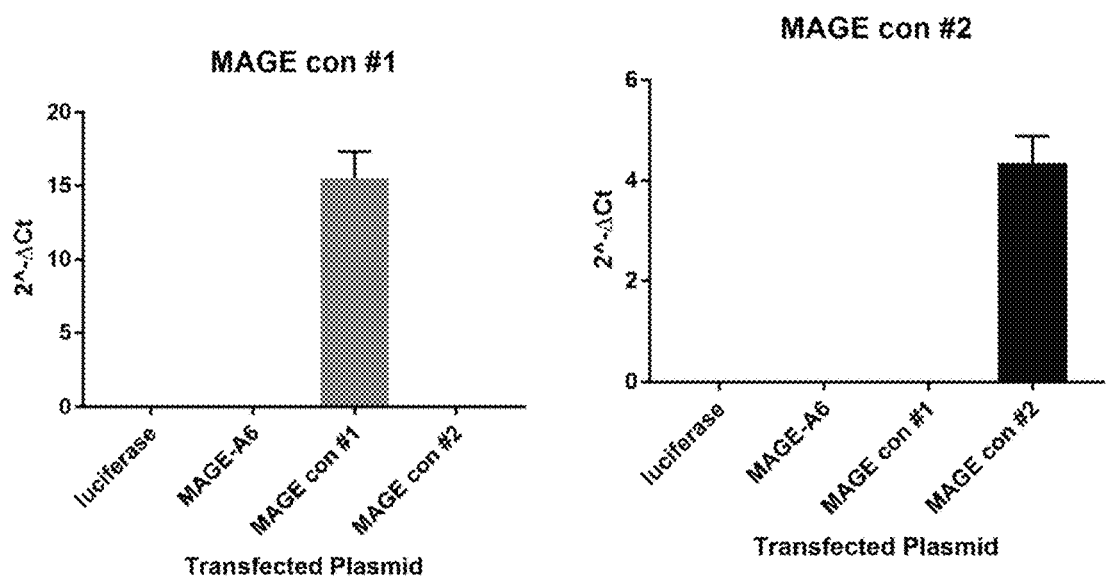

Next plasmid vaccine expression in vitro was tested. 293T cells were transfected with the mouse consensus MAGE-A vaccine or a GFP expressing plasmid as a control. Because there are no commercially available antibodies that recognize mouse MAGE-A isoforms, expression was determined using qPCR. There was robust expression of the consensus mouse MAGE-A vaccine in 293T cells in vitro (FIG. 8A). Next expression of the human MAGE-A consensus #1 and consensus #2 plasmids were tested. Robust expression of these plasmids by qPCR was detected (FIG. 8B). Expression of these plasmids was also detected by western blot, using either a Pan-MAGE-A antibody or a FLAG antibody that recognizes FLAG-tagged constructs (FIG. 8C). The Pan-MAGE-A antibody was able to recognize the MAGE-A Consensus #2 vaccine construct, but not the Consensus #1 construct. As a control, 293T cells that were transfected with a human MAGE-A6 plasmid were included, which is slightly smaller than the MAGE-A consensus #1 or consensus #2 plasmids by western blot (FIG. 8C). This size shift is likely due to the addition of the IgE leader sequence.

Figures 3A, 3B, 3C, 3D, 3E, 3F:
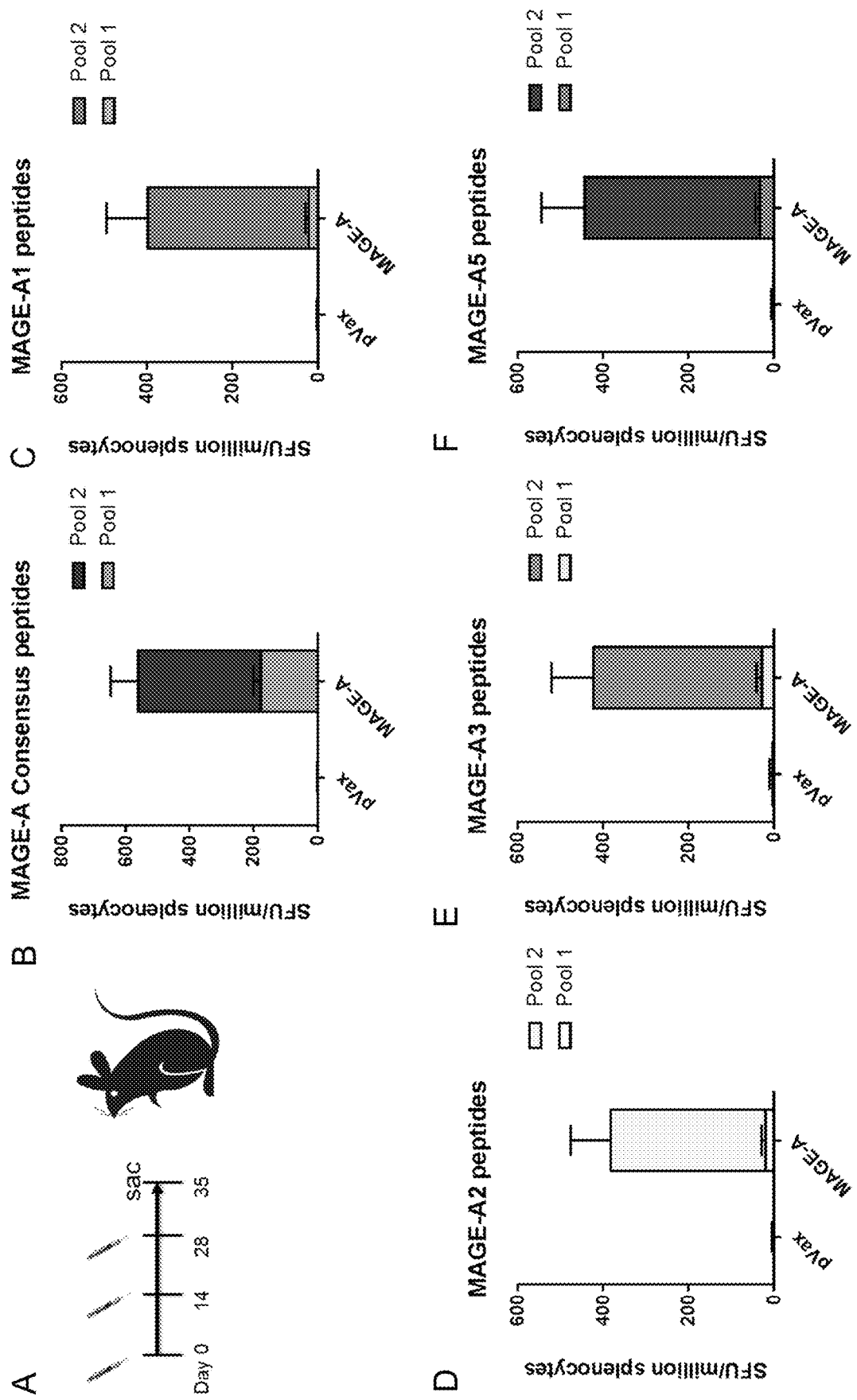
FIG. 3A through FIG. 3K, depicts experimental results demonstrating that consensus mouse MAGE-A vaccine breaks tolerance to multiple MAGE-A family members in C57Bl/6 mice.
Figures 3G, 3H, 3I, 3J, 3K:
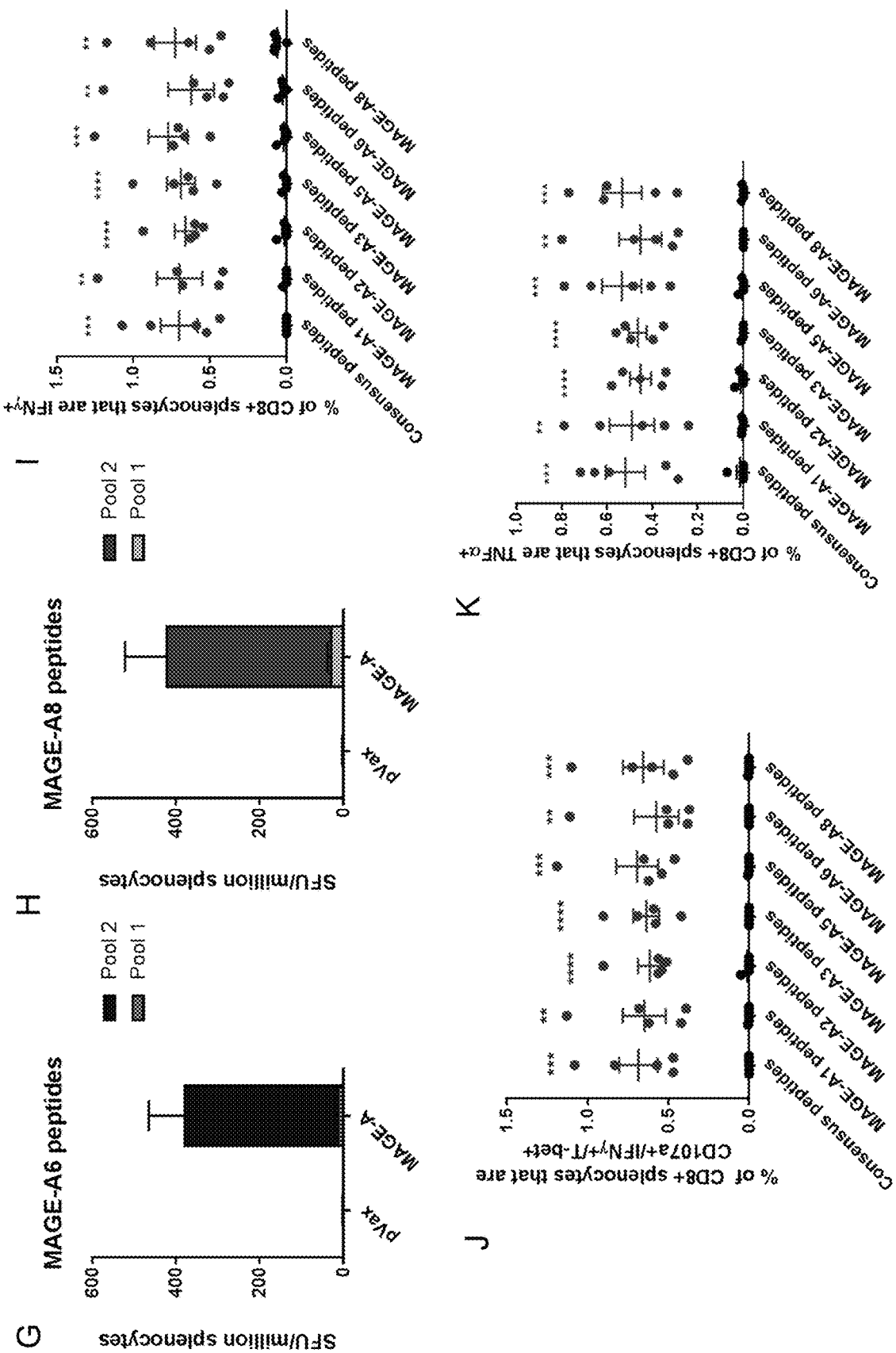
Figure 9:
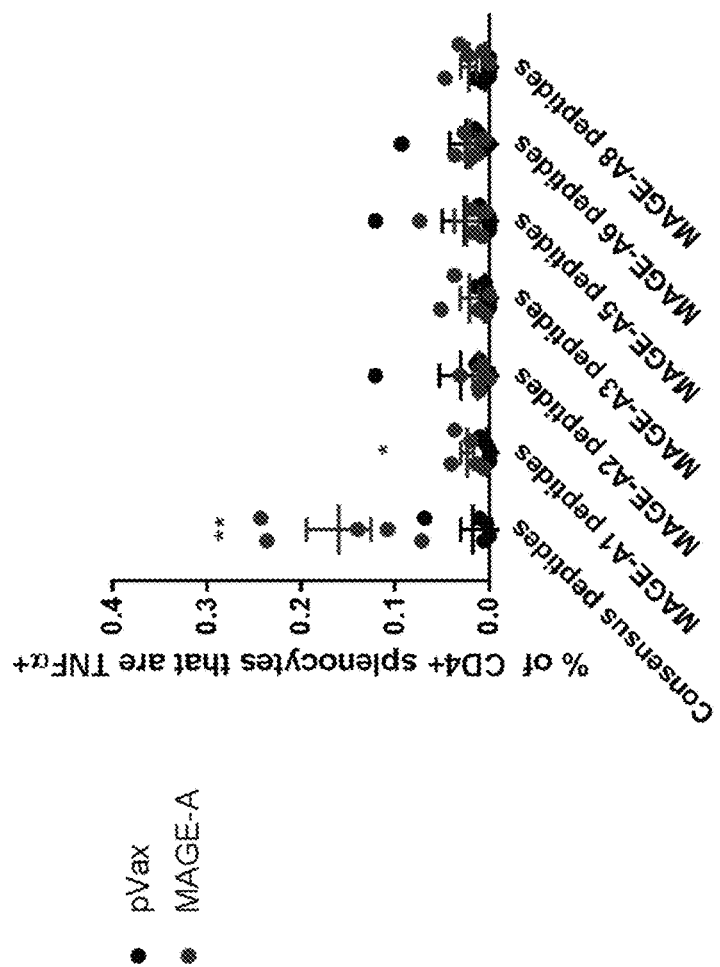
FIG. 9 depicts experimental results demonstrating that consensus mouse MAGE-A vaccine is a poor inducer of CD4+ T cells in C57Bl/6 mice.
Figure 9:
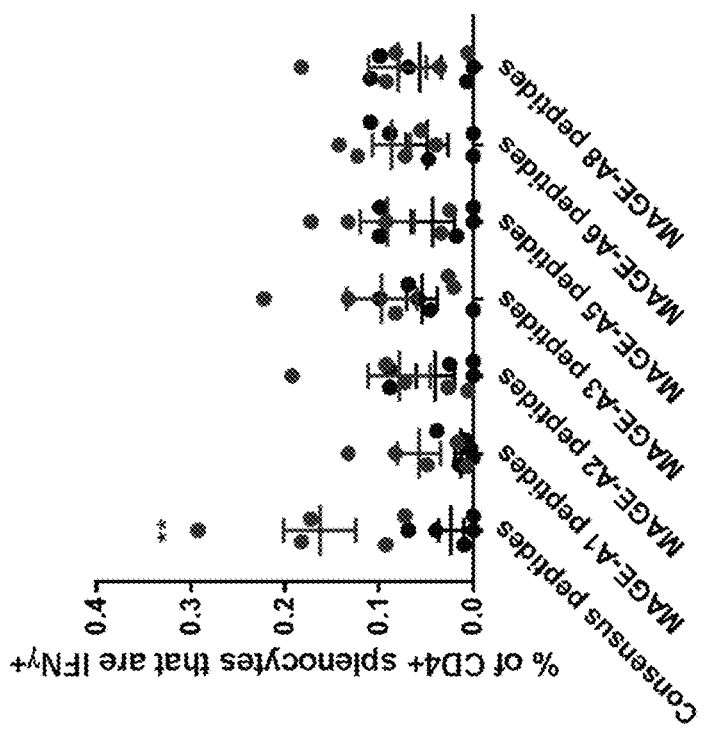

Consensus Mouse MAGE-A Vaccine Breaks Tolerance to Multiple MAGE-A Isoforms in C57Bl/6 Mice To test the capacity of the mouse MAGE-A vaccine to break tolerance to multiple MAGE-A isoforms, C57Bl/6 mice were immunized with 25 μg of the mouse consensus MAGE-A vaccine three times at two-week intervals and cellular immune responses were assessed one week following the final vaccination (FIG. 3A). The data demonstrates, via IFN-γ ELISpot assay as well as intracellular cytokine staining of splenocytes that were stimulated with mouse native isoform-specific peptides, that the optimized designer vaccine is capable of inducing robust CD8+ IFN-γ responses to all 6 isoforms predicted to cross-react with this vaccine (FIG. 3B-I). Furthermore, nearly all of these antigen-specific CD8+ splenocytes co-expressed the degranulation marker CD107a and the transcription factor T-bet, in addition to IFN-γ, indicating that these CD8+ T cells have high cytolytic potential (FIG. 3J). High levels of TNF-α are also induced in CD8+ T cells upon stimulation of splenocytes with isoform-specific peptides (FIG. 3K). The immune response detected in C57Bl/6 mice was largely driven by CD8+ T cells, as evidenced by the lower level of robust CD4+ T cell response for the individual MAGE-A isoforms (FIG. 9). These data demonstrate that this optimized, synthetic MAGE-A vaccine is capable of breaking tolerance to multiple MAGE-A isoforms simultaneously in mice.

Figure 10:
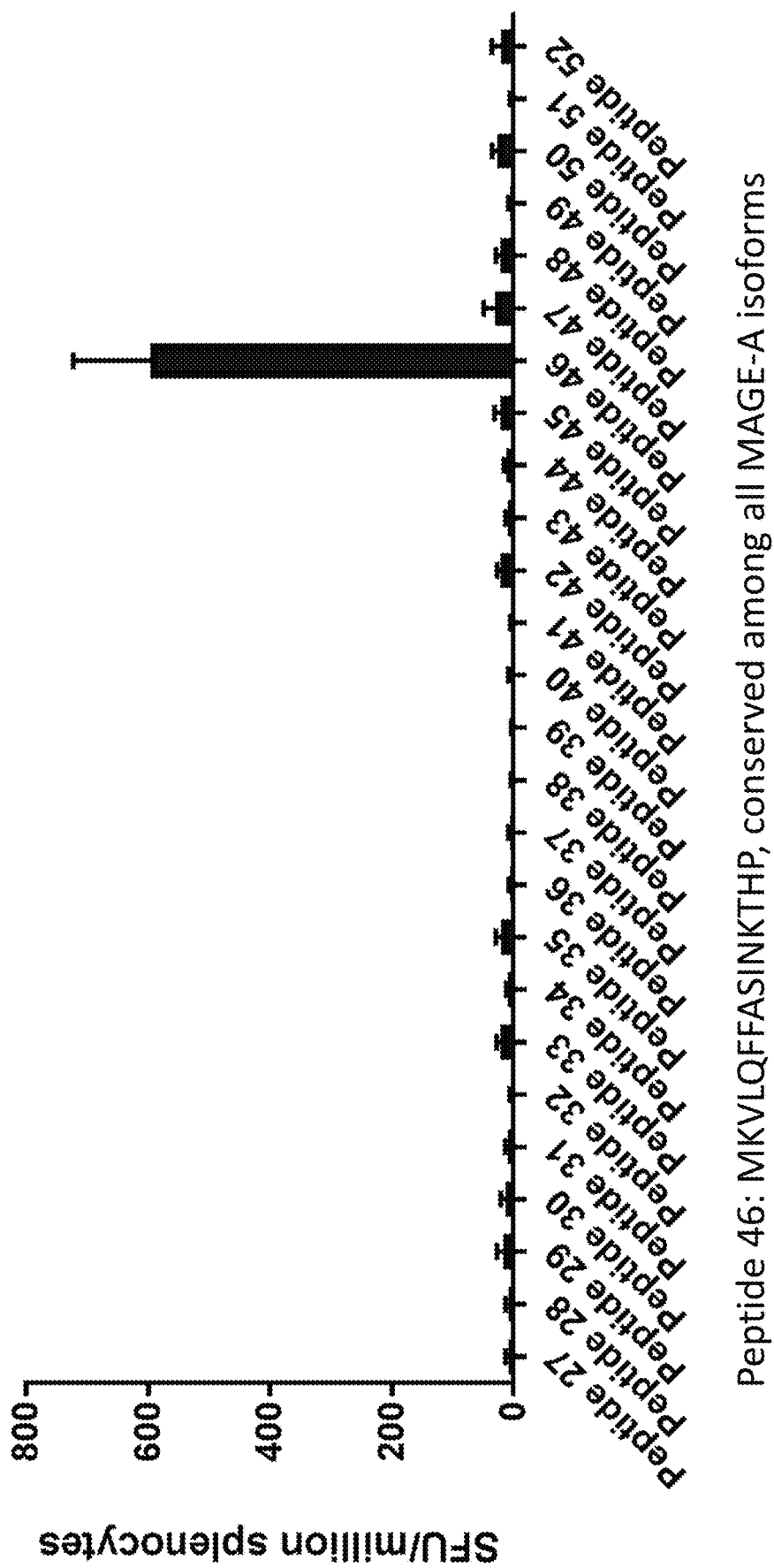
FIG. 10 depicts experimental results demonstrating that consensus mouse MAGE-A vaccine induces immune responses to one dominant epitope.

Because most of the immune responses observed were in peptide Pool 2, IFN-γ ELISpots were ran using the individual peptides that make up Pool 2. By running the individual peptides, it was determined that the response in C57Bl/6 mice was dominated by a single epitope: MKVLQFFASINKTHP (SEQ ID NO:15) (FIG. 10). This epitope contains both an 8-mer (VLQFFASI (SEQ ID NO:16)) and 9-mer (KVLQFFASI (SEQ ID NO:17)) that are predicted to have the highest MHC class I binding affinity (36.8 nM and 20.5 nM IC50, respectively) of all possible mouse MAGE-A epitopes, according to the IEDB NetMHC-Pan prediction program.

Due to potential toxicity concerns related to MAGE-A3 targeted TCR gene therapy, MAGE-A DNA vaccine immunized mice were closely examined for adverse events. Five mice were immunized three times at two week intervals, and were monitored mice for a total of 9 months after the first immunization. No apparent toxicity was observed in these mice upon observation. Upon euthanization and dissection of these mice, no gross organ abnormalities were observed.

Figures 4A, 4B:
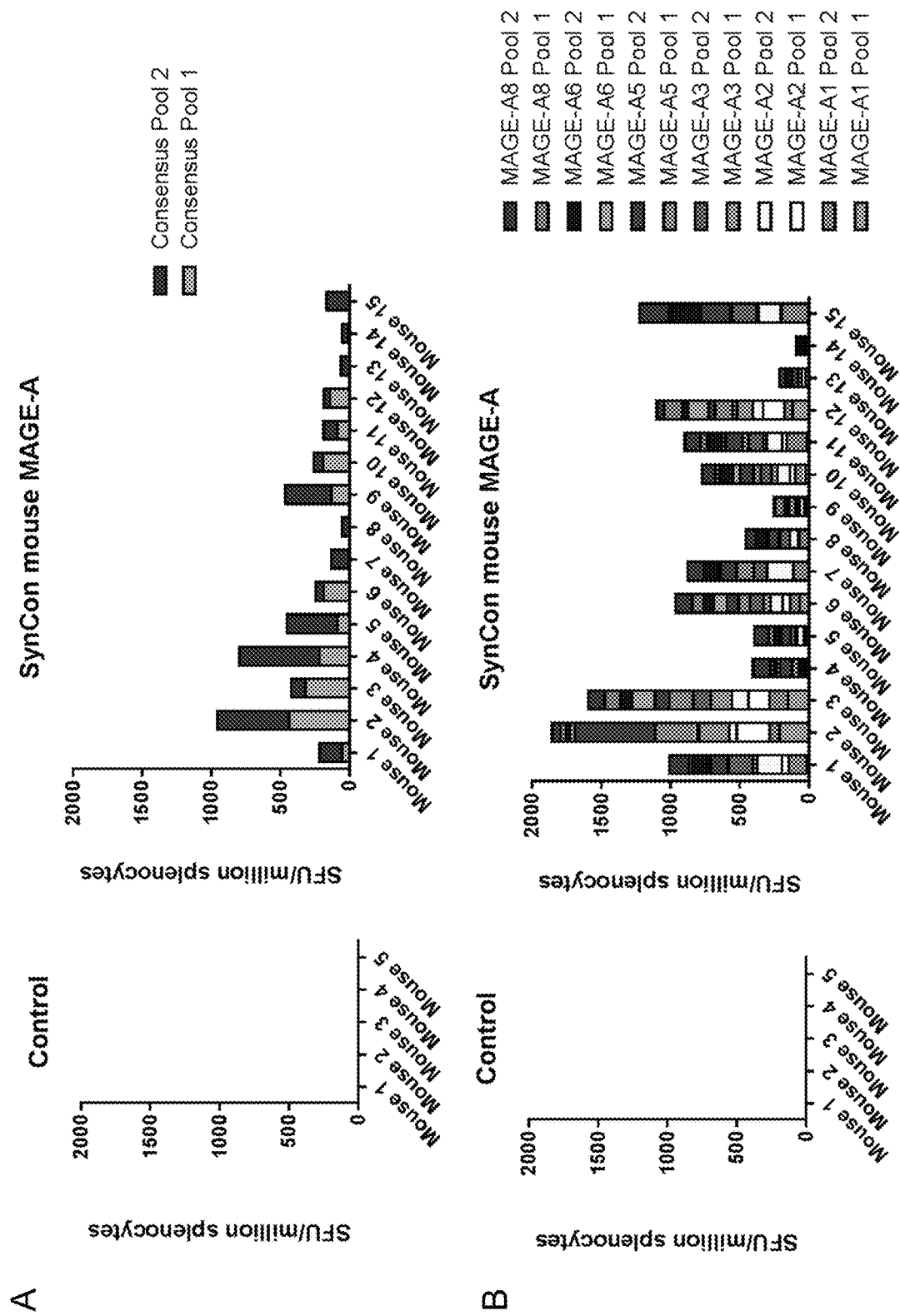
FIG. 4A and FIG. 4B, depicts experimental results demonstrating that consensus mouse MAGE-A vaccine breaks tolerance to multiple MAGE-A isoforms in CD-1 outbred mice. CD-1 outbred mice were immunized 3 times at 2 week intervals and sacrificed 1 week following final vaccination. Mice were immunized with 25 µg of DNA followed by electroporation.

Consensus MAGE-A vaccine breaks tolerance to multiple MAGE-A isoforms in CD-1 outbred mice Because the inbred C57Bl/6 mice responded primarily to one immunodominant epitope, next this consensus mouse MAGE-A vaccine was tested in CD-1 outbred mice to determine if it would generate cross-reactive immune responses in genetically diverse mice. Fifteen CD-1 outbred mice were immunized with 25 μg of the mouse consensus MAGE-A vaccine three times at two-week intervals and cellular immune responses were assessed one week following the final vaccination. It was determined, by IFNγ ELISpot, that the consensus mouse MAGE-A vaccine is immunogenic in CD-1 mice against peptides matched to the consensus vaccine sequence, and is capable of breaking tolerance to multiple MAGE-A isoforms simultaneously in the majority of the mice (FIG. 4A,B). Despite the genetic diversity of these mice, the majority of animals generated immune responses against all 6 individual MAGE-A isoforms (FIG. 4B).

Anti-Tumor Activity of MAGE-A Vaccine in Autochthonous Melanoma Tumor Model

Figures 5A, 5B, 5C:
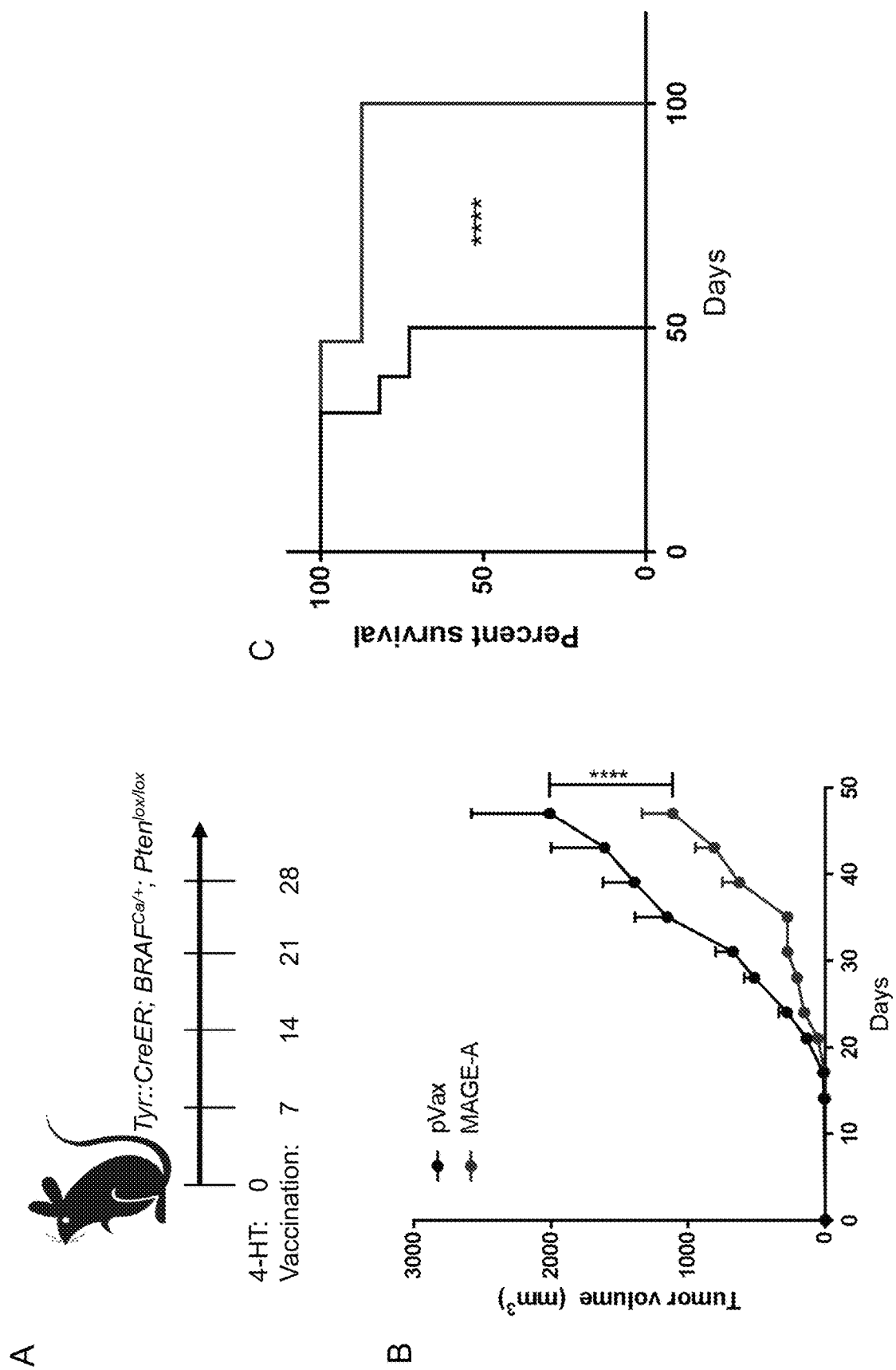
FIG. 5A and FIG. 5F, depicts experimental results demonstrating the anti-tumor activity of MAGE-A vaccine in autochthonous melanoma model.
FIG. 5B depicts the tumor volume measurements over time for pVax control mice or MAGE-A immunized mice.
FIG. 5C depicts the mouse survival over time for pVax control mice or MAGE-A immunized mice. Mice were euthanized according to the standard body condition score.
Figures 5D, 5E, 5F:
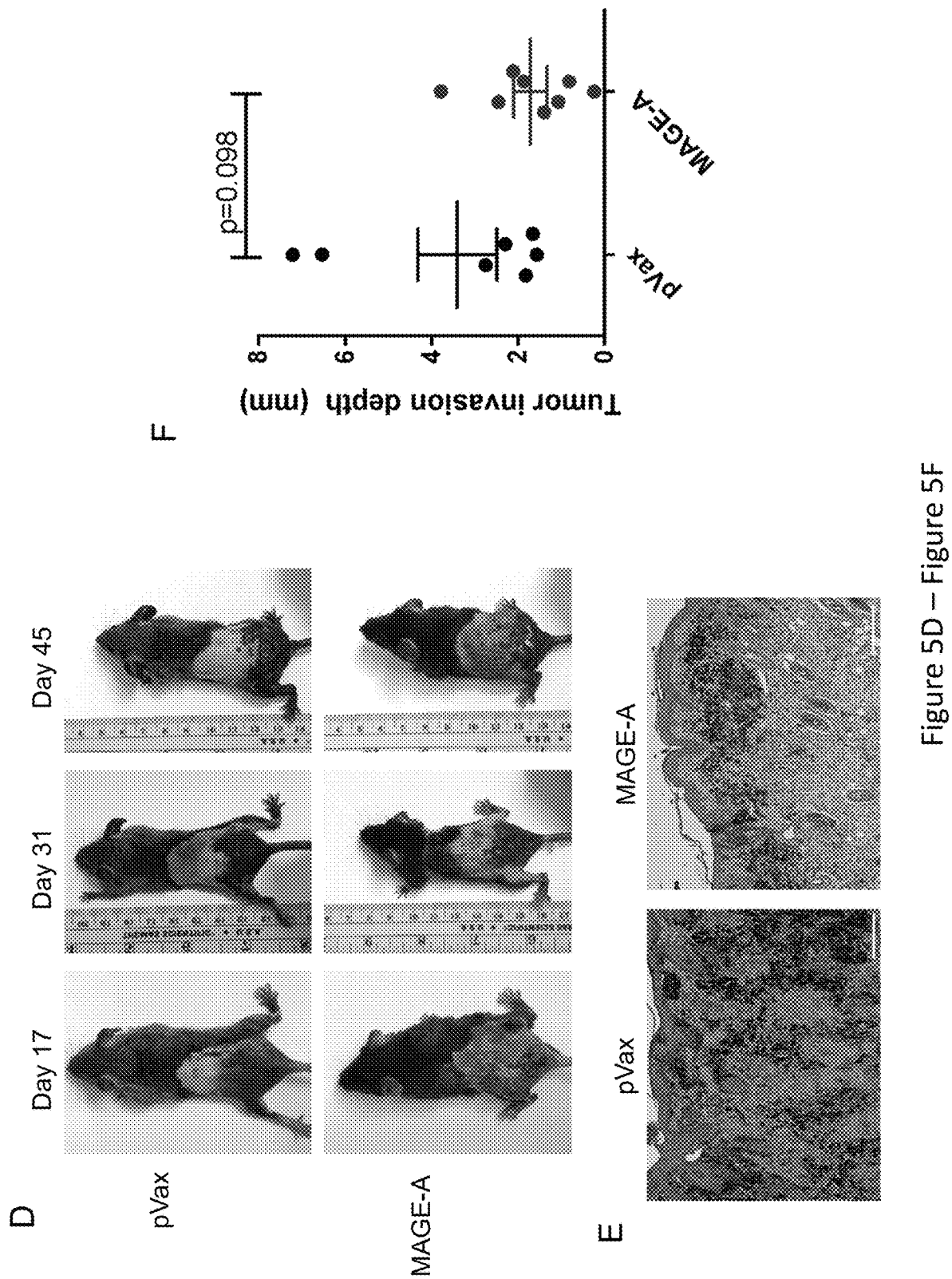
FIG. 5D depicts representative images of mice immunized with either pVax control plasmid or MAGE-A plasmid at day 17, 31 or 45 after tamoxifen induction.
FIG. 5E depicts representative H&E images of tumors harvested from pVax control and MAGE-A immunized mice that were sacrificed on day 50.
Figures 6A, 6B, 6C, 6D:
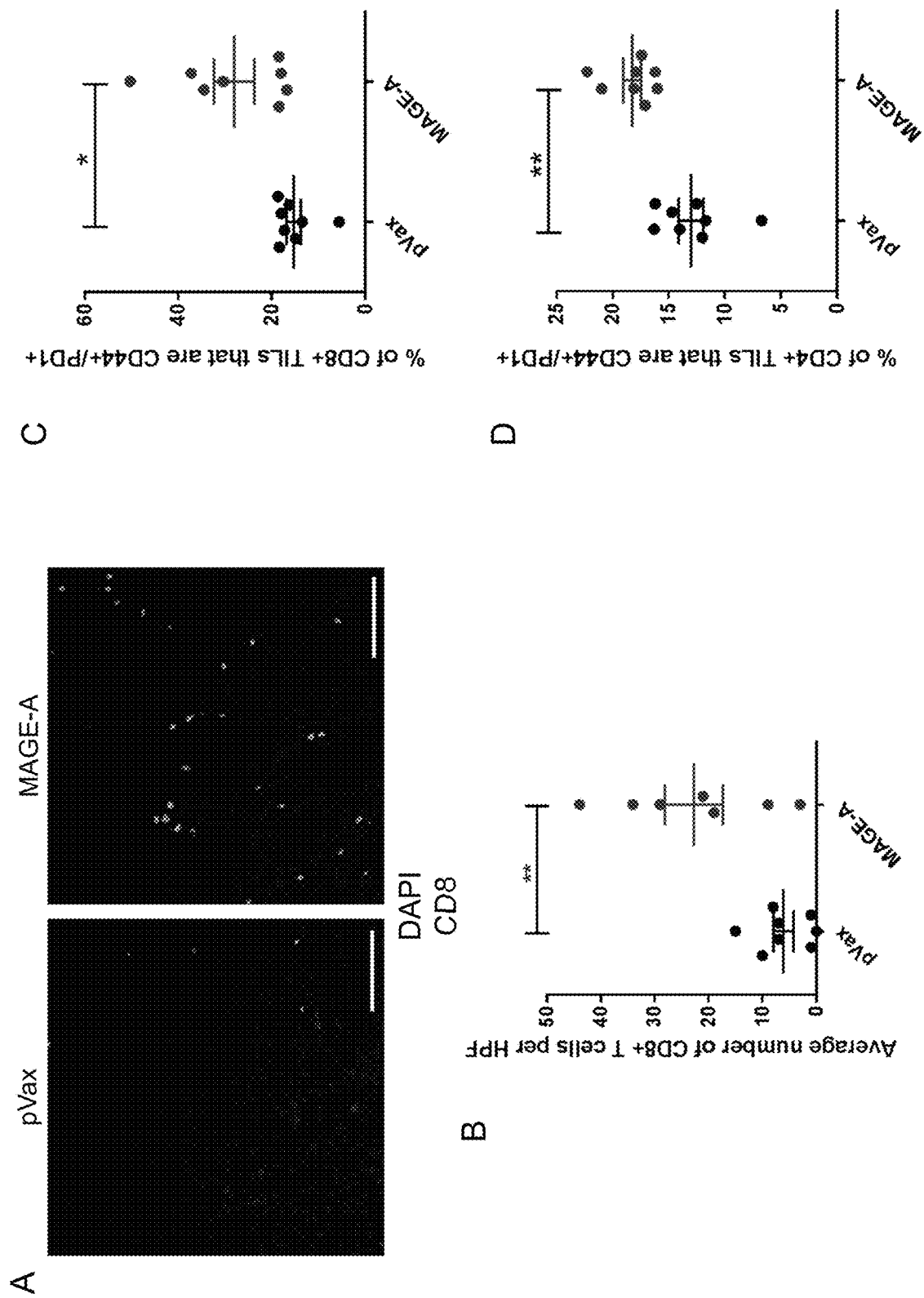
FIG. 6A and FIG. 6D, depicts experimental results demonstrating MAGE-A vaccine induces immune cell infiltration and activation in autochthonous melanoma tumors. 8 pVax immunized and 8 MAGE-A immunized mice were treated according to the schedule in FIG. 5, and were sacrificed on day 50 to assess immune cell infiltration.
FIG. 6B depicts quantification of images in (A), in terms of CD8+ T cells per image. Image quantification was performed for 3 representative images per mouse.
FIG. 6C depicts surface staining of tumor infiltrating CD8+ T cells for CD44 and PD1 expression.
Figure 11:
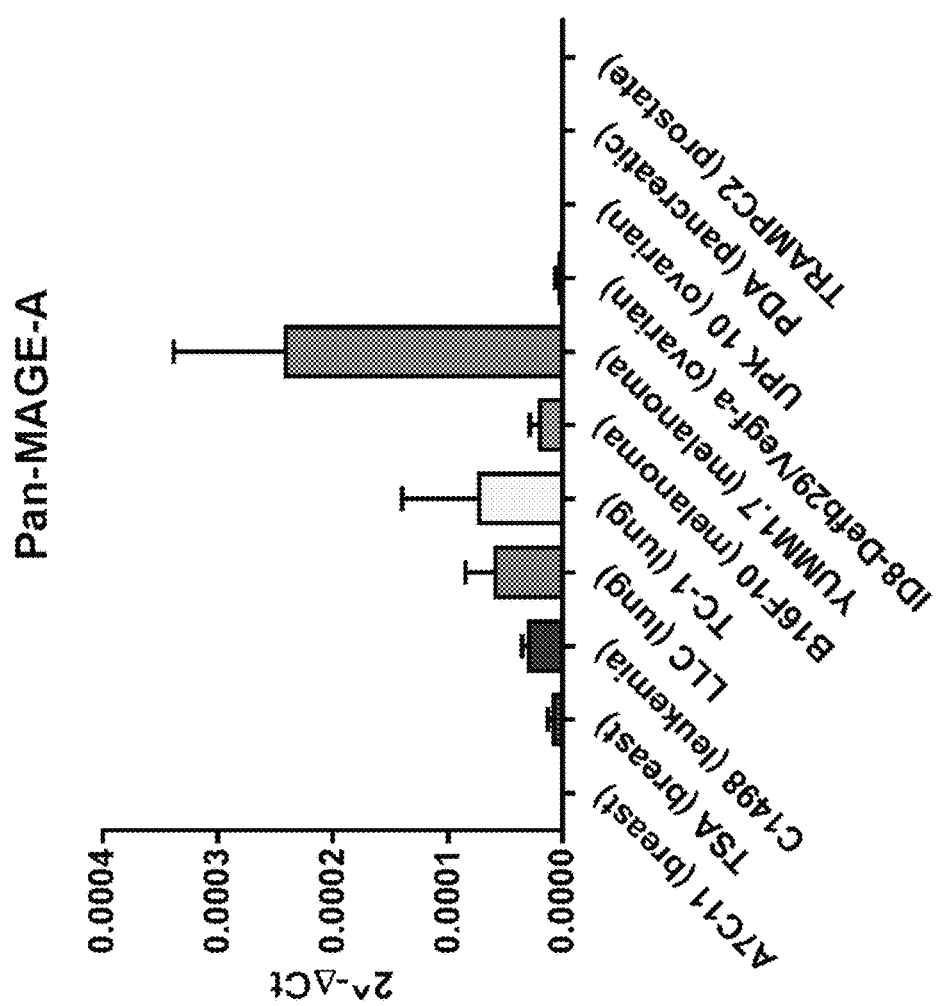
FIG. 11 depicts experimental results demonstrating the expression of MAGE-A in a panel of mouse tumor cell lines.
Figure 12:
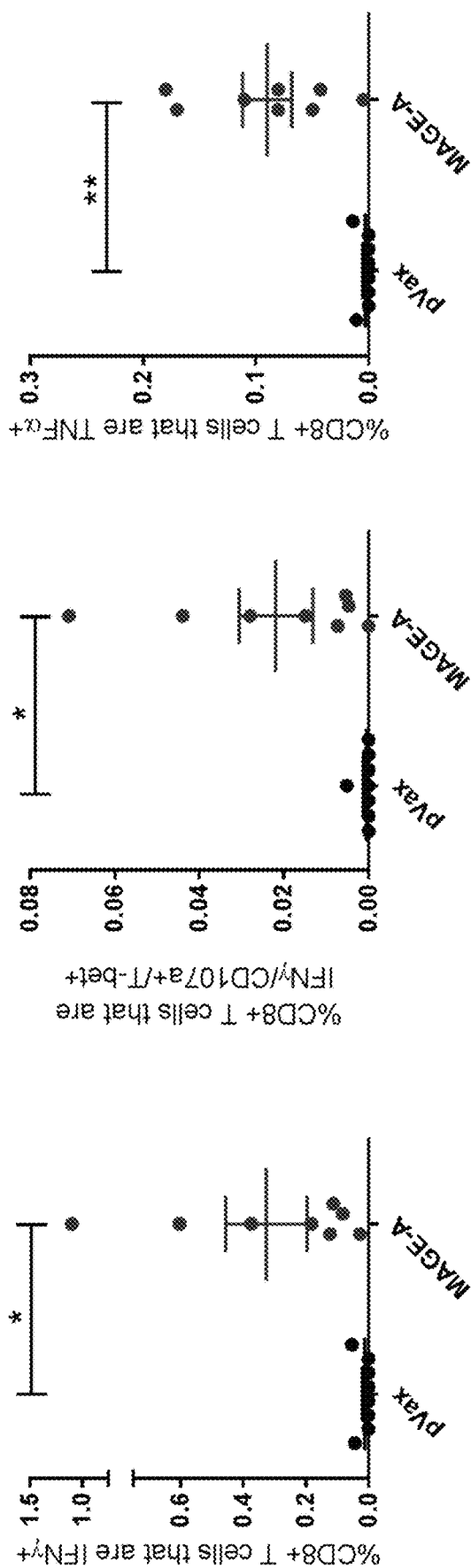
FIG. 12 depicts experimental results demonstrating the immune responses in spleen of autochthonous tumor bearing mice.

To identify an appropriate model for a tumor challenge, MAGE expression was evaluated in a panel of mouse cell lines syngeneic to either C57Bl/6 or Balb/c strains of mice. Pan-MAGE-A qPCR primers that recognize MAGE-A isoforms A1, A2, A3, A5, A6 and A8 simultaneously were used. This analysis showed high expression of MAGE-A isoforms in the B16F10 and YUMM1.7 melanoma cell lines and the LLC and TC-1 lung cancer cell lines (FIG. 11). The highest expression was observed in the YUMM1.7 cell line, which is derived from a transgenic melanoma model expressing BrafV600E, and has both Pten and Cdkn2 knockout (Meeth et al., 2016, Pigment Cell Melanoma Res 29:590-7). Therefore, the MAGE-A was tested in a similar autochthonous tumor model in which Braf V600E expression and PTEN loss are driven by Cre activation in melanocytes of the skin by tamoxifen induction (Tyr::CreER; Braf$^{CA/+}$; Pten$^{lox/lox}$ mice) (Dankort et al., 2009, Nat Genet 41:544-52). Upon induction with topical 4-OHT (tamoxifen), these mice develop melanoma with 100% penetrance. One week after 4-OHT induction, immunization began with either a modified pVax control plasmid or the consensus mouse MAGE-A plasmid (FIG. 5A). The mouse consensus MAGE-A vaccine was effective at significantly slowing tumor growth in this model, and prolonged mouse survival by a median of 50 days compared to the modified pVax control group (2-fold prolongation in survival, FIG. 5B-D). Half of the mice in the study were sacrificed at day 50 to evaluate appearance and immune infiltration in melanoma tumors, as well as examine the immune response in the spleen. MAGE-A vaccine was able to decrease melanoma invasion depth in the skin (FIG. 5E,F), as well as drive CD8+ T cells to the tumor (FIG. 6A,B). Furthermore, the CD4+ and CD8+ T cells in tumor tissues exhibited higher expression of CD44 and PD-1, markers of immune activation (FIG. 6C,D). Tumor-bearing mice immunized with the MAGE-A vaccine also exhibited robust antigen-specific CD8+ T cell responses in the spleen, which persisted at least 22 days after the final immunization (FIG. 12). These results strongly support the potency of this MAGE-A vaccine in this melanoma therapy model.

Figures 7A, 7B, 7C:
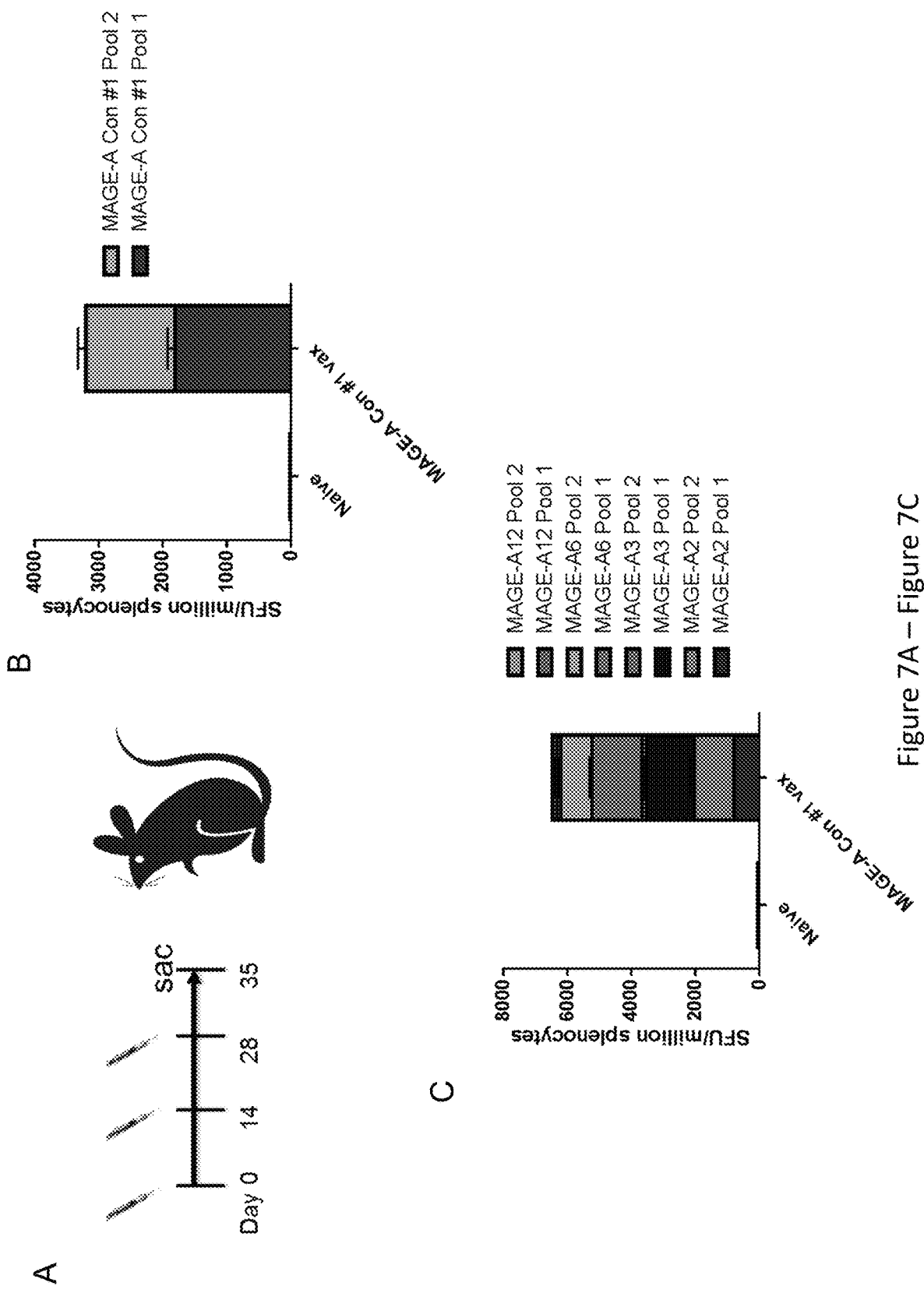
FIG. 7A through FIG. 7E, depicts experimental results demonstrating immunogenicity and cross-reactivity of human MAGE-A consensus vaccines in mice.
Figures 7D, 7E:
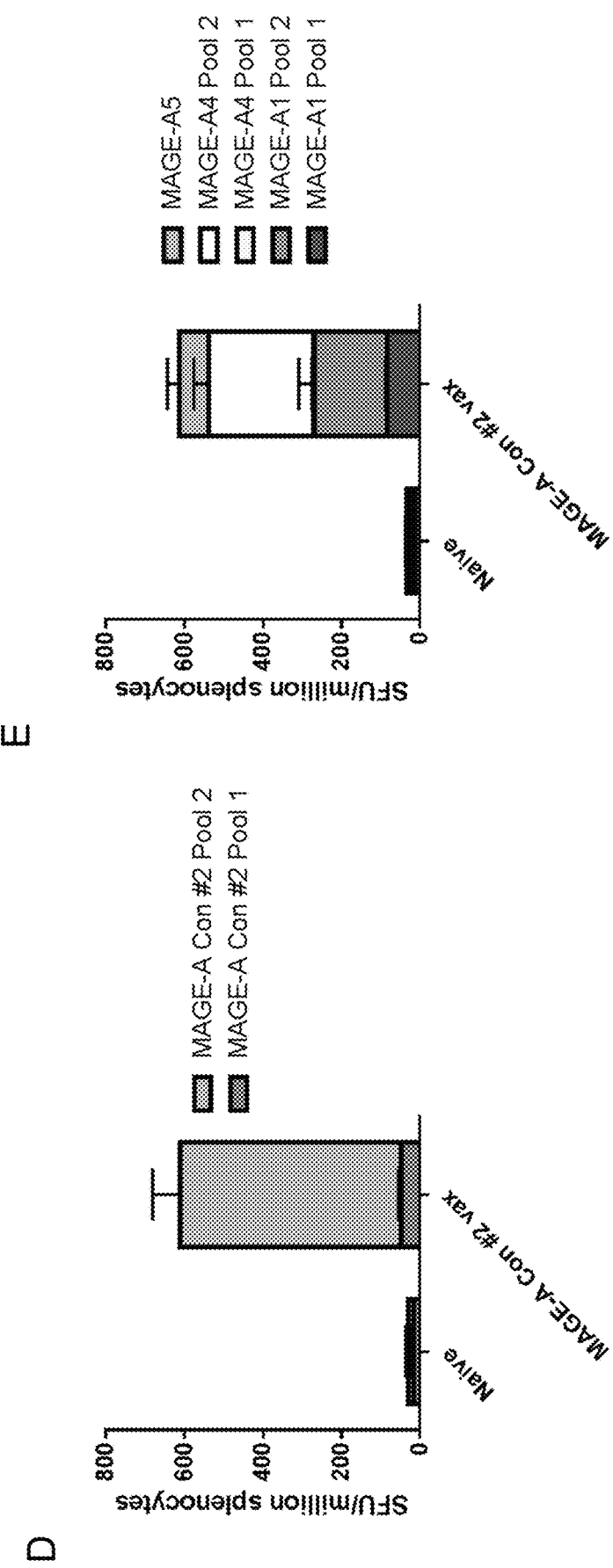

Immunogenicity and Cross-Reactivity of Human MAGE-A Consensus DNA Vaccines in Mice Next, the ability of the human versions of the MAGE-A DNA vaccines to generate cross-reactive immune responses in C57Bl/6 mice was tested (FIG. 7A). C57Bl/6 mice were immunized with 25 μg of the Human MAGE-A Consensus #1 vaccine or the Human MAGE-A Consensus #2 vaccine three times at two-week intervals, and cellular immune responses were assessed one week following the final immunization (FIG. 7A). It was observed that both vaccines are immunogenic and generate robust IFNγ ELISpot responses to the vaccine-matched, consensus MAGE-A peptides (FIG. 7B, D). Further, both vaccines generate cross-reactive responses towards all predicted human MAGE-A isoforms by IFNγ ELISpot (FIG. 7C,E). The MAGE-A Consensus #1 vaccine generates cross-reactive immune responses against MAGE-A2, MAGE-A3, MAGE-A6 and MAGE-A12. The MAGE-A Consensus #2 vaccine generates cross-reactive immune responses against MAGE-A1, MAGE-A4 and MAGE-A5.

Discussion

Previous clinical efforts to target the MAGE-A family member with immunization have focused on MAGE-A3 specifically, based on limited gene expression data showing high expression for this particular isoform in various solid tumors (Vantomme et al., 2004, J Immunother 27:124-35). Here, data is reported from TCGA showing that each member of the MAGE-A family, not just MAGE-A3, is highly expressed in human tumors (approximately 10-30% of all human tumors for each isoform). In fact, based on TCGA data, 84% of melanoma patients express 1 or more isoforms that are targeted by the two Human MAGE-A consensus vaccines developed herein, indicating important clinical applicability for melanoma patients. Furthermore, multiple MAGE-A family members are expressed within the same tumor, particularly so in melanoma patients. These data provide further support for the development of a cross-reactive vaccine that can target multiple MAGE-A family members simultaneously. The entire MAGE-A family is clustered on the X-chromosome; however, each family member is under independent transcriptional control (Barker and Salehi, 2002, J Neurosci 67:705-12). The reason for this independent regulation is not clear, nor is the understanding of the individual regulation; however, this family of antigens is thought to be silenced by promoter methylation in normal human tissues (De Smet et al., 1999, Mol Cell Biol 19:7327-35; Wischnewski et al., 2006, Mol Cancer Res 4:339-49; Weber et al., 1994, Cancer Res. 54:1766-71). This methylation is removed in tumor cells due to epigenetic re-programming. While certain MAGE-A isoforms are suggested to have roles in cancer-promoting signaling pathways, it is not clear whether these isoforms are necessary for tumor progression (Pineda et al., 2015, Cell 160:715-28; Doyle et al., 2010, Mol Cell 39:963-74; Yang et al, 2007, Cancer Res. 67:9954-62; Liu et al., 2008, Cancer Res 68:8104-12). This suggests that tumors could escape immune pressure from a MAGE-targeted vaccine through down-regulation of a particular MAGE isoform. However, this immune evasion becomes less probable when multiple MAGE-A family members are targeted simultaneously. Thus, a cross-reactive MAGE-A vaccine has a significant advantage over vaccines that target individual MAGE-A isoforms in preventing tumor immune escape.

The MAGE-A family of proteins may be unique in its ability to generate spontaneous T cell responses in patients, indicating a potential lack of tolerance or more limited tolerance to this family of antigens. While naturally occurring responses to MAGE-A family members do exist, they are still relatively rare, making the role of tolerance to this antigen unclear (Stockert et al., 1998, J Exp Med 187:1349-54; Dhodapkar et al., 2000, Clin Cancer Res 6:4831-8). In a small cohort of patients (5 patients), it was shown that there is expression of MAGE-A isoforms in medullary thymic epithelial cells, but that expression of each isoform was variable (50). MAGE-A1 isoform expression was only detected in ⅕ patients, while MAGE-A3 and MAGE-A4 expression was detected in ⅘ patients (Gotter et al., 2004, J Exp Med 199:155-66). These data indicate that targeting multiple MAGE-A isoforms may be advantageous for eliciting an immune response against select isoforms that may not be subject to central tolerance. More study needs to be performed in this regard in humans to better understand factors that affect tolerance to this family of antigens. One advantage of this design is that, by including diversity into the design of these antigens, these hot spots of dissimilarity are quite similar to neoepitopes. They would be expected to drive cross-reactive class II responses to these hotspots, generating improved ability to break tolerance. Indeed, using the mouse MAGE-A immunogen it is demonstrated herein that the consensus vaccine design strategy is effective at breaking tolerance to many mouse MAGE-A isoforms.

There are some toxicity concerns regarding MAGE-A3 targeted TCR gene therapy. Two cellular CD8-based MAGE-A3 TCR therapies have been tested in the clinic. Unfortunately, in both clinical trials patients experienced unexpected toxicity which precluded further clinical development of these therapies. An affinity-enhanced HLA-A*01 specific MAGE-A3 TCR therapy showed unexpected cardiovascular toxicity in the first 2 patients treated due to cross-reactivity of the TCR with peptide from the muscle-specific titin protein (Cameron et al., 2013, Sci Transl Med 5:197ra103; Linette et al., 2013, Blood 122:863-71). A separate study used a high-avidity HLA-A*0201 specific MAGE-A3 TCR, which showed unexpected neurological toxicity in 3/9 patients, resulting in 2 unexpected deaths (Graff-Dubois et al, 2002, J Immunol 169:575-80; Morgan et al., 2013, J Immunother 36:133-51). This was likely due to cross-reactivity of the TCR with low levels of MAGE-A9/12 expression in neuronal cells in the brain of these patients. The toxicity correlated with the number of engineered T cells that were adoptively transferred, suggesting that lower levels of T cells or a lower affinity TCR may avoid this type of toxicity (Graff-Dubois et al, 2002, J Immunol 169:575-80; Morgan et al., 2013, J Immunother 36:133-51). Patients in this study received between 28-79 billion MAGE-specific T cells, in addition to one or more doses of IL-2 (Morgan et al., 2013, J Immunother 36:133-51). Despite the fact that there was unprecedented toxicity, 5/9 patients did show clinical regression of their lesions after treatment, suggesting that CD8+ T cell therapy can be effective in generating an anti-tumor response against this antigen that can have clinical impact (Graff-Dubois et al, 2002, J Immunol 169:575-80; Morgan et al., 2013, J Immunother 36:133-51).

Despite this toxicity shown with the MAGE-A3 TCR therapy, MAGE-A4 TCR therapy was successfully performed in patients with esophageal cancer without significant toxicity (Kageyama et al., 2015 Clin Cancer Res. 21). Furthermore, MAGE-A3 targeted vaccine immunotherapy was safe in patients, despite induction of MAGE-A3 specific CD4+ T cells and antibodies (Vansteenkiste et al., 2013, J Clin Oncol 31:2396-403; Kruit et al., 2013, J Clin Oncol 31:2413-20). One advantage of the DNA vaccine platform is that mice may be immunized with the cross-reactive mouse MAGE-A immunogen long-term, which is not possible with TCR based gene therapy. No apparent off-tumor toxicity was observed in these mice. Further studies in larger organisms, such as non-human primates, can further address this important issue. The DNA vaccine targeting MAGE-A antigens described here elicits anti-tumor immunity while generating fewer MAGE-specific CD8+ T cells compared to TCR based gene therapy, decreasing the likelihood of off-tumor toxicity. In addition, because DNA vaccines induce natural antigen-specific immunity (not ex vivo affinity-enhanced), there is likely in vivo regulation of the immune response to prevent this type of autoimmune attack.

Cell Culture and Transfection 293T cells were obtained from ATCC for transfections, and maintained in Dulbecco's Modified Eagle Medium (DMEM) supplemented with 10% fetal bovine serum (FBS).

This cell line was routinely tested for Mycoplasma contamination, and was maintained at low passage (<20 passages) in cell culture. 293T cells were transfected with the indicated constructs using the GeneJammer transfection reagent according to the manufacturer's guidelines. Cells were harvested using RIPA lysis buffer supplemented with EDTA-free protease inhibitor for analysis by western blot, or were harvested using the RNeasy Plus Mini Kit for RNA extraction.

DNA Plasmids

The synthetic mouse consensus MAGE-A sequence was generated by aligning mouse MAGE-A1, mouse MAGE-A2, mouse MAGE-A3, mouse MAGE-A5, mouse MAGE-A6 and mouse MAGE-A8 amino acid sequences using ClustalX2. The synthetic human MAGE-A consensus #1 sequence was generated by aligning human MAGE-A2, human MAGE-A3, human MAGE-A6 and human MAGE-A12 amino acid sequences using ClustalX2. The synthetic human MAGE-A consensus #2 sequence was generated by aligning human MAGE-A1, human MAGE-A4, and human MAGE-A5 amino acid sequences using Clustal X2. All sequences were RNA and codon optimized, with a Kozak sequence and an IgE leader sequence added at the N terminus. All plasmids were cloned into the modified pVax1 vector by GenScript. The percentage homology between sequences was calculated using Mega6. Comparative models of the defined MAGE-A consensus sequences were built using the MODELLER algorithm (Sali and Blundell, 1993, J Mol Biol 234:779-815; Webb and Sali, 2016, Curr Protoc Protein Sci 86:2.9.1-2.9.37), implemented in Discovery Studio. Sequences were analyzed using the PONDR algorithm to predict potential intrinsically disordered regions prior to model building (Dunker et al., 2001, J Mol Graph Model 19:26-59).

Western Blot 4-12% Bis-Tris NuPAGE gels and PVDF membranes were used for western blot analysis. Odyssey blocking buffer reagents were used for blocking, primary and secondary antibody incubations. The following primary antibodies were used: Anti-Actin AC-15 (Sigma, 1:1000), anti-MAGE-A (6C1, Santa Cruz, 1:200), and anti-FLAG (M2, Sigma, 1:500). The following secondary antibodies were used: IRDye 680RD goat anti-mouse and IRDye 800CW goat anti-rabbit (LiCor). The membrane was imaged using the LiCor Odyssey CLx.

RNA Extraction and qPCR

RNA extraction was performed using a QIAGEN RNeasy Plus Mini Kit. RNA was converted to cDNA using the Applied Biosystems High Capacity RNA to cDNA kit. qPCR was performed using Power SYBR Green on an ABI 7900 Fast RT PCR machine. Expression levels are expressed in terms of $2^{-\Delta Ct}$ ($\Delta Ct$ is compared to the GAPDH control). The following qPCR primers were used for these studies:

```
Pan-mouse MAGE:
                                      (SEQ ID NO: 18)
CCACCTCAAATAAAGTGTATGGCA(F), (SEQ ID NO: 19)
ACCAGAAAGTCCACCAAGTCA(R), Mouse MAGE-A consensus:
                                      (SEQ ID NO: 20)
GCCACCATGGATTGGACTTG(F), (SEQ ID NO: 21)
TGGCCATTGTCTCCTGATCG(R), Human MAGE-A consensus #1:
                                      (SEQ ID NO: 22)
GTTTGCACACCCCAGAAAGC(F), (SEQ ID NO: 23)
GGGTGGGTAGCTGATGTGAG(R), Human MAGE-A consensus #2:
                                      (SEQ ID NO: 24)
TGGCAGATCTGGTGCACTTT(F), (SEQ ID NO: 25)
TTCACGTCGATGCCGAAGAT(R),
and GAPDH:
                                      (SEQ ID NO: 26)
CCTGCACCACCAACTGCTTA(F), (SEQ ID NO: 27)
AGTGATGGCATGGACTGTGGT(R).
```

Mice and Immunization

C57Bl/6 and CD-1 outbred mice were acquired from Jackson Laboratories and housed at the Wistar Institute. The Tyr::CreER;Braf$^{Ca/+}$; Pten$^{lox/lox}$ transgenic mice were generated as previously described (Dankort et al., 2009, Nat Genet 41:544-52). Genotyping of the mice was performed as previously described (Liu et al., 2011, Cancer Biol Ther 12:1005-14). For tumor induction, 6-8 week old mice were treated topically with a 5 mM 4-hydroxytamoxifen (4-HT) solution on the flank to initiate tumor formation (Dankort et al., 2009, Nat Genet 41:544-52). For tumor measurements, the following formula was used: volume=a*b*c/2, where a=maximum of length, b=maximum of width and c=thickness (Sreenivasan et al., 2016, J Cancer Res Ther 12:161). Mice were euthanized when they achieved the standard body condition score (multiple tumor spots with maximum length of 30 mm). For immunization, mice were injected with 30 µL of DNA (25 µg per mouse) into the tibialis anterior (TA) muscle, followed by electroporation using the CELLECTRA®-3P device. Mice were delivered two 0.1 Amp electric constant current square-wave pulses for each immunization. The vaccine schedule is indicated in each figure legend.

Splenocyte and Tumor Infiltrating Lymphocyte (TIL) Isolation

After mice were euthanized, spleens and tumor tissues (if applicable) were collected in Roswell Park Memorial Institute (RPMI) medium supplemented with 10% FBS. Spleens were processed using a stomacher, red blood cells were lysed using ACK lysis buffer, and the remaining cells were filtered through a 40 µm filter. Tumors were minced using a scalpel, and incubated in a tumor dissociation enzyme mix consisting of: 170 mg/L Collagenase I, II and IV, 12.5 mg/L DNAse I, 25 mg/L Elastase in 50% RPMI+10% FBS and 50% Hyclone L-15 Leibowitz medium. Tumors were incubated in this mixture with end-over-end mixing for 1 hour at 37° C., and then filtered twice through a 40 µm filter prior to plating for staining.

ELISpot Assay

MABTECH Mouse IFNγ ELISpot$^{PLUS}$ plates were used for ELISpot analysis. 200,000 splenocytes were plated per well and stimulated for 18-24 hours with 5 µg/mL of peptides (15 mer peptides overlapping by 9 amino acids) in RPMI+10% FBS. Spots were developed according to the manufacturer's instructions, and quantified using an ImmunoSpot CTL reader. Spot forming units (SFU) were calculated by subtracting media alone wells from the peptide stimulated wells. Concanavalin A stimulation was used as a positive control to ensure proper spot development.

Intracellular Cytokine Staining and Flow Cytometry

Splenocytes were stimulated in the presence of 5 μg/mL peptide, Protein Transport Inhibitor Cocktail and FITC α-mouse CD107a (clone 1D4B, Biolegend) for 5-6 hours. Cell stimulation cocktail was used as a positive control for stimulation instead of peptide. TILs were stained directly without stimulation. After stimulation, cells were washed and incubated with LIVE/DEAD violet. Cells were then incubated with surface stain (in 1% FBS in PBS) for 30 minutes at room temperature, followed by fixation and permeabilization for 15 minutes at 4° C. After permeabilization, cells were washed and incubated in intracellular stain (in fixation/permeabilization wash buffer) for 1 hour at 4° C. The following antibodies were used for analysis: PECy5 αCD3 (clone 145-2C11, BD Pharmingen), BV510 αCD4 (clone RM4-5, Biolegend), BV605 αTNFα(clone MP6-XT22), PE αT-bet (clone 4B10, Biolegend), APCCy7 αCD8 (clone 53-6.7, Biolegend), AF700 αCD44 (clone IM7, Biolegend), APC αIFNγ (clone XMG1.2, Biolegend), FITC αCD45 (30-F11, Biolegend), BV711 αPD-1 (clone 29F.1A12, Biolegend). All data was collected on an LSR18 flow cytometer (BD Biosciences) and analyzed using FlowJo software. For analysis, media alone control wells were subtracted from peptide containing wells for antigen-specific immune responses.

Immunofluorescence/Immunohistochemistry Staining

Hematoxylin and Eosin staining was performed according to standard protocols from tissue that was fixed in 10% neutral-buffered formalin and paraffin-embedded. For immunofluorescence staining, tissues were collected in O.C.T. on dry ice and stored at −80° C. For CD8 T cell staining, frozen tissue was fixed on slides with 4% paraformaldehyde (in PBS) for 15 minutes at room temperature, and then permeabilized with 0.5% Triton X-100 for 15 minutes at room temperature. The tissue was blocked for 1 hour at room temperature with 2.5% BSA and 5% horse serum in PBS. The Avidin/Biotin Blocking Kit was also used to reduce background staining. Primary antibody (CD8α-biotin, 53-6.7, 1:2000) in 1% horse serum in PBS was incubated overnight at 4° C. in a humidified chamber. The next day, the TSA-Biotin kit was used for signal amplification, and slides were incubated in secondary antibody (Streptavidin AF488, 1:500) for 30 minutes at room temperature. Slides were mounted with Prolong Gold Antifade with DAPI. H&E stained slides were imaged with a Nikon 80i upright microscope, and immunofluorescence slides were imaged using a Zeiss LSM Confocal microscope. Image analysis was performed using Photoshop or Fiji/ImageJ software.

The Cancer Genome Atlas data analysis

RNA-seq data (RSEM values) from The Cancer Genome Atlas (TCGA) was downloaded through the GDAC data portal (gdac.broadinstitute.org/). All samples marked as matched normal were filtered and included in the normal tissue control group (n=754). The following human tumor types were analyzed: ACC (n=79), BLCA (n=408), BRCA (n=1100), CESC (n=306), COADREAD (n=382), DLBC (n=48), ESCA (n=185), GBM (n=166), GBMLGG (n=696), HNSC (n=522), KIPAN (n=891), LAML (n=173), LGG (n=530), LIHC (n=372), LUAD (n=518), LUSC (n=501), MESO (n=87), OV (n=307), PAAD (n=179), PCPG (n=184), PRAD (n=498), READ (n=72), SARC (n=263), SKCM (n=472), STAD (n=415), STES (n=600), TGCT (n=156), THCA (n=509), THYM (n=120), UCEC (n=370), UCS (n=57), and UVM (n=80). The threshold for expression was set to be greater than 2 standard deviations above the mean for the normal tissue for each MAGE-A isoform.

Statistical Analysis

All statistical analysis was done using GraphPad Prism software. All error bars represent the mean±the standard error of the mean (SEM). Statistical significance was determined by a two-tailed t-test for experiments with only 2 experimental groups, or a one-way ANOVA followed by Tukey's post-hoc HSD test for experiments with more than 2 experimental groups. For tumor growth over time, multiple t-tests were performed for each time point. For mouse survival analysis, significance was determined using a Gehan-Brelow-Wilcoxon test.

Example 2

Development of a Novel Synthetic Micro Consensus DNA Vaccine Targeting the Mage-A Family for Cancer Immune Therapy DNA vaccines consist simply of an expression plasmid encoding a specific gene of interest. The plasmid is injected into the muscle, and the myocytes of the muscle take up the plasmid and begin to express the protein and present it on Class I. In addition, antigen-presenting cells in the muscle can also take up this DNA and present it on class I molecules as well.

Described herein is the DNA vaccine design targeting the MAGE family of proteins, and in particular the MAGE-A sub-family.

Figure 13:
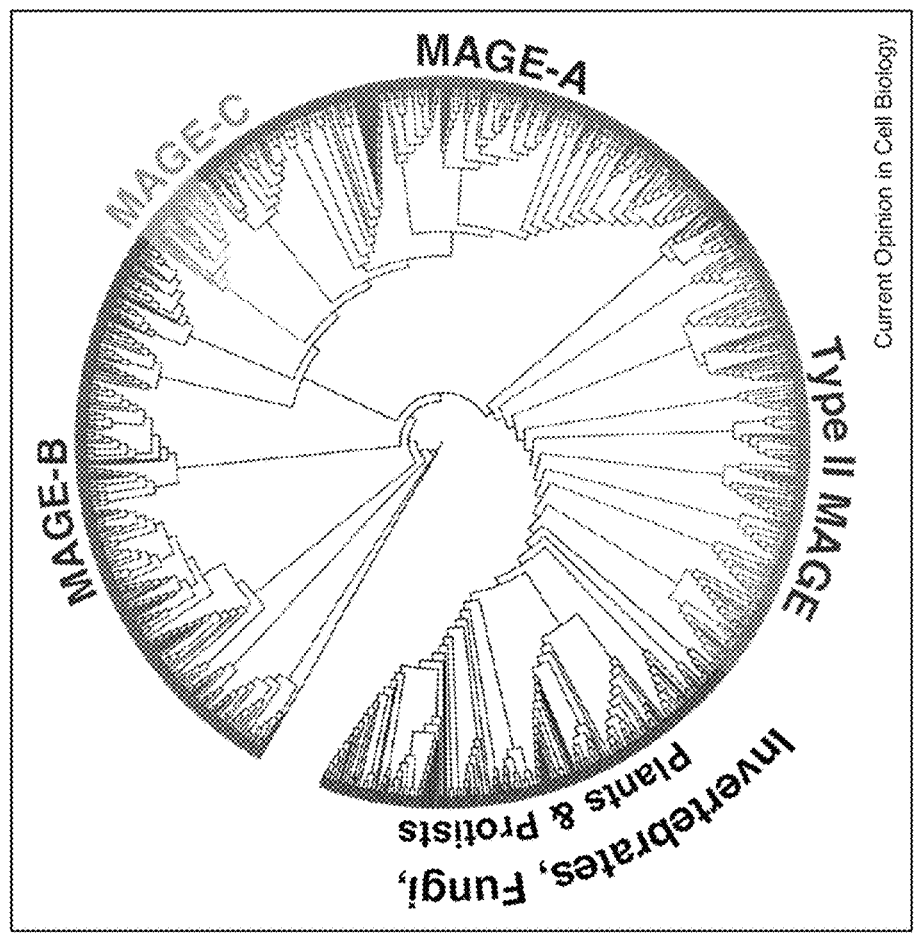
FIG. 13 depicts the MAGE family members in cancer.

MAGE-A1 was the first cancer antigen discovered to be recognized by cytolytic T lymphocytes in a human melanoma patient. In total, there are 10 MAGE-A family members in humans, all of which are expressed at some level in certain human cancers (FIGS. 1 and 13). MAGE-A has low or no expression in normal somatic human tissues, with the exception of the placenta and the germs cells of the testis. Various MAGE-A family members are over-expressed in cancer but have restricted expression in normal tissues. Thus, the goal of this study was to design a synthetic consensus DNA vaccine targeting multiple MAGE-A isoforms.

Figure 14:
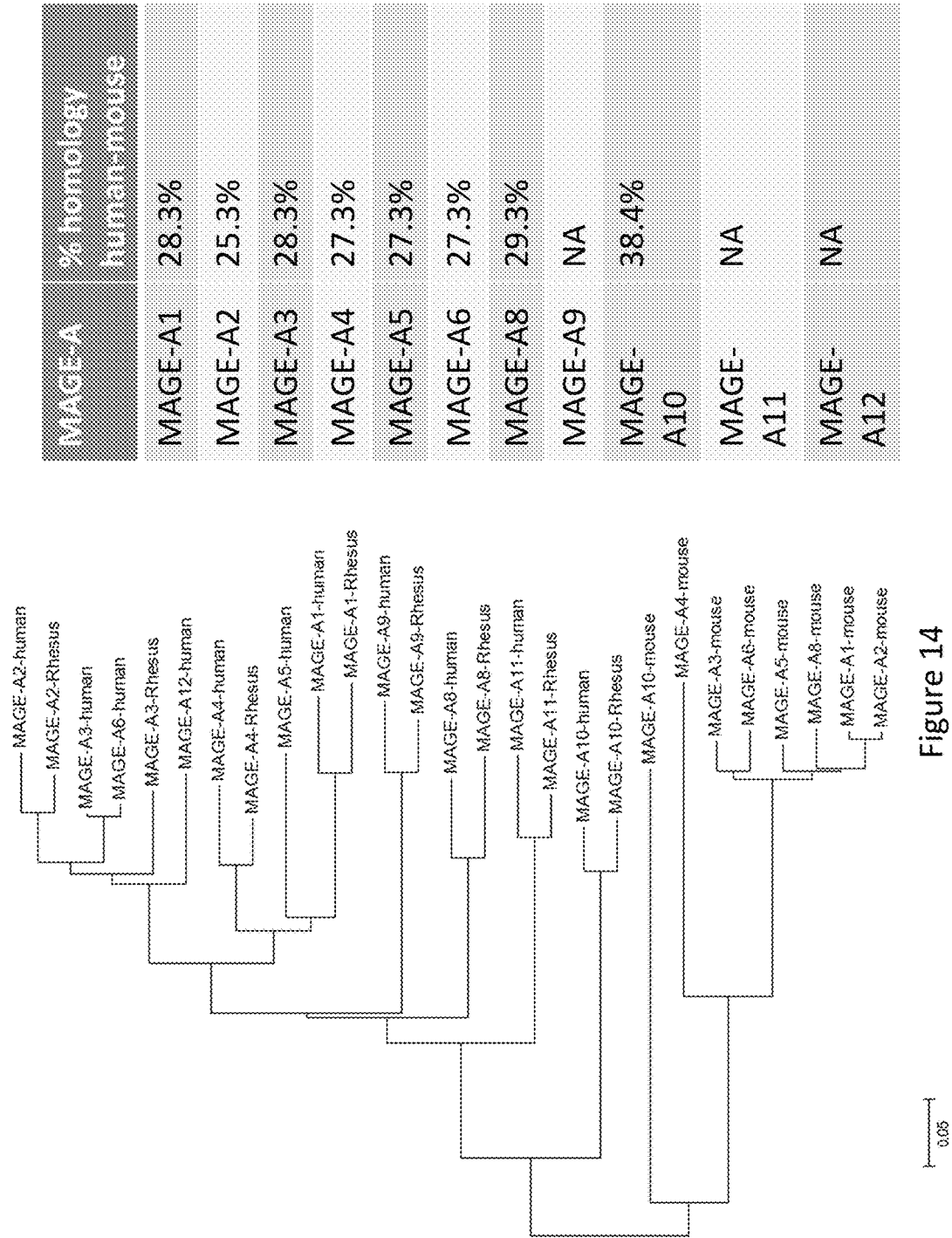
FIG. 14 depicts a phylogenetic tree demonstrating the MAGE-A sequence conservation.
Figure 15:
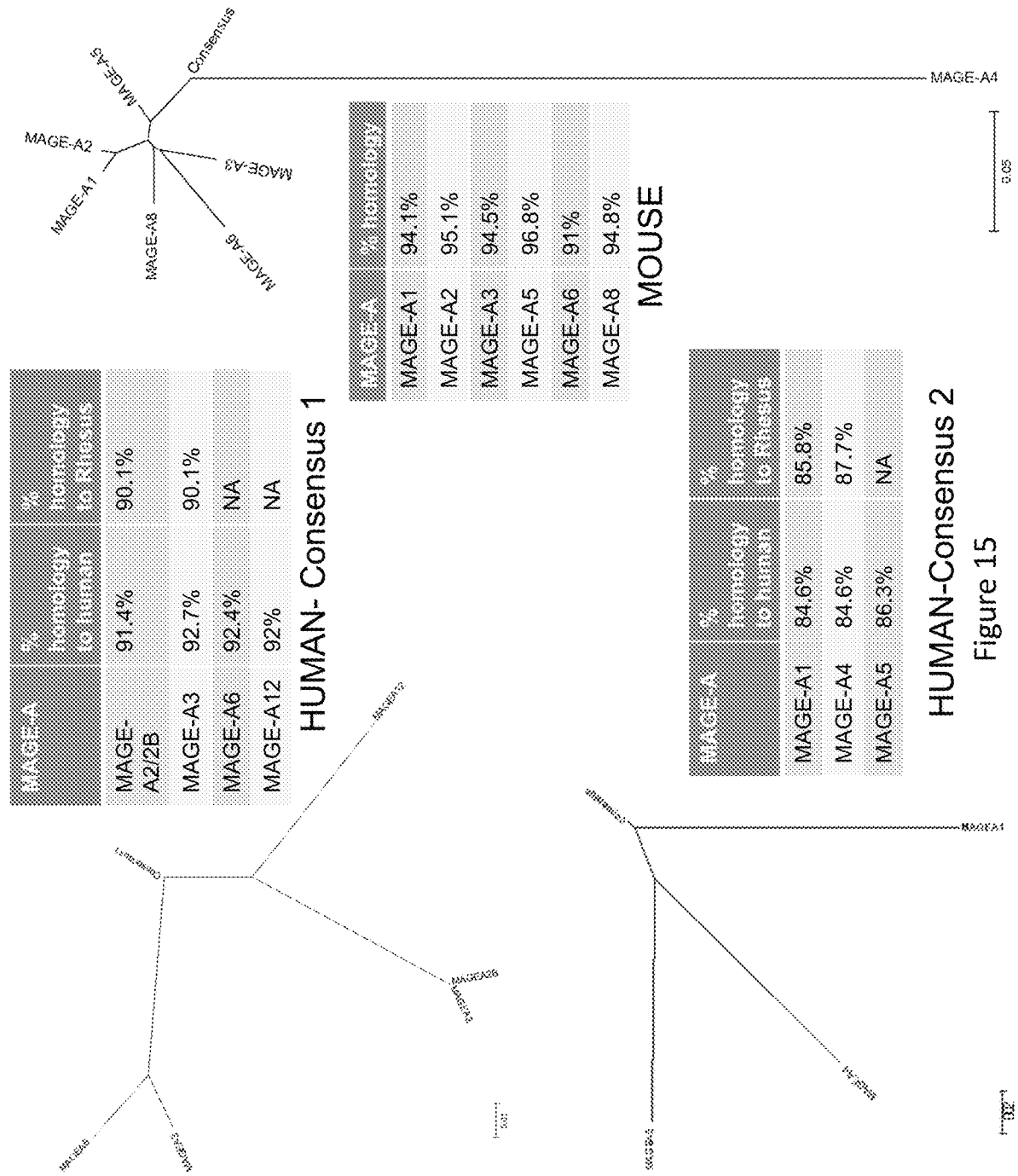
FIG. 15 depicts the homology of the consensus sequences.

MAGE-A family members are highly homologous, but not well conserved (FIGS. 2 and 14). Three consensus sequences were created. Human consensus 1 (hCON1) was derived from human MAGEA2, MAGEA2b, MAGEA3, MAGEA6, and MAGEA12. Human consensus 2 (hCON2) was derived from human MAGEA1, MAGEA4 and MAGEA5. Mouse consensus (Mouse CON) was derived from mouse MAGEA1, MAGEA2, MAGEA3, MAGEA5, MAGEA6, and MAGEA8 (FIGS. 2 and 15).

Figure 16:
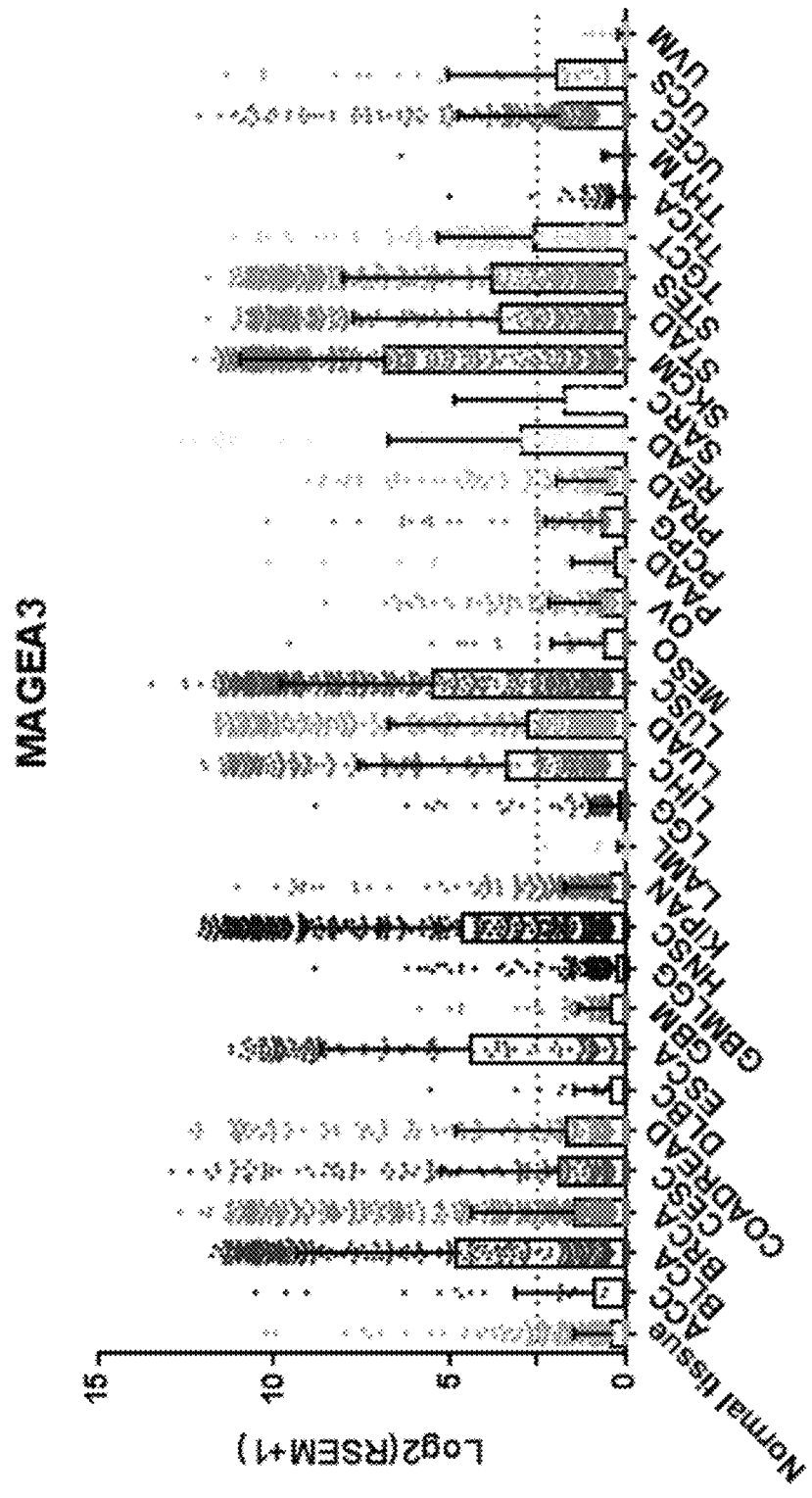
FIG. 16 depicts experimental results demonstrating MAGE-A isoform expression in cancer using TCGA.
Figure 17:
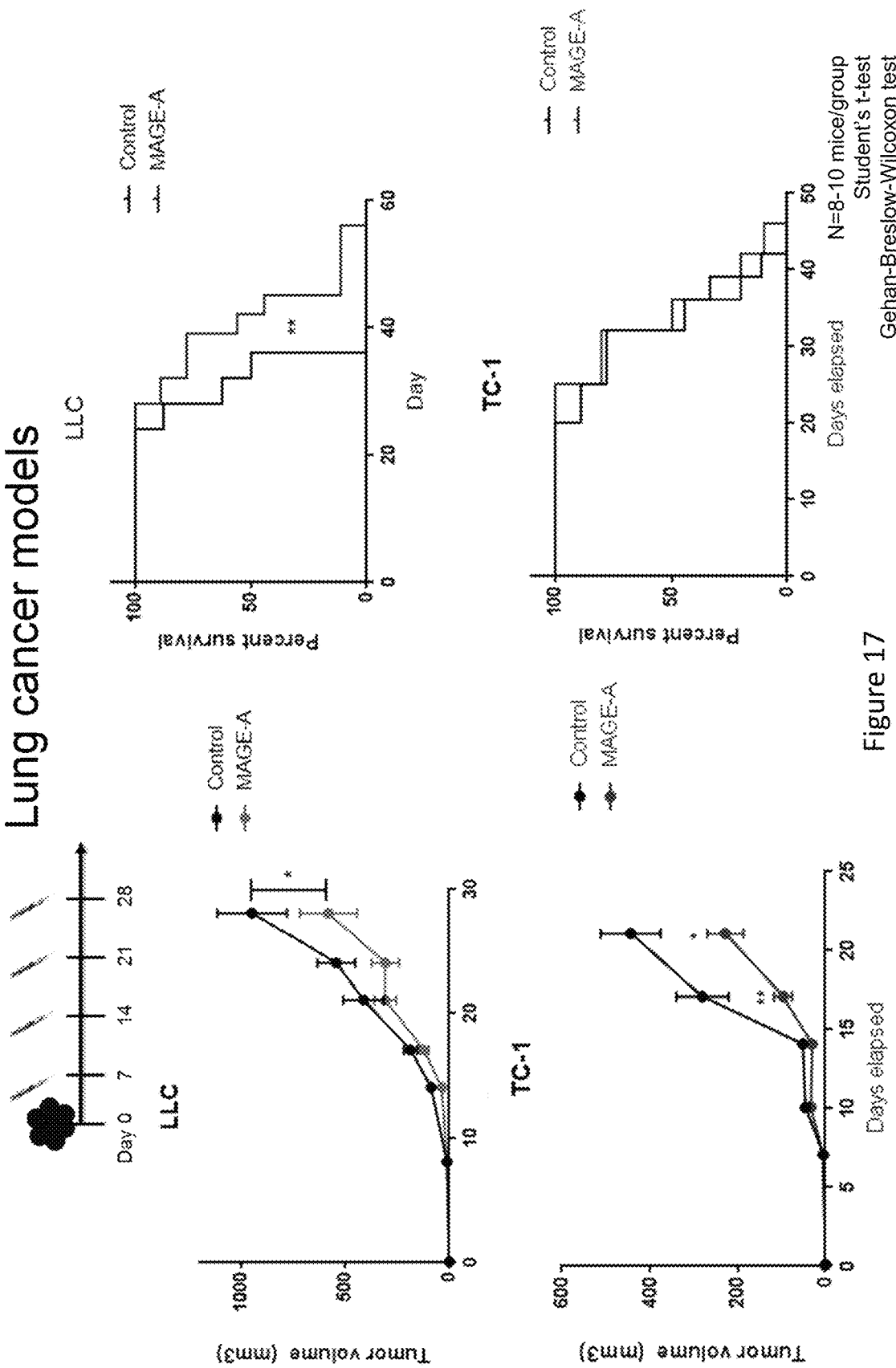
FIG. 17 depicts experimental results demonstrating antitumor activity of mouse MAGE-A vaccine in lung cancer models.
Figure 18:
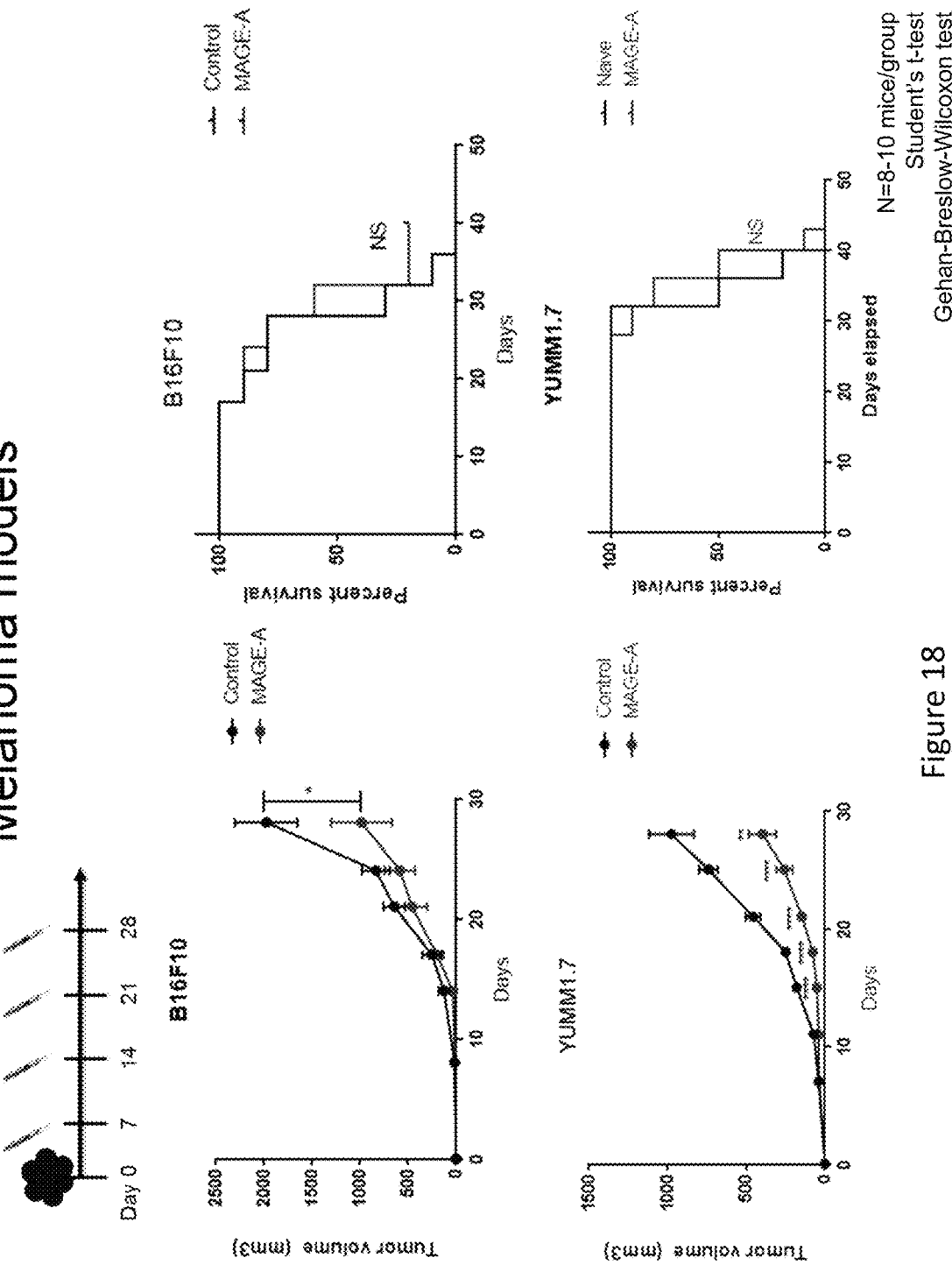
FIG. 18 depicts experimental results demonstrating antitumor activity of mouse MAGE-A vaccine in melanoma cancer models.

Mouse MAGE-A consensus vaccine is immunogenic and breaks tolerance to multiple isoforms (FIGS. 3 and 9). Further, the MAGE-A vaccine is immunogenic in CD-1 outbred mice and is capable of breaking tolerance to multiple MAGE isoforms (FIG. 4). Analysis of MAGE-A isoform expression in mouse cancer lines showed high expression in many cancer cell types (FIGS. 11 and 16). The MAGE-A vaccine showed efficacy in tumor volume reduction in lung cancer models, melanoma models (FIGS. 17-18).

MAGE-A isoforms are expressed in a large percentage of human tumors and multiple isoforms are frequently expressed within the same patient tumor. Consensus MAGE-A DNA vaccine generates robust CD8+ immune responses to MAGE-A1, A2, A3, A5 A6 and A8 isoforms in C57Bl/6 mice and CD-1 outbred mice. Consensus MAGE-A DNA vaccine generates some anti-tumor immunity in several lung and melanoma mouse tumor models.

Figure 19:
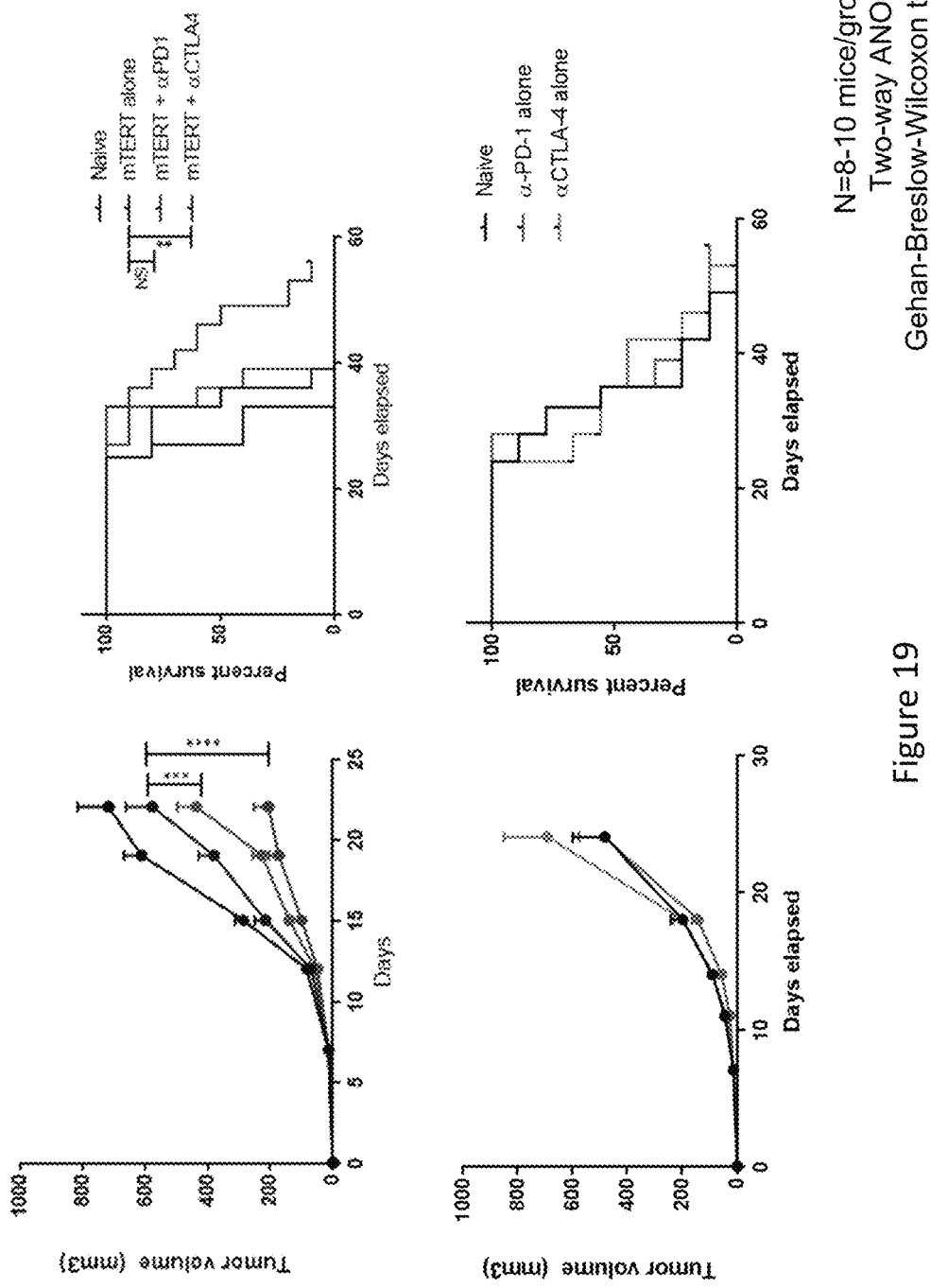
FIG. 19 depicts experimental results demonstrating αCTLA-4 and αPD-1 increases tumor control and survival.

Testing of MAGE-A vaccines in orthotopic/autochthonous mouse lung/melanoma models will show anti-tumor immunity. Further, combination therapy with immune checkpoint blockade, for example with αCTLA4 or αPD1 antibodies (FIG. 19), or with additional tumor antigen vaccines, for example TERT, WT1, may be effective.

Figure 20:
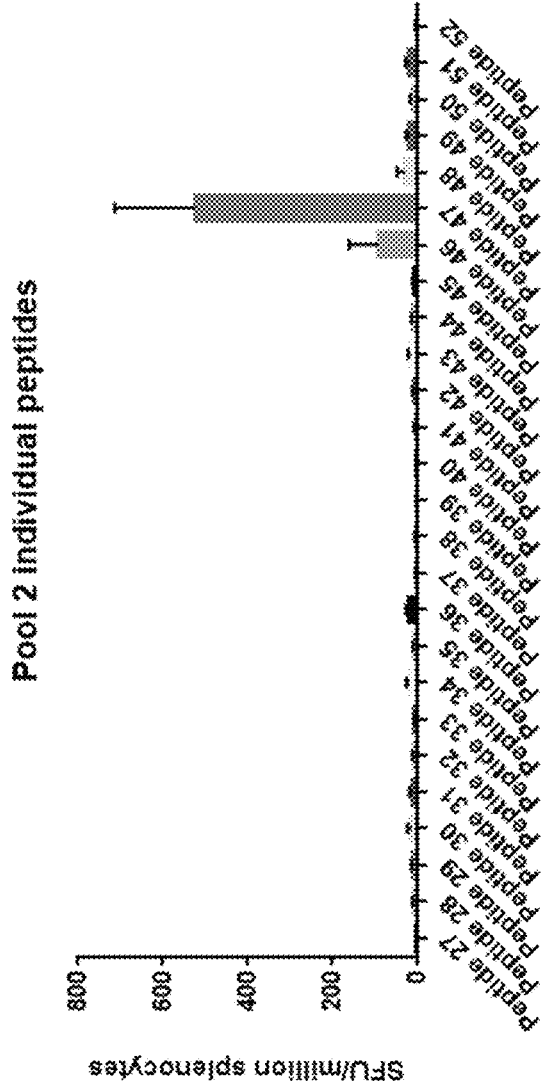
FIG. 20 depicts experimental results demonstrating the dominant MAGE-A epitope in C57Bl/6 mice.

Identification of the dominant MAGE-A epitope in C57Bl/6 mice showed a conserved dominant epitope among all isoforms, FASINKTHPRAYPEK (SEQ ID NO:14). This epitope is not the same as the dominant epitope previously identified for C57Bl/6 mice (FIG. 20).

What is claimed is:

1. An immunological composition comprising a nucleotide sequence encoding a consensus MAGE-A antigen, wherein the consensus MAGE-A antigen comprises an amino acid sequence selected from the group consisting of SEQ ID NO:1, SEQ ID NO:3, SEQ ID NO:5, SEQ ID NO:7, SEQ ID NO:9, SEQ ID NO:11, an amino acid sequence comprising the amino acid residues 19-333 of SEQ ID NO:3, an amino acid sequence comprising the amino acid residues 19-335 SEQ ID NO:7, and an amino acid sequence comprising the amino acid residues 19-338 of SEQ ID NO:11.

2. The immunological composition of claim 1, wherein the composition further comprises one or more nucleotide sequences encoding one or more additional cancer antigens.

3. The immunological composition of claim 2, wherein the one or more additional cancer antigens comprise one or more antigens selected from the group consisting of the amino acid sequence of tyrosinase (Tyr), the amino acid sequence of tyrosinase-related protein 1 (TYRP1), the amino acid sequence of tyrosinase-related protein 2 (TYRP2), the amino acid sequence of hTERT, the amino acid sequence of growth hormone release hormone (GHRH), the amino acid sequence of MART-1/melan-A antigen (MART-1/Melan-A), the amino acid sequence of cancer testis antigen (NY-ESO-1), the amino acid sequence of cancer testis antigen II (NY-ESO-2), the amino acid sequence of PRAME, the amino acid sequence of WT1, the amino acid sequence of PSA, the amino acid sequence of PSMA, the amino acid sequence of STEAP, the amino acid sequence of PSCA, the amino acid sequence of gp100, the amino acid sequence of a viral antigen, and a combination thereof.

4. The immunological composition of claim 1, wherein the composition further comprises one or more nucleotide sequences encoding one or more immune checkpoint inhibitors.

5. The immunological composition of claim 4, wherein the immune checkpoint inhibitor is selected from the group consisting of: anti-PD-1 antibody, anti-PD-L1 antibody, anti-TIM-3 antibody, anti-LAG-3 antibody, anti-CTLA4 antibody, and a combination thereof.

6. The immunological composition of claim 1, wherein the nucleotide sequence comprises a nucleotide sequence selected from the group consisting of: SEQ ID NO:2, SEQ ID NO:4, SEQ ID NO:6, SEQ ID NO:8 SEQ ID NO:10, SEQ ID NO:12, a nucleotide sequence that is 95% identical or greater to SEQ ID NO:2, a nucleotide sequence that is 95% identical or greater to SEQ ID NO:4, a nucleotide sequence that is 95% identical or greater to SEQ ID NO:6, a nucleotide sequence that is 95% identical or greater to SEQ ID NO:8, a nucleotide sequence that is 95% identical or greater to SEQ ID NO:10, and a nucleotide sequence that is 95% identical or greater to SEQ ID NO:12.

7. The immunological composition of claim 1, wherein the nucleotide sequence comprises one or more plasmids.

8. The immunological composition of claim 1, further comprising a nucleotide sequence encoding an adjuvant.

9. The immunological composition of claim 8, wherein the adjuvant is IL-12, IL-15, IL-28, or RANTES.

10. A method of treating cancer in a subject in need thereof, the method comprising administering the immunological composition of claim 1 to the subject.

11. The method of claim 10, wherein the administering step comprises electroporation.

12. The method of claim 10, further comprising administering one or more nucleotide sequences encoding one or more immune checkpoint inhibitors.

13. The method of claim 12, wherein the immune checkpoint inhibitor is selected from the group consisting of: anti-PD-1 antibody, anti-PD-L1 antibody, anti-TIM-3 antibody, anti-LAG-3 antibody, anti-CTLA4 antibody, and a combination thereof.

14. The method of claim 10, wherein the cancer is selected from the group consisting of: a blood cancer, lung cancer, melanoma, head and neck cancer, prostate cancer, liver cancer, cervical cancer, anal cancer, a papilloma and a combination thereof.

15. A nucleic acid molecule comprising one or more nucleotide sequences selected from the group consisting of: SEQ ID NO:2, SEQ ID NO:4, SEQ ID NO:6, SEQ ID NO:8 SEQ ID NO:10, SEQ ID NO:12, a nucleotide sequence comprising the nucleotide residues 55-999 of SEQ ID NO:4, a nucleotide sequence comprising the nucleotide residues 55-1005 of SEQ ID NO:8, and a nucleotide sequence comprising the nucleotide residues 55-1014 of SEQ ID NO:12.

16. The nucleic acid molecule of claim 15, wherein the nucleotide sequence comprises one or more plasmids.

17. A protein comprising one or more amino acid sequences selected from the group consisting of: SEQ ID NO:1, SEQ ID NO:3, SEQ ID NO:5, SEQ ID NO:7, SEQ ID NO:9, SEQ ID NO:11, an amino acid sequence comprising the amino acid residues 19-333 of SEQ ID NO:3, an amino acid sequence comprising the amino acid residues 19-335 of SEQ ID NO:7, and an amino acid sequence comprising the amino acid residues 19-338 of SEQ ID NO:11.

\* \* \* \* \*

SEQUENCE LISTING

```
<160> NUMBER OF SEQ ID NOS: 27

<210> SEQ ID NO 1
<211> LENGTH: 315
<212> TYPE: PRT
<213> ORGANISM: Artificial Sequence
<220> FEATURE:
<223> OTHER INFORMATION: Human MAGE-A CON1

<400> SEQUENCE: 1

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Thr Leu Val Glu Val
        35                  40                  45

Thr Leu Gly Glu Val Pro Ala Ala Glu Ser Pro Ser Pro His Ser
    50                  55                  60

Pro Gln Gly Ala Ser Ser Leu Pro Thr Thr Met Asn Tyr Thr Leu Trp
65                  70                  75                  80

Ser Gln Ser Asp Glu Gly Ser Ser Asn Gln Glu Glu Glu Gly Pro Ser
                85                  90                  95

Thr Phe Pro Asp Leu Glu Ser Glu Phe Gln Ala Ala Leu Ser Arg Lys
            100                 105                 110

Val Ala Glu Leu Val His Phe Leu Leu Leu Lys Tyr Arg Ala Arg Glu
            115                 120                 125

Pro Val Thr Lys Ala Glu Met Leu Gly Ser Val Val Arg Asn Trp Gln
        130                 135                 140

Tyr Phe Phe Pro Val Ile Phe Ser Lys Ala Ser Glu Tyr Leu Gln Leu
145                 150                 155                 160

Val Phe Gly Ile Glu Val Val Glu Val Val Pro Ile Gly His Leu Tyr
                165                 170                 175

Ile Leu Val Ala Thr Cys Leu Gly Leu Ser Tyr Asp Gly Leu Leu Gly
            180                 185                 190

Asp Asn Gln Ile Met Pro Lys Thr Gly Leu Leu Ile Ile Val Leu Ala
            195                 200                 205

Ile Ile Ala Lys Glu Gly Asp Cys Ala Pro Glu Glu Lys Ile Trp Glu
        210                 215                 220

Glu Leu Ser Val Leu Glu Val Phe Glu Gly Arg Glu Asp Ser Val Phe
225                 230                 235                 240

Ala His Pro Arg Lys Leu Leu Thr Gln Asp Phe Val Gln Glu Asn Tyr
                245                 250                 255

Leu Glu Tyr Arg Gln Val Pro Gly Ser Asp Pro Ala Cys Tyr Glu Phe
            260                 265                 270

Leu Trp Gly Pro Arg Ala Leu Ile Glu Thr Ser Tyr Val Lys Val Leu
        275                 280                 285

His His Met Leu Lys Ile Ser Gly Gly Pro His Ile Ser Tyr Pro Pro
    290                 295                 300
```

Leu His Glu Trp Ala Leu Arg Glu Gly Glu Glu
305             310             315

<210> SEQ ID NO 2
<211> LENGTH: 945
<212> TYPE: DNA
<213> ORGANISM: Artificial Sequence
<220> FEATURE:
<223> OTHER INFORMATION: Human MAGE-A CON1

<400> SEQUENCE: 2

```
atgcccctgg agcagcggag ccagcactgc aagcctgagg agggcctgga ggccaggggc    60
gaggccctgg gcctggtggg agcacaggcc cctgccaccg aggagcagga ggccgccagc   120
tcctctagca ccctggtgga ggtgacactg ggagaggtgc cagcagcaga gtctccaagc   180
cctccccact cccctcaggg agcctcctct ctgccaacca caatgaacta caccctgtgg   240
tcccagtctg acgagggcag ctccaatcag gaggaggagg ccctagcac attcccagat    300
ctggagtccg agtttcaggc cgccctgtct cggaaggtgg cagagctggt gcactttctg   360
ctgctgaagt atcgggccag agagccagtg acaaaggccg agatgctggg ctccgtggtg   420
agaaactggc agtacttctt ccccgtgatc ttcagcaagg cctccgagta tctgcagctg   480
gtgtttggca tcgaggtggt ggaggtggtg ccaatcggcc acctgtacat cctggtggcc   540
acctgcctgg gcctgagcta tgacggcctg ctgggcgata tcagatcat gcctaagaca    600
ggcctgctga tcatcgtgct ggccatcatc gccaaggagg gcgactgtgc cccagaggag   660
aagatctggg aggagctgag cgtgctggag gtgttcgagg gaagggagga ctccgtgttt   720
gcacacccca gaaagctgct gacccaggat ttcgtgcagg agaactacct ggagtatagg   780
caggtgcccg gctctgatcc tgcctgttac gagtttctgt ggggacccg cgccctgatc    840
gagacaagct atgtgaaggt gctgcaccac atgctgaaga tctctggcgg ccctcacatc   900
agctacccac ccctgcacga gtgggccctg cgggagggcg aggag                   945
```

<210> SEQ ID NO 3
<211> LENGTH: 333
<212> TYPE: PRT
<213> ORGANISM: Artificial Sequence
<220> FEATURE:
<223> OTHER INFORMATION: Human MAGE-A CON1 with IgE Leader

<400> SEQUENCE: 3

Met Asp Trp Thr Trp Ile Leu Phe Leu Val Ala Ala Thr Arg Val
1               5                   10                  15

His Ser Met Pro Leu Glu Gln Arg Ser Gln His Cys Lys Pro Glu Glu
            20                  25                  30

Gly Leu Glu Ala Arg Gly Glu Ala Leu Gly Leu Val Gly Ala Gln Ala
        35                  40                  45

Pro Ala Thr Glu Glu Gln Glu Ala Ala Ser Ser Ser Ser Thr Leu Val
    50                  55                  60

Glu Val Thr Leu Gly Glu Val Pro Ala Ala Glu Ser Pro Ser Pro Pro
65                  70                  75                  80

His Ser Pro Gln Gly Ala Ser Ser Leu Pro Thr Thr Met Asn Tyr Thr
                85                  90                  95

Leu Trp Ser Gln Ser Asp Glu Gly Ser Ser Asn Gln Glu Glu Glu Gly
            100                 105                 110

Pro Ser Thr Phe Pro Asp Leu Glu Ser Glu Phe Gln Ala Ala Leu Ser
        115                 120                 125

Arg Lys Val Ala Glu Leu Val His Phe Leu Leu Leu Lys Tyr Arg Ala
130                 135                 140

Arg Glu Pro Val Thr Lys Ala Glu Met Leu Gly Ser Val Val Arg Asn
145                 150                 155                 160

Trp Gln Tyr Phe Phe Pro Val Ile Phe Ser Lys Ala Ser Glu Tyr Leu
                165                 170                 175

Gln Leu Val Phe Gly Ile Glu Val Val Glu Val Val Pro Ile Gly His
                180                 185                 190

Leu Tyr Ile Leu Val Ala Thr Cys Leu Gly Leu Ser Tyr Asp Gly Leu
            195                 200                 205

Leu Gly Asp Asn Gln Ile Met Pro Lys Thr Gly Leu Leu Ile Ile Val
210                 215                 220

Leu Ala Ile Ile Ala Lys Glu Gly Asp Cys Ala Pro Glu Glu Lys Ile
225                 230                 235                 240

Trp Glu Glu Leu Ser Val Leu Glu Val Phe Glu Gly Arg Glu Asp Ser
                245                 250                 255

Val Phe Ala His Pro Arg Lys Leu Leu Thr Gln Asp Phe Val Gln Glu
                260                 265                 270

Asn Tyr Leu Glu Tyr Arg Gln Val Pro Gly Ser Asp Pro Ala Cys Tyr
            275                 280                 285

Glu Phe Leu Trp Gly Pro Arg Ala Leu Ile Glu Thr Ser Tyr Val Lys
290                 295                 300

Val Leu His His Met Leu Lys Ile Ser Gly Gly Pro His Ile Ser Tyr
305                 310                 315                 320

Pro Pro Leu His Glu Trp Ala Leu Arg Glu Gly Glu Glu
                325                 330

```
<210> SEQ ID NO 4
<211> LENGTH: 999
<212> TYPE: DNA
<213> ORGANISM: Artificial Sequence
<220> FEATURE:
<223> OTHER INFORMATION: Human MAGE-A CON1 with IgE Leader

<400> SEQUENCE: 4
atggactgga cctggattct gttcctggtg gcagcagcaa caagggtgca ctccatgccc      60
ctggagcagc ggagccagca ctgcaagcct gaggagggcc tggaggccag ggcgaggcc     120 ctgggcctgg tgggagcaca ggcccctgcc accgaggagc aggaggccgc cagctcctct    180
agcaccctgg tggaggtgac actgggagag gtgccagcag cagagtctcc aagccctccc    240 cactccccctc agggagcctc ctctctgcca accacaatga actacaccct gtggtcccag    300
tctgacgagg gcagctccaa tcaggaggag gagggcccta gcacattccc agatctggag    360
tccgagtttc aggccgccct gtctcggaag gtggcagagc tggtgcactt tctgctgctg    420
aagtatcggg ccagagagcc agtgacaaag gccgagatgc tgggctccgt ggtgagaaac    480
tggcagtact ctttcccgt gatcttcagc aaggcctccg agtatctgca gctggtgttt    540
ggcatcgagg tggtggaggt ggtgccaatc ggccacctgt acatcctggt ggccacctgc    600
ctgggcctga gctatgacgg cctgctgggc gataatcaga tcatgcctaa gacaggcctg    660
ctgatcatcg tgctggccat catcgccaag gagggcgact gtgccccaga ggagaagatc    720
tgggaggagc tgagcgtgct ggaggtgttc gagggaaggg aggactccgt gtttgcacac    780
cccagaaagc tgctgaccca ggatttcgtg caggagaact acctggagta taggcaggtg    840
cccggctctg atcctgcctg ttacgagttt ctgtggggac cccgcgccct gatcgagaca    900
```

```
agctatgtga aggtgctgca ccacatgctg aagatctctg gcggccctca catcagctac    960
ccacccctgc acgagtgggc cctgcgggag ggcgaggag                           999
```

<210> SEQ ID NO 5
<211> LENGTH: 316
<212> TYPE: PRT
<213> ORGANISM: Artificial Sequence
<220> FEATURE:
<223> OTHER INFORMATION: Human MAGE-A CON2

<400> SEQUENCE: 5

```
Ser Leu Glu Gln Lys Ser Gln His Cys Lys Pro Glu Glu Gly Leu Glu
1               5                   10                  15

Thr Gln Glu Glu Ala Leu Gly Leu Val Gly Val Gln Ala Ala Thr Thr
            20                  25                  30

Glu Glu Gln Glu Ala Ala Val Ser Ser Ser Pro Leu Val Pro Gly
        35                  40                  45

Thr Leu Glu Glu Val Pro Ala Ala Gly Ser Thr Gly Pro Pro Gln Ser
    50                  55                  60

Pro Gln Gly Ala Ser Ala Phe Pro Thr Thr Ile Asn Phe Thr Arg Trp
65                  70                  75                  80

Arg Gln Pro Ser Glu Gly Ser Ser Ser Gln Glu Glu Glu Gly Pro Ser
                85                  90                  95

Thr Ser Pro Asp Leu Glu Ser Leu Phe Arg Ala Ala Leu Ser Lys Lys
            100                 105                 110

Val Ala Asp Leu Val His Phe Leu Leu Leu Lys Tyr Arg Ala Arg Glu
        115                 120                 125

Leu Val Thr Lys Ala Glu Met Leu Glu Ser Val Ile Lys Asn Tyr Lys
    130                 135                 140

Arg Cys Phe Pro Glu Ile Phe Gly Lys Ala Ser Glu Ser Leu Lys Leu
145                 150                 155                 160

Ile Phe Gly Ile Asp Val Lys Glu Ala Asp Pro Thr Ser His Thr Tyr
                165                 170                 175

Val Leu Val Thr Cys Leu Gly Leu Ser Tyr Asp Gly Leu Leu Gly Asp
            180                 185                 190

Asn Gln Ile Met Pro Lys Thr Gly Leu Leu Ile Ile Val Leu Val Thr
        195                 200                 205

Ile Ala Met Glu Gly Gly Ser Ala Pro Glu Glu Ile Trp Glu Glu
    210                 215                 220

Leu Ser Val Met Glu Val Tyr Asp Gly Arg Glu His Ser Val Tyr Gly
225                 230                 235                 240

Glu Pro Arg Lys Leu Leu Thr Gln Asp Leu Val Gln Glu Asn Tyr Leu
                245                 250                 255

Glu Tyr Arg Gln Val Pro Asp Ser Asp Pro Ala Arg Tyr Glu Phe Leu
            260                 265                 270

Trp Gly Pro Arg Ala Leu Ala Glu Thr Ser Tyr Val Lys Val Leu Glu
        275                 280                 285

Tyr Val Val Lys Val Ser Ala Arg Val Arg Phe Ala Phe Pro Ser Leu
    290                 295                 300

Arg Glu Ala Ala Leu Arg Glu Glu Glu Gly Val
305                 310                 315
```

<210> SEQ ID NO 6
<211> LENGTH: 951
<212> TYPE: DNA

<213> ORGANISM: Artificial Sequence
<220> FEATURE:
<223> OTHER INFORMATION: Human MAGE-A CON2

<400> SEQUENCE: 6

```
atgtctctgg agcagaagag ccagcactgc aagccagagg agggcctgga gacacaggag      60
gaggccctgg gcctggtggg agtgcaggca gcaaccacag aggagcagga ggcagccgtg     120
agctcctcta gcccactggt gccaggcacc ctggaggagt gcctgcagc aggctctaca     180
ggccctcccc agtccccaca gggagcatct gccttcccaa ccacaatcaa ctttacccgg     240
tggagacagc catccgaggg ctcctctagc caggaggagg agggacctag cacatcccca     300
gacctggaga gcctgttccg ggccgccctg tccaagaagg tggcagatct ggtgcacttt     360
ctgctgctga gtacagggc ccgcgagctg gtgaccaagg cagagatgct ggagtccgtg     420
atcaagaact ataagagatg cttccccgag atctttggca aggcctctga gagcctgaag     480
ctgatcttcg gcatcgacgt gaaggaggcc gatcctacct cccacacata cgtgctggtg     540
acatgtctgg gcctgtctta tgacggcctg ctgggcgata atcagatcat gcctaagacc     600
ggcctgctga tcatcgtgct ggtgacaatc gcaatggagg cggctccgc cccagaggag     660
gagatctggg aggagctgtc tgtgatggag gtgtacgacg gcaggagca cagcgtgtat     720
ggcgagcctc gcaagctgct gacccaggat ctggtgcagg agaattacct ggagtatagg     780
caggtgccag acagcgatcc tgcaagatac gagtttctgt ggggcccaag agccctggcc     840
gagacatcct acgtgaaggt gctggagtat gtggtgaagg tgtctgcccg ggtgagattc     900
gcctttccca gctgaggga ggccgccctg cgcgaggagg aggagggcgt g               951
```

<210> SEQ ID NO 7
<211> LENGTH: 335
<212> TYPE: PRT
<213> ORGANISM: Artificial Sequence
<220> FEATURE:
<223> OTHER INFORMATION: Human MAGE-A CON2 with IgE Leader

<400> SEQUENCE: 7

```
Met Asp Trp Thr Trp Ile Leu Phe Leu Val Ala Ala Thr Arg Val
1               5                   10                  15

His Ser Met Ser Leu Glu Gln Lys Ser Gln His Cys Lys Pro Glu Glu
            20                  25                  30

Gly Leu Glu Thr Gln Glu Glu Ala Leu Gly Leu Val Gly Val Gln Ala
        35                  40                  45

Ala Thr Thr Glu Glu Gln Glu Ala Ala Val Ser Ser Ser Pro Leu
    50                  55                  60

Val Pro Gly Thr Leu Glu Glu Val Pro Ala Ala Gly Ser Thr Gly Pro
65                  70                  75                  80

Pro Gln Ser Pro Gln Gly Ala Ser Ala Phe Pro Thr Thr Ile Asn Phe
                85                  90                  95

Thr Arg Trp Arg Gln Pro Ser Glu Gly Ser Ser Ser Gln Glu Glu Glu
            100                 105                 110

Gly Pro Ser Thr Ser Pro Asp Leu Glu Ser Leu Phe Arg Ala Ala Leu
        115                 120                 125

Ser Lys Lys Val Ala Asp Leu Val His Phe Leu Leu Lys Tyr Arg
    130                 135                 140

Ala Arg Glu Leu Val Thr Lys Ala Glu Met Leu Glu Ser Val Ile Lys
145                 150                 155                 160

Asn Tyr Lys Arg Cys Phe Pro Glu Ile Phe Gly Lys Ala Ser Glu Ser
```

165                 170                 175
Leu Lys Leu Ile Phe Gly Ile Asp Val Lys Glu Ala Asp Pro Thr Ser
            180                 185                 190

His Thr Tyr Val Leu Val Thr Cys Leu Gly Leu Ser Tyr Asp Gly Leu
        195                 200                 205

Leu Gly Asp Asn Gln Ile Met Pro Lys Thr Gly Leu Leu Ile Ile Val
    210                 215                 220

Leu Val Thr Ile Ala Met Glu Gly Gly Ser Ala Pro Glu Glu Glu Ile
225                 230                 235                 240

Trp Glu Glu Leu Ser Val Met Glu Val Tyr Asp Gly Arg Glu His Ser
                245                 250                 255

Val Tyr Gly Glu Pro Arg Lys Leu Leu Thr Gln Asp Leu Val Gln Glu
            260                 265                 270

Asn Tyr Leu Glu Tyr Arg Gln Val Pro Asp Ser Asp Pro Ala Arg Tyr
        275                 280                 285

Glu Phe Leu Trp Gly Pro Arg Ala Leu Ala Glu Thr Ser Tyr Val Lys
    290                 295                 300

Val Leu Glu Tyr Val Val Lys Val Ser Ala Arg Val Arg Phe Ala Phe
305                 310                 315                 320

Pro Ser Leu Arg Glu Ala Ala Leu Arg Glu Glu Glu Gly Val
                325                 330                 335

<210> SEQ ID NO 8
<211> LENGTH: 1005
<212> TYPE: DNA
<213> ORGANISM: Artificial Sequence
<220> FEATURE:
<223> OTHER INFORMATION: Human MAGE-A CON2 with IgE Leader

<400> SEQUENCE: 8
atggactgga cctggattct gttcctggtg gcagcagcaa caagggtgca ctccatgtct      60
ctggagcaga gagccagca ctgcaagcca gaggagggcc tggagacaca ggaggaggcc     120
ctgggcctgg tgggagtgca ggcagcaacc acagaggagc aggaggcagc cgtgagctcc    180
tctagcccac tggtgccagg caccctggag gaggtgcctg cagcaggctc tacaggccct    240
ccccagtccc cacagggagc atctgccttc ccaaccacaa tcaactttac ccggtggaga    300
cagccatccg agggctcctc tagccaggag gaggagggac ctagcacatc cccagacctg    360
gagagcctgt tccgggccgc cctgtccaag aaggtggcag atctggtgca ctttctgctg    420
ctgaagtaca gggcccgcga gctggtgacc aaggcagaga tgctggagtc cgtgatcaag    480
aactataaga gatgcttccc cgagatcttt ggcaaggcct ctgagagcct gaagctgatc    540
ttcggcatcg acgtgaagga ggccgatcct acctcccaca catacgtgct ggtgacatgt    600
ctgggcctgt cttatgacgg cctgctgggc gataatcaga tcatgcctaa gaccggcctg    660
ctgatcatcg tgctggtgac aatcgcaatg gagggcggct ccgccccaga ggaggagatc    720
tgggaggagc tgtctgtgat ggaggtgtac gacggcaggg agcacagcgt gtatggcgag    780
cctcgcaagc tgctgaccca ggatctggtg caggagaatt acctggagta taggcaggtg    840
ccagacagcg atcctgcaag atacgagttt ctgtggggcc caagagccct ggccgagaca    900
tcctacgtga aggtgctgga gtatgtggtg aaggtgtctg cccgggtgag attcgccttt    960
cccagcctga gggaggccgc cctgcgcgag gaggaggagg gcgtg                   1005

<210> SEQ ID NO 9
<211> LENGTH: 320

```
<212> TYPE: PRT
<213> ORGANISM: Artificial Sequence
<220> FEATURE:
<223> OTHER INFORMATION: Mouse MAGE-A SynCON

<400> SEQUENCE: 9

Met Ala Asp Ser His Asn Thr Gln Tyr Cys Asn Leu Gln Glu Ser Ala
1               5                   10                  15

Gln Ala Gln Gln Glu Leu Asp Asn Asp Gln Glu Thr Met Ala Thr Ser
            20                  25                  30

Glu Glu Glu Glu Asp Thr Thr Thr Ser Asn Lys Val Tyr Gly Ser Gly
        35                  40                  45

Ile Pro Ser Pro Pro Gln Ser Pro Gln Arg Ala Tyr Ser Pro Cys Val
    50                  55                  60

Ile Leu Ala Ser Ile Pro Asp Ser Pro Ser Glu Glu Ala Ser Ile Lys
65                  70                  75                  80

Gly Ser Glu Gly Leu Glu Asp Pro Leu Tyr Leu Leu His Asn Ala Gln
                85                  90                  95

Asn Thr Lys Val Tyr Asp Leu Val Asp Phe Leu Val Leu Lys Tyr Gln
            100                 105                 110

Met Lys Ala Phe Thr Thr Lys Ala Glu Met Leu Glu Ser Ile Gly Arg
        115                 120                 125

Glu Tyr Glu Glu Tyr Tyr Pro Leu Ile Phe Ser Glu Ala Ser Glu Cys
    130                 135                 140

Phe Lys Met Val Phe Gly Leu Asp Met Val Glu Val Asp Pro Phe Val
145                 150                 155                 160

His Ser Tyr Ile Leu Val Thr Ala Leu Gly Ile Thr Tyr Asp Gly Met
                165                 170                 175

Met Thr Asp Val Gln Ser Met Pro Lys Thr Gly Ile Leu Ile Ala Val
            180                 185                 190

Leu Ser Val Ile Phe Met Lys Gly Asn Tyr Val Ser Glu Glu Ile Ile
        195                 200                 205

Trp Glu Met Leu Asn Asn Ile Gly Leu Tyr Gly Gly Arg Asp Pro Tyr
    210                 215                 220

Ile His Lys Asp Pro Arg Lys Phe Ile Ser Glu Glu Phe Val Gln Glu
225                 230                 235                 240

Gly Tyr Leu Glu Tyr Arg Gln Val Pro Asn Ser Asp Pro Pro Ser Tyr
                245                 250                 255

Gly Phe Leu Trp Gly Pro Arg Ala Phe Ala Glu Thr Thr Lys Met Lys
            260                 265                 270

Val Leu Gln Phe Phe Ala Ser Ile Asn Lys Thr His Pro Arg Ala Tyr
        275                 280                 285

Pro Glu Lys Tyr Ala Glu Ala Leu Gln Asp Glu Ile Asp Arg Thr Lys
    290                 295                 300

Ala Trp Ile Leu Asn Arg Cys Ser Asn Ser Ser Asp Leu Leu Thr Phe
305                 310                 315                 320

<210> SEQ ID NO 10
<211> LENGTH: 960
<212> TYPE: DNA
<213> ORGANISM: Artificial Sequence
<220> FEATURE:
<223> OTHER INFORMATION: Mouse MAGE-A SynCON

<400> SEQUENCE: 10
atggccgatt ctcataatac ccagtattgt aacctgcagg agtccgccca ggctcagcag    60
```

```
gagctggaca acgatcagga gacaatggcc acctccgagg aggaggagga caccacaacc    120
tctaacaagg tgtacggctc cggaatccca tctcccctc agagccccca gagggcctac    180
tctccttgcg tgatcctggc tagcatccct gacagcccat ccgaggaggc ctccatcaag    240
ggctctgagg gcctggagga ccccctgtac ctgctgcaca acgctcagaa cacaaaggtg    300
tacgacctgg tggatttcct ggtgctgaag taccagatga aggcctttac aaccaaggct    360
gagatgctgg agagcatcgg ccgggagtac gaggagtact accccctgat cttctctgag    420
gccagcgagt gtttcaagat ggtgtttgga ctggacatgg tggaggtgga ccccttcgtg    480
cactcttaca tcctggtgac agccctgggc atcacctacg acggaatgat gacagatgtg    540
cagagcatgc ccaagaccgg catcctgatc gctgtgctga gcgtgatctt catgaaggga    600
aactacgtgt ccgaggagat catctgggag atgctgaaca acatcggcct gtacggcgga    660
agggacccat acatccacaa ggaccccaga aagttcatct ccgaggagtt tgtgcaggag    720
ggctacctgg agtaccggca ggtgcctaac agcgacccac cctcctacgg cttcctgtgg    780
ggaccacgcg cctttgctga gacaaccaag atgaaggtgc tgcagttctt tgcctctatc    840
aacaagaccc accccagggc ttaccctgag aagtacgccg aggctctgca ggatgagatc    900
gatcggacaa aagcctggat tctcaaccgc tgttctaact cctctgacct gctgaccttc    960
```

```
<210> SEQ ID NO 11
<211> LENGTH: 338
<212> TYPE: PRT
<213> ORGANISM: Artificial Sequence
<220> FEATURE:
<223> OTHER INFORMATION: Mouse MAGE-A SynCON with IgE Leader

<400> SEQUENCE: 11
```

Met Asp Trp Thr Trp Ile Leu Phe Leu Val Ala Ala Thr Arg Val
1               5                   10                  15

His Ser Met Ala Asp Ser His Asn Thr Gln Tyr Cys Asn Leu Gln Glu
            20                  25                  30

Ser Ala Gln Ala Gln Gln Glu Leu Asp Asn Asp Gln Glu Thr Met Ala
        35                  40                  45

Thr Ser Glu Glu Glu Glu Asp Thr Thr Thr Ser Asn Lys Val Tyr Gly
    50                  55                  60

Ser Gly Ile Pro Ser Pro Pro Gln Ser Pro Gln Arg Ala Tyr Ser Pro
65                  70                  75                  80

Cys Val Ile Leu Ala Ser Ile Pro Asp Ser Pro Ser Glu Glu Ala Ser
                85                  90                  95

Ile Lys Gly Ser Glu Gly Leu Glu Asp Pro Leu Tyr Leu Leu His Asn
            100                 105                 110

Ala Gln Asn Thr Lys Val Tyr Asp Leu Val Asp Phe Leu Val Leu Lys
        115                 120                 125

Tyr Gln Met Lys Ala Phe Thr Thr Lys Ala Glu Met Leu Glu Ser Ile
    130                 135                 140

Gly Arg Glu Tyr Glu Glu Tyr Tyr Pro Leu Ile Phe Ser Glu Ala Ser
145                 150                 155                 160

Glu Cys Phe Lys Met Val Phe Gly Leu Asp Met Val Glu Val Asp Pro
                165                 170                 175

Phe Val His Ser Tyr Ile Leu Val Thr Ala Leu Gly Ile Thr Tyr Asp
            180                 185                 190

Gly Met Met Thr Asp Val Gln Ser Met Pro Lys Thr Gly Ile Leu Ile
        195                 200                 205

Ala Val Leu Ser Val Ile Phe Met Lys Gly Asn Tyr Val Ser Glu Glu
210                 215                 220

Ile Ile Trp Glu Met Leu Asn Asn Ile Gly Leu Tyr Gly Gly Arg Asp
225                 230                 235                 240

Pro Tyr Ile His Lys Asp Pro Arg Lys Phe Ile Ser Glu Glu Phe Val
            245                 250                 255

Gln Glu Gly Tyr Leu Glu Tyr Arg Gln Val Pro Asn Ser Asp Pro Pro
                260                 265                 270

Ser Tyr Gly Phe Leu Trp Gly Pro Arg Ala Phe Ala Glu Thr Thr Lys
            275                 280                 285

Met Lys Val Leu Gln Phe Phe Ala Ser Ile Asn Lys Thr His Pro Arg
290                 295                 300

Ala Tyr Pro Glu Lys Tyr Ala Glu Ala Leu Gln Asp Glu Ile Asp Arg
305                 310                 315                 320

Thr Lys Ala Trp Ile Leu Asn Arg Cys Ser Asn Ser Ser Asp Leu Leu
                325                 330                 335

Thr Phe

<210> SEQ ID NO 12
<211> LENGTH: 1014
<212> TYPE: DNA
<213> ORGANISM: Artificial Sequence
<220> FEATURE:
<223> OTHER INFORMATION: Mouse MAGE-A SynCON with IgE Leader

<400> SEQUENCE: 12
atggattgga cttggattct gtttctcgtc gctgccgcaa ctagagtgca tagcatggcc      60
gattctcata tacccagta ttgtaacctg caggagtccg cccaggctca gcaggagctg      120
gacaacgatc aggagacaat ggccacctcc gaggaggagg aggacaccac aacctctaac      180
aaggtgtacg gctccggaat cccatctccc cctcagagcc cccagagggc ctactctcct      240
tgcgtgatcc tggctagcat ccctgacagc ccatccgagg aggcctccat caagggctct      300
gagggcctgg aggacccccct gtacctgctg cacaacgctc agaacacaaa ggtgtacgac      360
ctggtggatt tcctggtgct gaagtaccag atgaaggcct tacaaccaa ggctgagatg      420
ctggagagca tcggccggga gtacgaggag tactacccc tgatcttctc tgaggccagc      480
gagtgtttca gatggtgtt tggactggac atggtggagg tggacccctt cgtgcactct      540
tacatcctgg tgacagccct gggcatcacc tacgacggaa tgatgacaga tgtgcagagc      600
atgcccaaga ccggcatcct gatcgctgtg ctgagcgtga tcttcatgaa gggaaactac      660
gtgtccgagg agatcatctg ggagatgctg aacaacatcg gcctgtacgg cggaagggac      720
ccatacatcc acaaggaccc cagaaagttc atctccgagg agtttgtgca ggagggctac      780
ctggagtacc ggcaggtgcc taacagcgac ccaccctcct acggcttcct gtggggacca      840
cgcgcctttg ctgagacaac caagatgaag gtgctgcagt tctttgcctc tatcaacaag      900
acccacccca gggcttaccc tgagaagtac gccgaggctc tgcaggatga gatcgatcgg      960
acaaaagcct ggattctcaa ccgctgttct aactcctctg acctgctgac cttc           1014

<210> SEQ ID NO 13
<211> LENGTH: 18
<212> TYPE: PRT
<213> ORGANISM: Artificial Sequence
<220> FEATURE:
<223> OTHER INFORMATION: IgE Leader

<400> SEQUENCE: 13

Met Asp Trp Thr Trp Ile Leu Phe Leu Val Ala Ala Ala Thr Arg Val
1               5                   10                  15

His Ser

<210> SEQ ID NO 14
<211> LENGTH: 15
<212> TYPE: PRT
<213> ORGANISM: Artificial Sequence
<220> FEATURE:
<223> OTHER INFORMATION: dominant MAGE-A epitope

<400> SEQUENCE: 14

Phe Ala Ser Ile Asn Lys Thr His Pro Arg Ala Tyr Pro Glu Lys
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: MAGE dominat epitope

<400> SEQUENCE: 15

Met Lys Val Leu Gln Phe Phe Ala Ser Ile Asn Lys Thr His Pro
1               5                   10                  15

<210> SEQ ID NO 16
<211> LENGTH: 8
<212> TYPE: PRT
<213> ORGANISM: Artificial Sequence
<220> FEATURE:
<223> OTHER INFORMATION: MAGE dominat epitope 8-mer

<400> SEQUENCE: 16

Val Leu Gln Phe Phe Ala Ser Ile
1               5

<210> SEQ ID NO 17
<211> LENGTH: 9
<212> TYPE: PRT
<213> ORGANISM: Artificial Sequence
<220> FEATURE:
<223> OTHER INFORMATION: MAGE dominat epitope 9-mer

<400> SEQUENCE: 17

Lys Val Leu Gln Phe Phe Ala Ser Ile
1               5

<210> SEQ ID NO 18
<211> LENGTH: 24
<212> TYPE: DNA
<213> ORGANISM: Artificial Sequence
<220> FEATURE:
<223> OTHER INFORMATION: chemically synthesized

<400> SEQUENCE: 18
ccacctcaaa taaagtgtat ggca                                    24

<210> SEQ ID NO 19
<211> LENGTH: 21
<212> TYPE: DNA
<213> ORGANISM: Artificial Sequence
<220> FEATURE:
<223> OTHER INFORMATION: chemically synthesized

<400> SEQUENCE: 19
accagaaagt ccaccaagtc a                                          21

<210> SEQ ID NO 20
<211> LENGTH: 20
<212> TYPE: DNA
<213> ORGANISM: Artificial Sequence
<220> FEATURE:
<223> OTHER INFORMATION: chemically synthesized

<400> SEQUENCE: 20
gccaccatgg attggacttg                                            20

<210> SEQ ID NO 21
<211> LENGTH: 20
<212> TYPE: DNA
<213> ORGANISM: Artificial Sequence
<220> FEATURE:
<223> OTHER INFORMATION: chemically synthesized

<400> SEQUENCE: 21
tggccattgt ctcctgatcg                                            20

<210> SEQ ID NO 22
<211> LENGTH: 20
<212> TYPE: DNA
<213> ORGANISM: Artificial Sequence
<220> FEATURE:
<223> OTHER INFORMATION: chemically synthesized

<400> SEQUENCE: 22
gtttgcacac cccagaaagc                                            20

<210> SEQ ID NO 23
<211> LENGTH: 20
<212> TYPE: DNA
<213> ORGANISM: Artificial Sequence
<220> FEATURE:
<223> OTHER INFORMATION: chemically synthesized

<400> SEQUENCE: 23
gggtgggtag ctgatgtgag                                            20

<210> SEQ ID NO 24
<211> LENGTH: 20
<212> TYPE: DNA
<213> ORGANISM: Artificial Sequence
<220> FEATURE:
<223> OTHER INFORMATION: chemically synthesized

<400> SEQUENCE: 24
tggcagatct ggtgcacttt                                            20

<210> SEQ ID NO 25
<211> LENGTH: 20
<212> TYPE: DNA
<213> ORGANISM: Artificial Sequence
<220> FEATURE:
<223> OTHER INFORMATION: chemically synthesized

<400> SEQUENCE: 25
ttcacgtcga tgccgaagat                                            20

<210> SEQ ID NO 26
<211> LENGTH: 20
<212> TYPE: DNA

```
<213> ORGANISM: Artificial Sequence
<220> FEATURE:
<223> OTHER INFORMATION: chemically synthesized

<400> SEQUENCE: 26
cctgcaccac caactgctta                                           20

<210> SEQ ID NO 27
<211> LENGTH: 21
<212> TYPE: DNA
<213> ORGANISM: Artificial Sequence
<220> FEATURE:
<223> OTHER INFORMATION: chemically synthesized

<400> SEQUENCE: 27
agtgatggca tggactgtgg t                                         21
```